(12) United States Patent
Belcher et al.

(10) Patent No.: US 11,508,968 B2
(45) Date of Patent: Nov. 22, 2022

(54) MICROPOROUS CARBON NANOFIBERS

(71) Applicant: Massachusetts Institute of Technology, Cambridge, MA (US)

(72) Inventors: Angela Belcher, Lexington, MA (US); Jifa Qi, West Roxbury, MA (US); Geran Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 306 days.

(21) Appl. No.: 16/278,041

(22) Filed: Feb. 15, 2019

(65) Prior Publication Data

US 2019/0260032 A1  Aug. 22, 2019

Related U.S. Application Data

(60) Provisional application No. 62/710,299, filed on Feb. 16, 2018.

(51) Int. Cl.
| | |
|---|---|
| *H01M 4/66* | (2006.01) |
| *C01B 32/158* | (2017.01) |
| *C12N 7/00* | (2006.01) |
| *H01M 10/052* | (2010.01) |
| *B82Y 30/00* | (2011.01) |
| *B82Y 40/00* | (2011.01) |
| *H01M 4/02* | (2006.01) |

(52) U.S. Cl.
CPC ........... *H01M 4/663* (2013.01); *C01B 32/158* (2017.08); *C12N 7/00* (2013.01); *B82Y 30/00* (2013.01); *B82Y 40/00* (2013.01); *C12N 2795/14031* (2013.01); *H01M 10/052* (2013.01); *H01M 2004/028* (2013.01)

(58) Field of Classification Search
CPC .............. H01M 4/663; H01M 10/052; H01M 2004/028; H01M 50/431; H01M 50/44; H01M 50/449; H01M 50/411; H01M 4/38; H01M 4/382; C01B 32/158; C12N 7/00; C12N 2795/14031; C12N 2795/14121; C12N 2795/14131; C12N 2795/14122; B82Y 30/00; B82Y 40/00; B82Y 5/00; Y02E 60/10; D01F 6/78
See application file for complete search history.

(56) References Cited

U.S. PATENT DOCUMENTS

| | | |
|---|---|---|
| 7,718,155 B2 | 5/2010 | Zhang et al. |
| 10,195,587 B2 | 2/2019 | Bakker et al. |
| | (Continued) | |

OTHER PUBLICATIONS

Definition of "precursor," accessed online at https://www.merriam-webster.com/dictionary/precursor on Jul. 21, 2021 (Year: 2021).*

(Continued)

*Primary Examiner* — Daniel C. McCracken
(74) *Attorney, Agent, or Firm* — Honigman LLP

(57) ABSTRACT

A composition can include a carbon nanofiber, wherein a precursor for the carbon nanofiber includes an alcohol and an aldehyde crosslinked by a primary amine. In certain embodiments, the carbon nanofiber can be biotemplated. Biotemplating enables precise control of morphology at the nanometer scale, while molecular templating allows control of carbon nanotexture and structure at the sub-nanometer scale.

25 Claims, 60 Drawing Sheets

(56) References Cited

U.S. PATENT DOCUMENTS

| | | | |
|---|---|---|---|
| 2007/0134151 A1* | 6/2007 | Jo | C01B 32/382 423/448 |
| 2007/0265162 A1 | 11/2007 | Zhang et al. | |
| 2009/0118457 A1 | 5/2009 | Gerber | |
| 2012/0028798 A1* | 2/2012 | Worsley | C01B 33/027 502/439 |
| 2017/0252725 A1 | 9/2017 | Bakker et al. | |
| 2019/0260032 A1 | 8/2019 | Belcher et al. | |

OTHER PUBLICATIONS

Terminology for carbon nanostructures, British Standards Institution PAS 134:2007 at 5 (2007) (Year: 2007).*

Fitzer, et al., Recommended Terminology for the Description of Carbon as a Solid, Pure & Appl. Chem. 1995; 67(3): 473-506 (Year: 1995).*

International Search Report and Written Opinion for PCT/US2019/018364 dated Dec. 27, 2019.

\* cited by examiner

MICROPOROUS CARBON NANOFIBERS

CLAIM OF PRIORITY

This application claims priority to U.S. Provisional Patent Application No. 62/710,299, filed Feb. 16, 2018, which is incorporated by reference in its entirety.

STATEMENT REGARDING FEDERALLY SPONSORED RESEARCH OR DEVELOPMENT

This invention was made with Government support under Grant No. HR0011-15-C-0084 awarded by the 000160—Defense Advanced Research Projects Agency. The Government has certain rights in the invention.

TECHNICAL FIELD

This invention relates to carbon nanofibers.

BACKGROUND

Carbon nanofibers have tremendous technological importance in wide-ranging areas such as energy storage, environmental remediation and catalysis. However, conventional synthesis processes are often laborious and lack fine control over morphology and nanotexture.

SUMMARY

In general, a composition includes a carbon nanofiber, wherein a precursor for the carbon nanofiber includes an alcohol and an aldehyde crosslinked by a primary amine.

In certain embodiments, the precursor for the carbon nanofiber is associated with a template.

In other embodiments, the template is a bacteriophage. In certain embodiments, the bacteriophage is M13. In certain embodiments, the template is a carbon nanotube. In certain embodiments, the template is an iron oxide nanoparticle. In certain embodiments, the M13 is modified by inserting an EEAE peptide moiety. In certain embodiments, the alcohol is resorcinol. In certain embodiments, the aldehyde is formaldehyde. In certain embodiments, the primary amine is a bifunctional primary amine. In certain embodiments, the bifunctional primary amine is ethylenediamine. In certain embodiments, the primary amine includes a silicon moiety. In certain embodiments, the primary amine is 3-aminopropyltrimethoxysilane (APTMS). In certain embodiments, the composition includes pores. In certain embodiments, the pores include micropores smaller than 2 nm in size. In certain embodiments, the pores include macropores bigger than 100 nm in size. In certain embodiments, a surface area of the composition is in a range of 200 $m^2/g$ and 2000 $m^2/g$.

In general, a method of making a composition including a carbon nanofiber including forming a precursor by crosslinking an alcohol and an aldehyde using a primary amine; and carbonizing the precursor.

In certain embodiments, the method further includes incorporating the precursor in a template. In certain embodiments, the template is a bacteriophage. In certain examples, the bacteriophage is M13. In certain embodiments, the template is a carbon nanotube. In certain embodiments, the template is an iron oxide nanoparticle. In certain embodiments, the M13 is modified by inserting an EEAE peptide moiety.

In certain embodiments, the alcohol is resorcinol. In certain embodiments, the aldehyde is formaldehyde. In certain embodiments, the primary amine is a bifunctional primary amine. In certain embodiments, the bifunctional primary amine is ethylenediamine. In certain embodiments, the primary amine includes a silicon moiety. In certain embodiments, the primary amine is 3-aminopropyltrimethoxysilane (APTMS). In certain embodiments, the composition includes pores. In certain embodiments, the pores include micropores smaller than 20 nm in size. In certain embodiments, the pores include macropores bigger than 100 nm in size. In certain embodiments, a surface area of the carbon nanofiber is in a range of 200 $m^2/g$ and 2000 $m^2/g$. In certain embodiments, the precursor includes a single phase of crosslinked polysiloxane, aliphatic and phenolic moieties. In certain embodiments, the forming the precursor is carried out in a pH range of 8.3-8.8. In certain embodiments, the forming the precursor is carried out with mechanical agitation. In certain embodiments, the forming the precursor is carried out without mechanical agitation. In certain embodiments, the forming the precursor is carried out in a pH below 8.3 with no mechanical agitation. In certain embodiments, the method further includes tuning nanotexture of the carbon nanofiber by tuning a content of the silicon moiety.

In general, a method of removing a contaminant includes administering into a contaminated site a composition including a carbon nanofiber, wherein a precursor for the carbon nanofiber includes an alcohol and an aldehyde crosslinked by a primary amine; and removing the composition after adsorption to a contaminant.

In certain embodiments, the precursor for the carbon nanofiber is associated with a template. In certain embodiments, the template is a bacteriophage. In certain embodiments, the bacteriophage is M13.

In certain embodiments, the template is a carbon nanotube. In certain embodiments, the template is an iron oxide nanoparticle.

In certain embodiments, the M13 is modified by inserting an EEAE peptide moiety. In certain embodiments, the alcohol is resorcinol. In certain embodiments, wherein the aldehyde is formaldehyde. In certain embodiments, the primary amine is a bifunctional primary amine. In certain embodiments, the bifunctional primary amine is ethylenediamine. In certain embodiments, the primary amine includes a silicon moiety. In certain embodiments, the primary amine is 3-aminopropyltrimethoxysilane (APTMS).

In certain embodiments, the composition includes pores. In certain embodiments, the pores include micropores smaller than 2 nm in size. In certain embodiments, the pores include macropores bigger than 100 nm in size.

In certain embodiments, a surface area of the composition is in a range of 200 $m^2/g$ and 2000 $m^2/g$.

In certain embodiments, the contaminated site is a gastric tract. In certain embodiments, the contaminated site is a natural environment.

In certain embodiments, the contaminant includes a phenolic compound, a pharmaceutical compound, a heavy ion, an organophosphate, a chemical warfare agent, a dye or a gas.

In general, an energy storage device includes a cathode including sulfur; an anode including lithium; a separator between the cathode and the anode; and a carbon interlayer between a cathode and a separator, wherein the carbon interlayer includes a composition comprising: a carbon nanofiber, wherein a precursor for the carbon nanofiber includes an alcohol and an aldehyde crosslinked by a primary amine.

In certain embodiments, the precursor for the carbon nanofiber is associated with a template. In certain embodiments, the template is a bacteriophage. In certain embodiments, the bacteriophage is M13.

In certain embodiments, the template is a carbon nanotube. In certain embodiments, the template is an iron oxide nanoparticle. In certain embodiments, the M13 is modified by inserting an EEAE peptide moiety. In certain examples, the alcohol is resorcinol. In certain embodiments, the aldehyde is formaldehyde. In certain embodiments, the primary amine is a bifunctional primary amine. In certain embodiments, the bifunctional primary amine is ethylenediamine. In certain embodiments, the primary amine includes a silicon moiety. In certain embodiments, wherein the primary amine is 3-aminopropyltrimethoxysilane (APTMS). In certain embodiments, wherein the composition includes pores. In certain embodiments, the pores include micropores smaller than 20 nm in size. In certain embodiments, the pores include macropores bigger than 100 nm in size. In certain embodiments, a surface area of the composition is in a range of 200 $m^2/g$ and 2000 $m^2/g$.

Other aspects, embodiments, and features will be apparent from the following description, the drawings, and the claims.

BRIEF DESCRIPTION OF THE DRAWINGS

FIGS. 3A-3C are low-resolution TEM micrographs of biotemplated carbon nanofibers (RFN-1100C, RFN10-1100C and RFN30-1100C). Insets show the corresponding carbon nanotexture after FFT processing. FIG. 3D is a medium-resolution micrograph of RFN30-1100C, showing high fiber uniformity. Corresponding Raman spectra and XRD diffractograms are shown in FIGS. 3E and 3F, respectively. BET isotherms and the corresponding DFT pore size distributions are shown in FIGS. 3G and 3H, respectively.

FIG. 4A shows the equilibrium uptake of various phenolic molecules, pharmaceutics and heavy ions. The equilibrium uptake of methylene blue is compared to some commercial carbons in FIG. 4B. FIG. 4C compares the methylene blue adsorption rate of RFN30-1100C against commercial activated charcoal (AC) with an initial substrate concentration of 1 mg/mL. FIG. 4D compares the adsorption rate for propranolol in SGF with initial concentration of 0.25 mg/mL.

FIG. 5C compares the galvanostatic cycling performance at 1 C charge and discharge rates for the first 300 cycles. The initial cyclic voltammograms and galvanostatic voltage profiles are shown in FIGS. 5D and 5E respectively.

FIG. 19, panel A shows photographs of the as-prepared nanofibers show a gradual change in color from dark-red to off-white as the polysiloxane content was increased (RFN to RFN50 from left to right).

FIG. 19, panel B shows transmission electron micrographs show uniform nanofiber morphologies across all samples with average diameters of 34.5 nm, 32.2 nm, 41.9 nm and 35.7 nm (RFN to RFN50 from top to bottom). Scale bars: (left column) 1 μm and (right column) 300 nm.

FIG. 19, panel C shows ATR-FTIR. FIG. 19, panel D shows XPS spectra of resorcinol-formaldehyde nanofibers (RFN through RFN50). FIG. 19, panel E shows WAXS analysis.

DETAILED DESCRIPTION

Figure 1A:
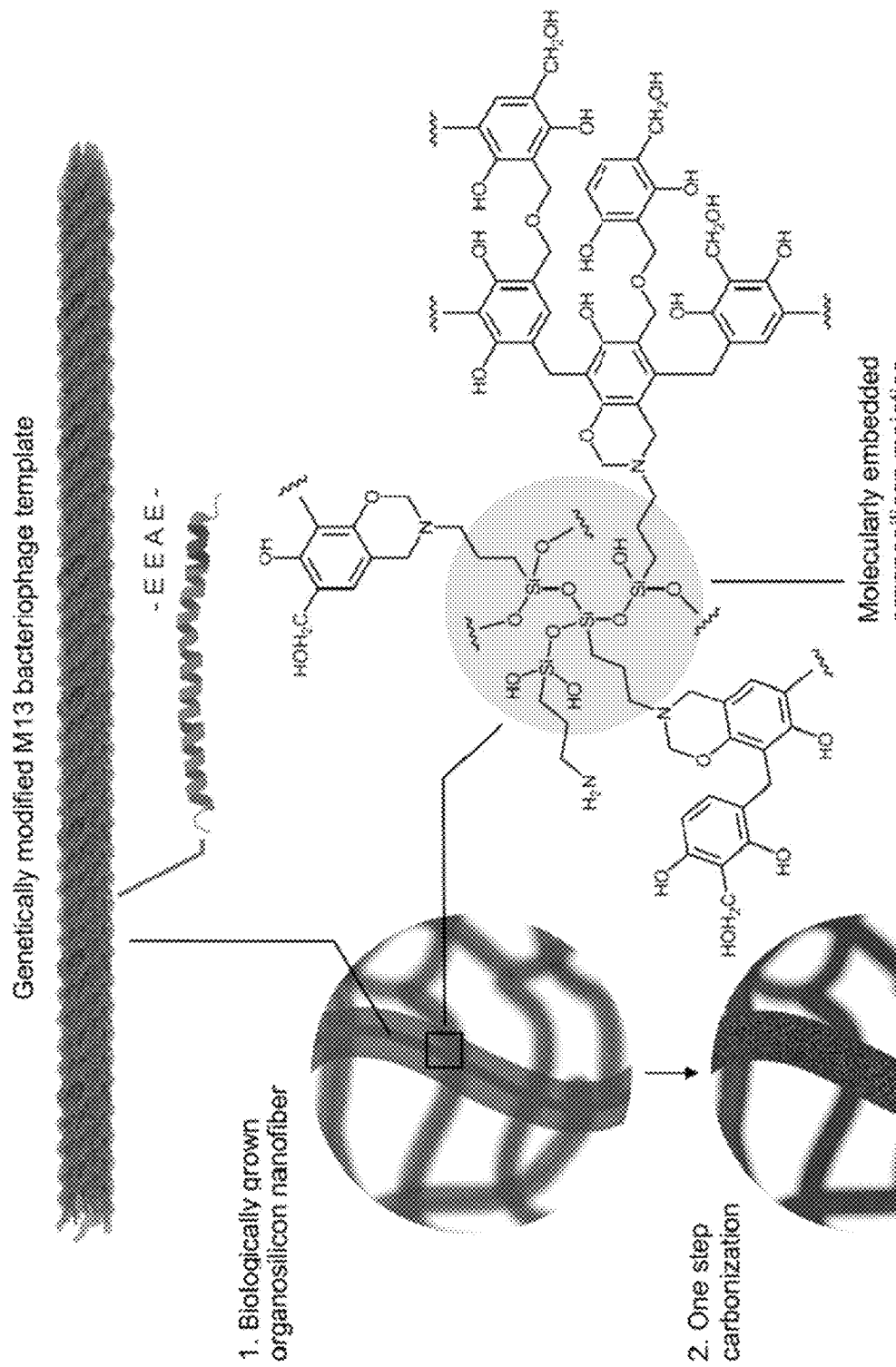
FIG. 1A is a schematic showing the process for synthesizing biotemplated carbon nanofibers.

Nature has imparted biological organisms the ability to build exquisite structures by genetically controlling material assembly at the nanoscale. See Chung, W. J. et al. Biomimetic self-templating supramolecular structures. *Nature* 478, 364-368 (2011), which is incorporated by reference in its entirety. There is now tremendous interest in mimicking this process to synthesize nanomaterials with more intricate structures at increasingly smaller length-scales. To this end, the M13 bacteriophage has been recognized as a versatile template due to its morphology, genetic tunability and safety. See Mao, C. Virus-Based Toolkit for the Directed Synthesis of Magnetic and Semiconducting Nanowires. *Science* (80-). 303, 213-217 (2004), and October, C. et al. Virus-Enabled Synthesis and Assembly Battery Electrodes. *Science* (80-). 312, 885-889 (2008), each of which is incorporated by reference in its entirety. This bacteriophage has a filamentous structure with a diameter of ~6.5 nm and length ~880 nm (aspect ratio ~135) that is very similar to important nanomaterials such as carbon nanotubes, thus making it ideally suited for templating similar 1-dimensional materials. The majority of its viral capsid is comprised of 2700 copies of helically assembled p8 proteins which can be easily modified using either phage or phagemid vectors. See Hess, G. T. et al. M13 Bacteriophage Display Framework That Allows Sortase-Mediated Modification of Surface-Accessible Phage Proteins. (2012), which is incorporated by reference in its entirety. Furthermore, because the M13 bacteriophage is naturally occurring and shows no infectivity towards eukaryotic cells, it presents minimal health risks and its application is therefore not limited to the laboratory. See Verheust, C., Pauwels, K., Mahillon, J., Helinski, D. R. & Herman, P. Contained Use of Bacteriophages: Risk Assessment and Biosafety Recommendations. 15, (2010), which is incorporated by reference in its entirety. The M13 bacteriophage has already been used to synthesize a wide range of inorganic materials, such as oxides, dichalcogenides and metals. See Lee, Y. J. et al. Virus-templated Au and Au—Pt core-shell nanowires and their electrocatalytic activities for fuel cell applications. *Energy Environ. Sci.* 5, 8328 (2012), Lee, J. H. et al. Production of tunable nanomaterials using hierarchically assembled bacteriophages. *Nat. Protoc.* 12, 1999-2013 (2017), Manivannan, S. et al. M13 Virus-Incorporated Biotemplates on Electrode Surfaces to Nucleate Metal Nanostructures by Electrodeposition. *ACS Appl. Mater. Interfaces* 9, 32965-32976 (2017), Limo, M. J., Ramasamy, R. & Perry, C. C. ZnO binding peptides: Smart versatile tools for controlled modification of ZnO growth mechanism and morphology. *Chem. Mater.* 27, 1950-1960 (2015), and Emami, F. S. et al. Prediction of specific biomolecule adsorption on silica surfaces as a function of pH and particle size. *Chem. Mater.* 26, 5725-5734 (2014), each of which is incorporated by reference in its entirety. However, there are few existing examples of biotemplated organic or carbonaceous materials, even though these have tremendous technological importance. Particularly, carbon nanofibers with their combination of high surface area, electrical conductivity and chemical stability have been extensively used in a wide-range of applications. See Shi, Q., Liang, H., Feng, D., Wang, J. & Stucky, G. D. Porous Carbon and Carbon/Metal Oxide Microfibers with Well-Controlled Pore Structure and Interface. *J. Am. Chem. Soc.* 130, 5034-5035 (2008), and Inagaki, M., Yang, Y. & Kang, F. Carbon nanofibers prepared via electrospinning. *Adv. Mater.* 24, 2547-2566 (2012), each of which is incorporated by reference in its entirety.

A new type of carbon sorbent can enable broad-spectrum neutralization of chemical threats. To do this, a molecular-based design approach was taken in lieu of the activation-based methods traditionally used to prepare activated carbon. Using molecular-based design, the texture and microporosity of the carbon is capable of being controlled by the structure and composition of the organic precursor, rather than relying on chemical or physical activation processes after carbonization. This has been shown to significantly enhance control over the carbon texture, surface properties, and size and uniformity of the micropores. See, e.g., Liu, J., Wickramaratne, N. P., Qiao, S. Z. & Jaroniec, M. Molecular-based design and emerging applications of nanoporous carbon spheres. *Nat. Mater.* 14, 763-774 (2015); Chen, W. et al. High-flux water desalination with interfacial salt sieving effect in nanoporous carbon composite membranes. *Nat. Nanotechnol.* (2016). doi:arXiv:1604.07567; Zhao, D., Yu, C., Fan, J., Tian, B. & Stucky, G. D. High-yield synthesis of periodic mesoporous silica rods and their replication to mesoporous carbon rods. *Adv. Mater.* 14, 1742-1745 (2002). The organic precursor used in this work was based on resorcinol-formaldehyde (RF) resin. This type of resin is used extensively as the precursor to carbon mesostructures such as carbon spheres, aerogels and xerogels, and is readily synthesized by the addition-condensation polymerization of resorcinol and formaldehyde. See, e.g., Horikawa, T., Hayashi, J. & Muroyama, K. Size control and characterization of spherical carbon aerogel particles from resorcinol-formaldehyde resin. *Carbon N. Y.* 42, 169-175 (2004), which is incorporated by reference herein. During this reaction, polysiloxane moieties can be simultaneously incorporated into the resin by introducing 3-aminopropyltrimethoxysilane (APTMS) as co-precursor and exploiting the Mannich condensation reaction of APTMS (at the primary amine) with resorcinol and formaldehyde. See, e.g., Elkhatat, A. M. & Al-Muhtaseb, S. A. Advances in tailoring resorcinol-formaldehyde organic and carbon gels. *Adv. Mater.* 23, 2887-2903 (2011), which is incorporated by reference herein. The polysiloxane moieties act as molecular templates during carbonization, introducing oxygen species, and creating a substantial number of intrinsic defects and consequentially, microporosity.

In this work, molecular-based design was coupled with biotemplating to give the carbon material higher order structure. Biotemplating is a method of making materials by using biological surfaces to guide the growth of materials, in a way, mimicking how nature assembles material using protein-based interactions. See, e.g., Chung, W. J. et al. Biomimetic self-templating supramolecular structures, *Nature* 478, 364-368 (2011); Lee, J. H. et al. Production of tunable nanomaterials using hierarchically assembled bacteriophages. *Nat. Protoc.* 12, 1999-2013 (2017), which are incorporated by reference herein. By using biotemplating to control the morphology of the organic precursor, one can simultaneously control the structure of the material across multiple length-scales. The M13 bacteriophage were used as the biotemplate because of its shape, genetic tunability and safety. See, e.g., Mao, C. Virus-Based Toolkit for the Directed Synthesis of Magnetic and Semiconducting Nanowires. *Science* (80-). 303, 213-217 (2004), which is incorporated by reference herein. The M13 bacteriophage is a filamentous virus with a diameter of ~6.5 nm and length of ~880 nm. It has already been used to template many inorganic materials of technological importance such as oxides, dichalcogenides and metals. See, e.g., Manivannan, S. et al. M13 Virus-Incorporated Biotemplates on Electrode Surfaces to Nucleate Metal Nanostructures by Electrodeposition. *ACS Appl. Mater. Interfaces* 9, 32965-32976 (2017), which is incorporated by reference herein. The protein coat of the virus was genetically modified so that RF resin would precipitate exclusively on its surface and form a network of nanofibers. These nanofibers could then be directly carbonized to form carbon nanofibers. This process is shown schematically in FIG. 1A. These biotemplated carbon nanofibers (BioCNF) demonstrated exceptional capacities for removing a broad range of chemical threats, including CWAs, TICs and micropollutants, that far exceeded the capacities achievable using commercial activated carbons. The enhanced capacities were attributed in part to the high density of intrinsic defects and abundance of oxygen groups generated by our synthetic approach, which acted as both adsorptive and reactive sites.

Figure 1B:
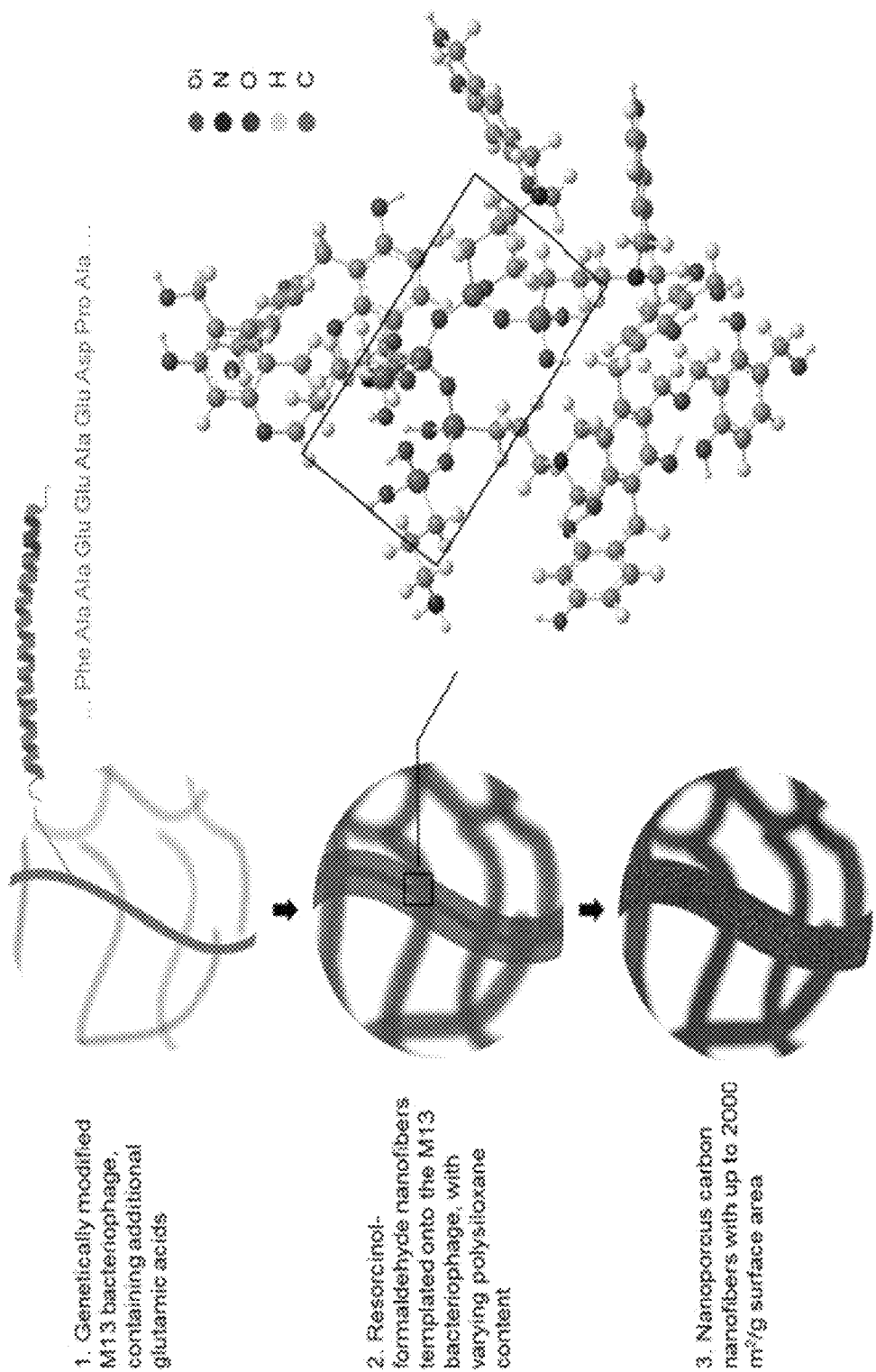
FIG. 1B is a schematic showing a synthesis process with nanofibers directly carbonized to form biotemplated carbon nanofibers.

Referring to FIG. 1B, in this example, M13, bacteriophage genetically modified with an EEAE amino acid insert on the p8 protein was used as the template (1). The M13 bacteriophage was incubated with an aqueous solution of resorcinol, formaldehyde and APTMS in a specified ratio at 80° C. overnight, with no catalysis and under no mechanical agitation. The resorcinol-formaldehyde nanofibers thus formed (2) contained a mixture of organic and inorganic (polysiloxane) moieties, with the proposed molecular structure shown on the right. Carbonization of the resorcinol-formaldehyde nanofibers at 1100° C. followed up etching in sodium hydroxide solution at 80° C. yielded highly uniform carbon nanofibers (3). The surface area and chemical functionalization on these carbon nanofibers was controlled by the initial precursor composition.

Figure 19:
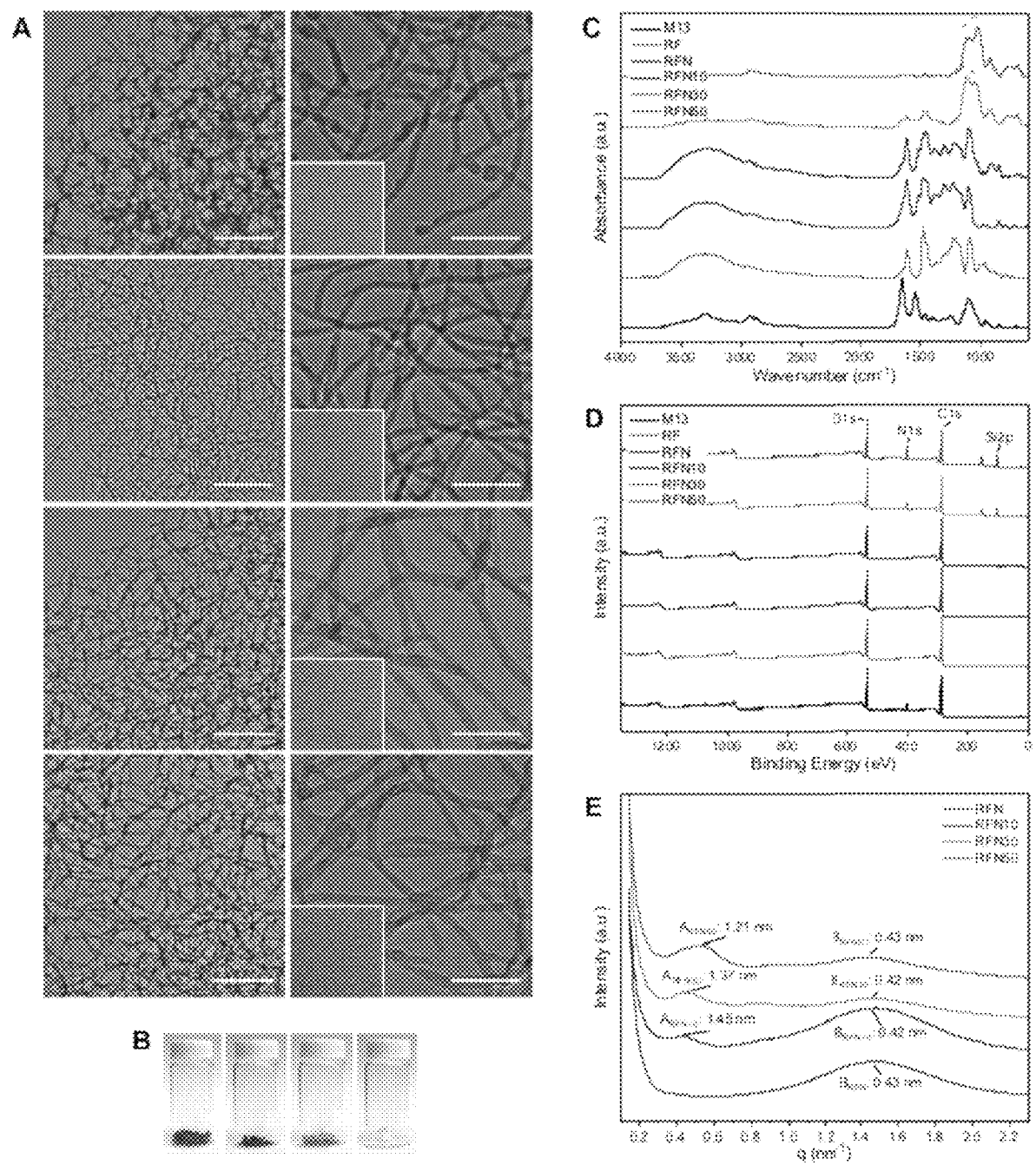
FIG. 19 shows a characterization of biotemplated resorcinol-formaldehyde nanofibers with different chemical compositions.

Referring to FIG. 19, the spectra for M13 bacteriophage and pure resorcinol-formaldehyde resin are also shown for comparison. Doublet FTIR peaks corresponding polysiloxane moieties are highlighted (♦). Intensity-wave vector plots from WAXS analysis (E) for resorcinol-formaldehyde nanofibers show a scattering feature corresponding to 0.42~0.43 nm for all samples (peak B). The scattering peak at 1.21~1.45 nm was only present in samples containing polysiloxane (peak A). The peak intensity ratio increased with increasing polysiloxane content: 0.03, 0.22 and 0.32 for RFN10, RFN30 and RFN50, respectively.

Figure 20:
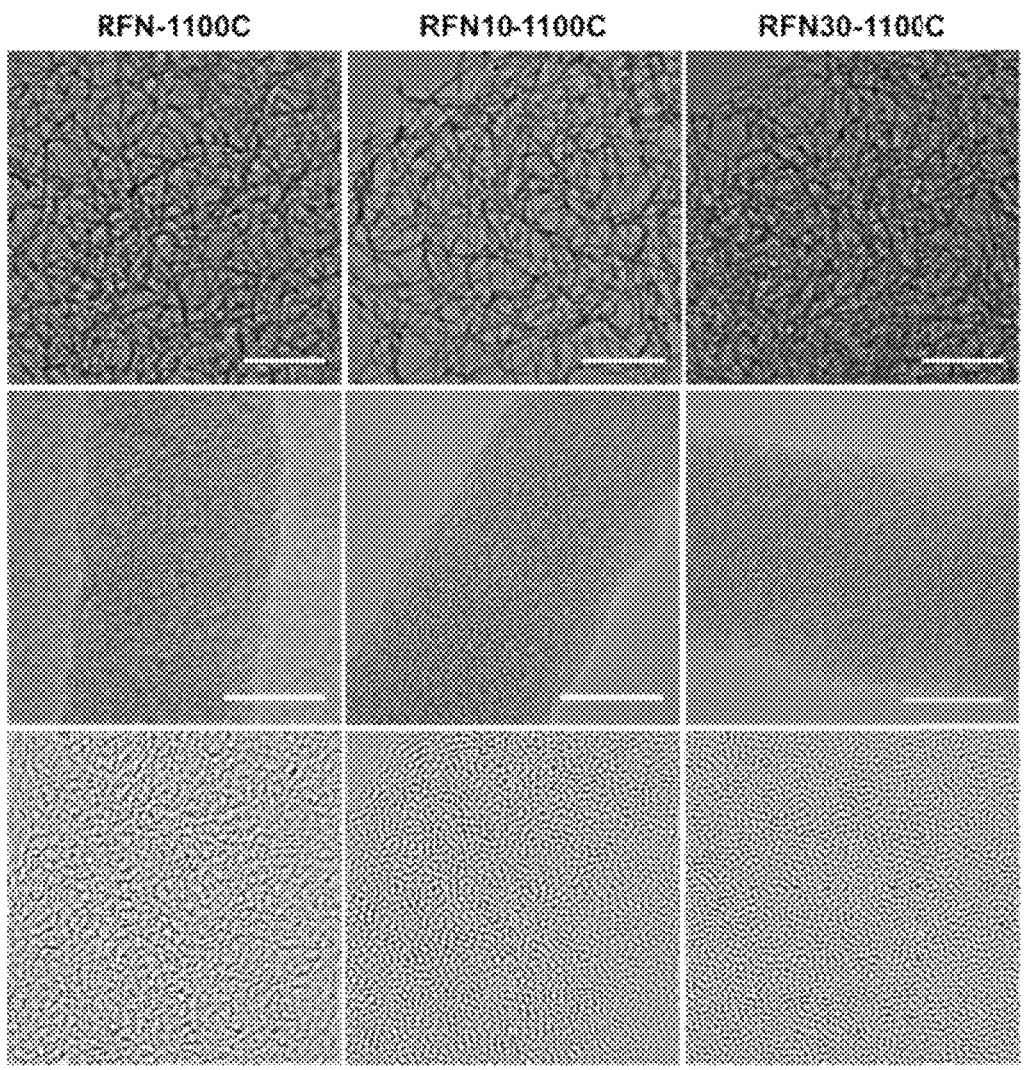
FIG. 20 shows images of resorcinol-formaldehyde nanofibers after carbonization. Uniform nanofibers of similar morphology were observed for all samples RFN, RFN10 and RFN30 (from left to right).
Figure 38:
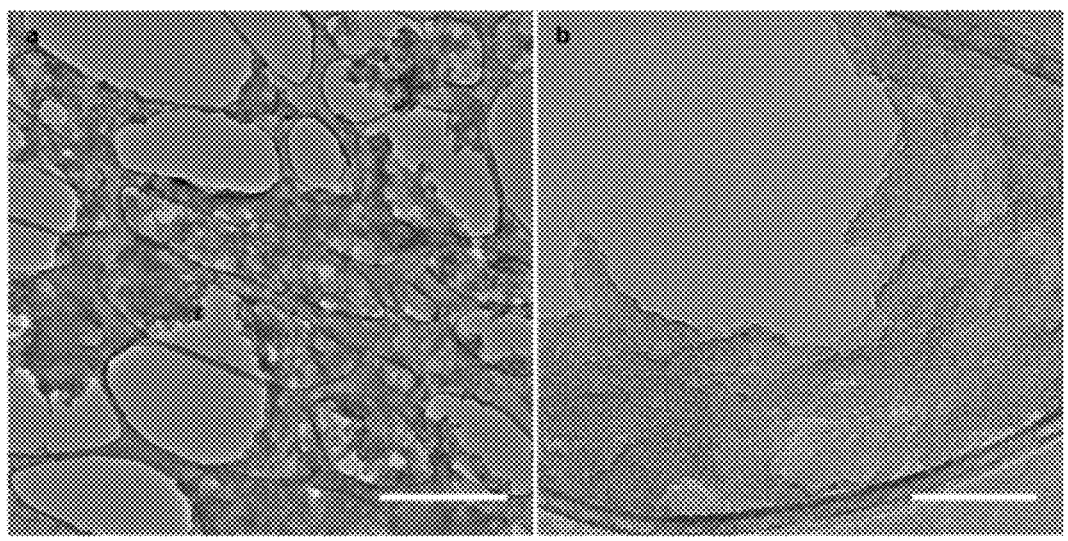
FIG. 38 shows RFN50 after carbonization at 800° C. and etching. Scale bars: (a) 1 μm and (b) 100 nm.
Figure 39:
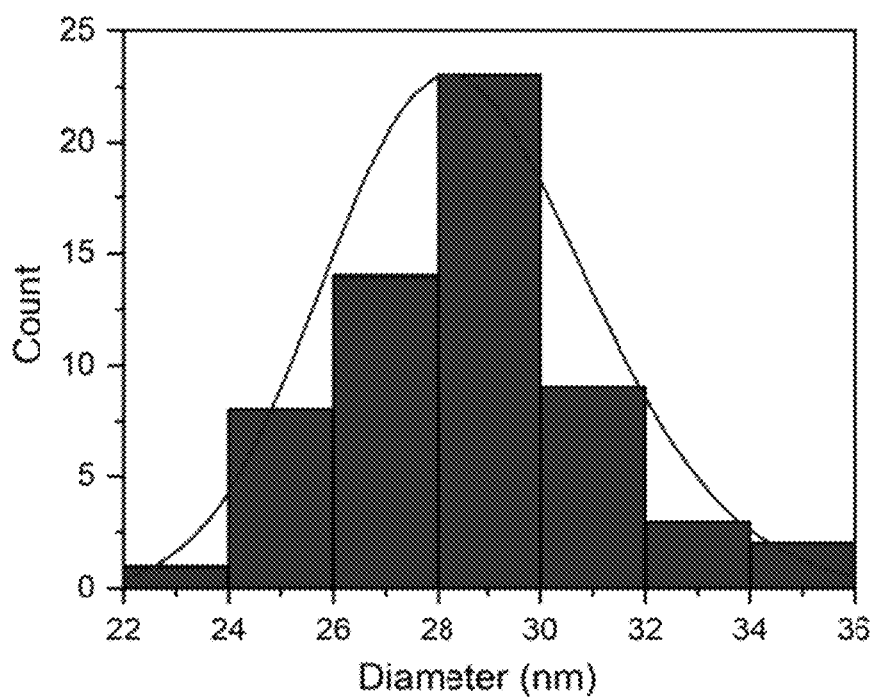
FIG. 39 shows a histogram of the distribution of RFN-1100C diameters (sample size 60). Average diameter is 28.6 nm with a standard deviation of 2.6 nm.
Figure 40:
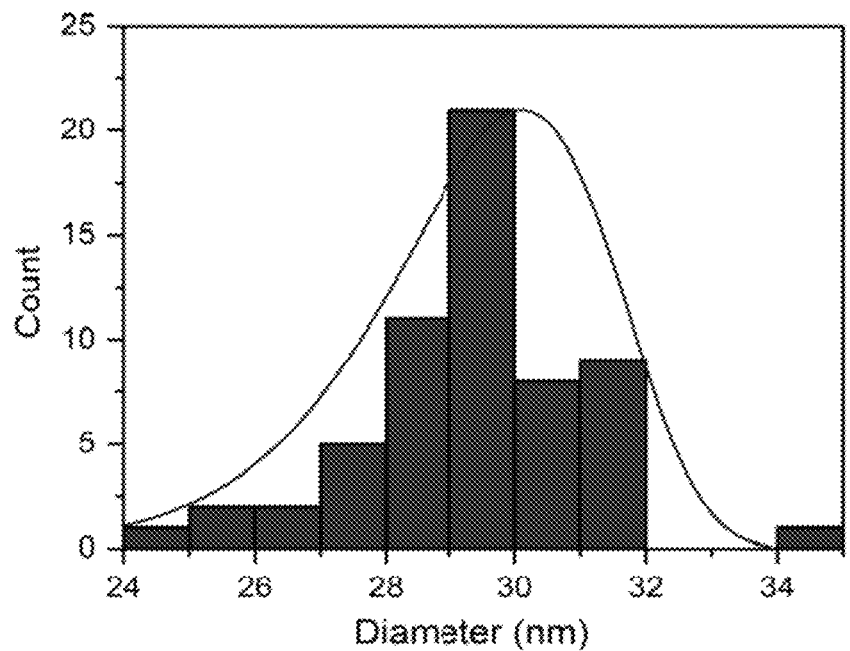
FIG. 40 shows a histogram of the distribution of RFN10-1100C diameters (sample size 60). Average diameter is 29.4 nm with a standard deviation of 1.7 nm.
Figure 41:
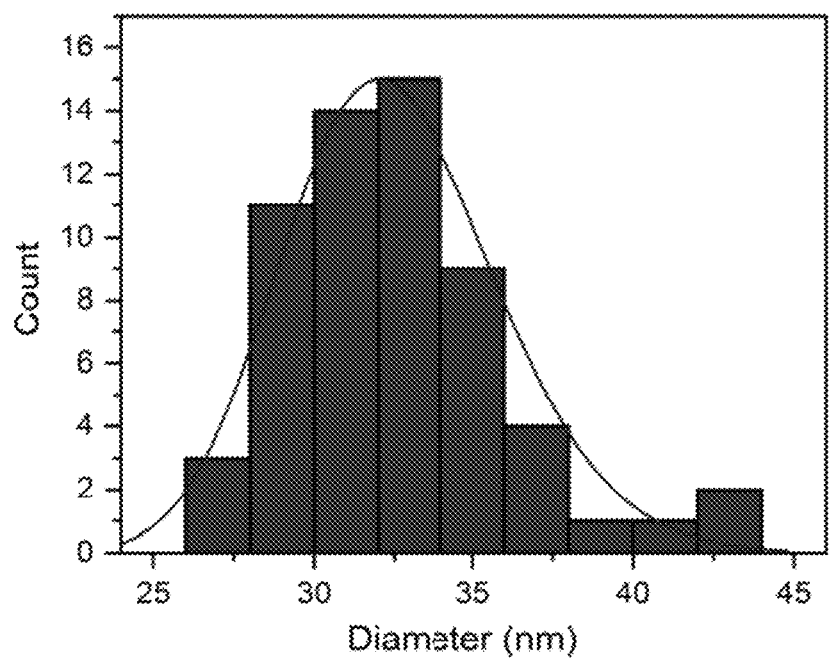
FIG. 41 shows a histogram of the distribution of RFN30-1100C diameters (sample size 60). Average diameter is 32.5 nm with a standard deviation of 3.5 nm.

All four RF nanofiber samples were then carbonized in Argon at 1100° C. then mildly etched in warm sodium hydroxide solution (FIG. 20). Apart from RFN50, which did not contain enough organic content (FIG. 38), the three other samples formed networks of carbon nanofibers that maintained the morphology of their starting resins. The nanofiber diameters were between 28 and 38 nm (FIG. 39, FIG. 40 and FIG. 41). Radial shrinkage during carbonization was minimal (under 10% for both RFN10 and RFN30). The carbon texture between the samples were significantly different across these samples (FIG. 20). Carbonized RFN (RFN-1100C) had a glassy, but partially turbostratic texture that is characteristic of carbons derived from phenolic resins. See, e.g., Inagaki, M., Kang, F., Toyoda, M. & Konno, H. Chapter 6—Glass-like Carbon: Its Activation and Graphitization. *Adv. Mater. Sci. Eng. Carbon* 3, 111-132 (2014), which is incorporated by reference herein. Contrastingly, carbon nanofibers derived from RFN10 and RFN30 (RFN10-1100C and RFN30-1100C) were highly amorphous, and almost no local graphitic stacking could be resolved under HRTEM.

Referring to FIG. 20, The average diameters are 28.6 nm, 29.4 nm and 37.9 nm, respectively. Scale bars: (top row) 500 nm and (middle row) 15 nm. High resolution images were post-processed using FFT to resolve the turbostratic texture of RFN derived carbon and the highly amorphous texture of carbon derived from RFN10 and RFN30 (bottom row).

Figure 42:
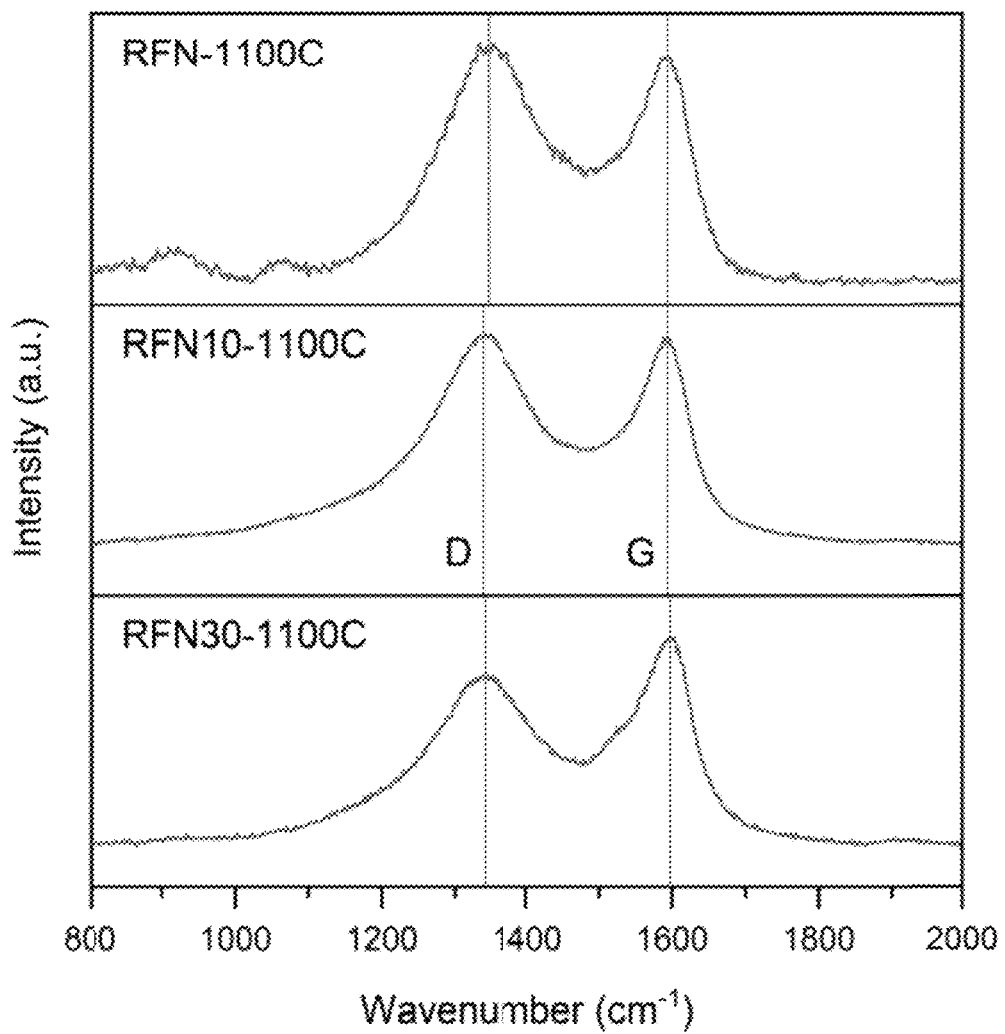
FIG. 42 shows Raman spectra for RFN, RFN10 and RFN30 carbonized at 1100° C. The positions of the D and G bands are labeled.
Figure 43:
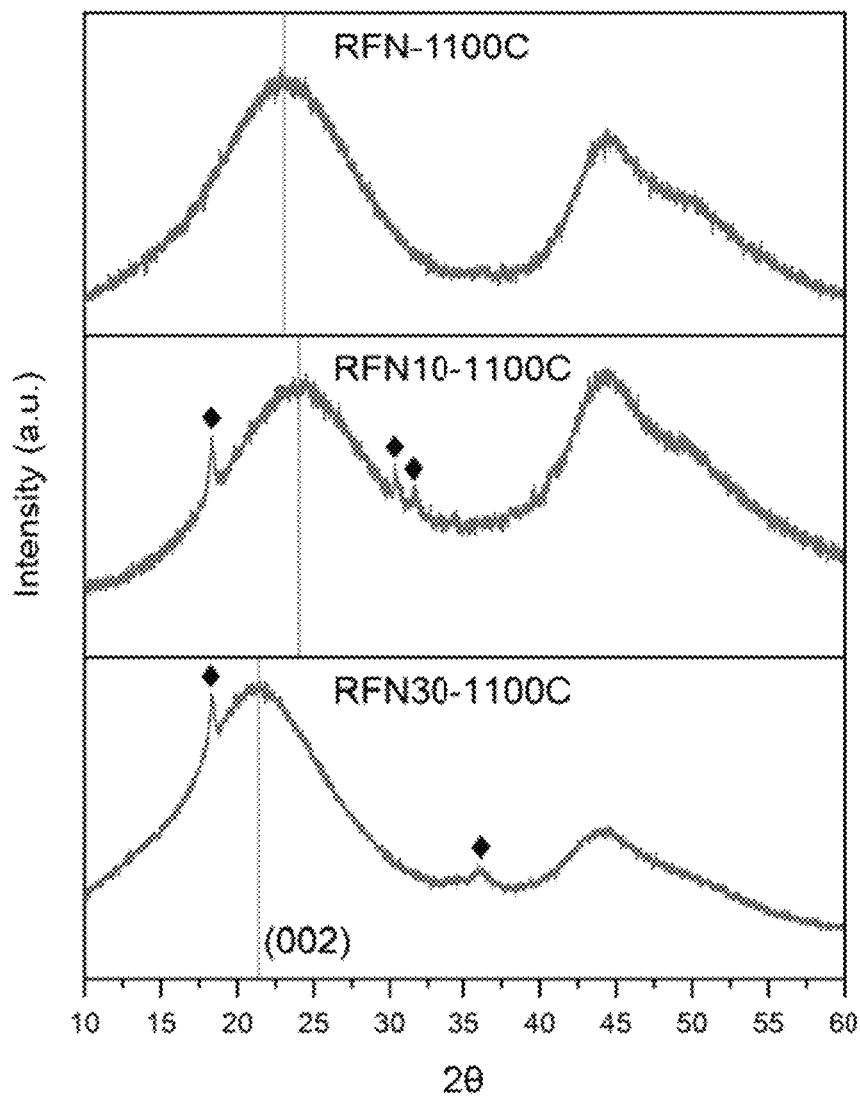
FIG. 43 shows XRD diffractograms of RFN, RFN10 and RFN30 carbonized at 1100° C. The broad peak at ~23° is attributed to (002) planes. Some small peaks were observed (♦), but their origins were unclear.

To further understand the effect of polysiloxane on carbon texture, each sample was probed using Raman spectroscopy and x-ray diffractometry (XRD). See, e.g., Dresselhaus, M. S. et al. New characterization techniques for activated carbon fibers. *Carbon N. Y.* 30, 1065-1073 (1992), which is incorporated by reference herein. Each Raman spectrum comprised of two major peaks associated with the G mode (1590~1600 $cm^{-1}$) and D mode (~1350 $cm^{-1}$) vibrations (FIG. 42). The in-plane crystallite size ($L_a$) was estimated with the D/G peak intensity ratio ($I_D/I_G$) using the Tuinstra-Koenig correlation for the turbostratic sample RFN-1100C, and the Ferrari-Robertson correlation for the amorphous samples RFN10-1100C and RFN30-1100C (Supplementary Table 4). See, e.g., Ferrari, A. C. & Robertson, J. Interpretation of Raman spectra of disordered and amorphous carbon. *Phys. Rev. B* 61, 95-107 (2000). Crystallite size decreased with increasing precursor polysiloxane content.n XRD was used to study the inter-planar stacking distance and disorder (FIG. 43). The peak at ~23° was attributed to diffraction at (002) planes and yielded the interlayer spacing, $d_{002}$. The larger inter-planar spacing seen in RFN30-1100C reflected more pronounced stacking irregularities and higher levels of intrinsic defects, such as edges and vacancies. This was in agreement with the smaller crystallite size and significantly lower electrical conductivity measured for this sample (Supplementary Table 4). See, e.g., Li, Z. Q., Lu, C. J., Xia, Z. P., Zhou, Y. & Luo, Z. X-ray diffraction patterns of graphite and turbostratic carbon. *Carbon N. Y.* 45, 1686-1695 (2007), which is incorporated by reference herein.

Figure 44:
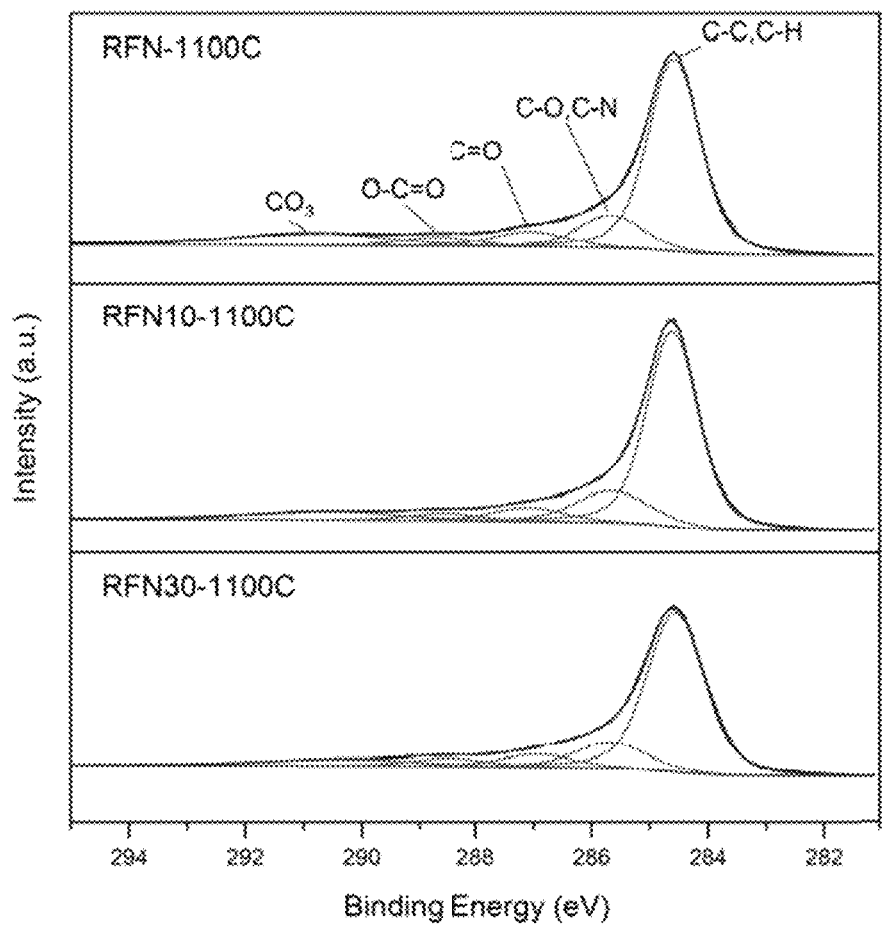
FIG. 44 shows high resolution C1s XPS spectra of RFN, RFN10 and RFN30 carbonized at 1100° C. The peaks were fitted to peaks corresponding to aliphatic carbon (C—C, C—H), carbon singly bonded to heteroatoms (C—O, C—N), carbonyl carbon (C=O), carboxyl carbon (O—C=O) and carbonic carbon ($CO_3$).

Surface area was measured using Brunauer-Emmett-Teller (BET) analysis (Supplementary Table 4). As expected based on crystallite size, RFN30-1100C exhibited the highest surface area of 1934 $m^2/g$, which was very high considering there was no further activation involved. Samples RFN-1100C and RFN10-1100C had surface areas of 365 $m^2/g$ and 776 $m^2/g$, respectively. The effect of carbonization temperature on surface area was investigated. Interestingly, the surface area of RFN30 after carbonization at 800° C. was lower at 1259 $m^2/g$. This was surprising because loss of surface area occurs for most types of carbons above 800~900° C. due to pore closure by partial crystallite alignment, so 800° C. is often considered the optimal temperature for maximizing surface area. See, e.g., Dresselhaus, M. S. et al. New characterization techniques for activated carbon fibers. *Carbon N. Y.* 30, 1065-1073 (1992), which is incorporated by reference herein. One likely explanation was that polysiloxane moieties acted as molecular templates during carbonization, which disrupted graphitic crystallite alignment, and thus promoted the formation of defects and microporosity. See, e.g., Inagaki, M., Kang, F., Toyoda, M. & Konno, H. Chapter 6—Glass-like Carbon: Its Activation and Graphitization. *Adv. Mater. Sci. Eng. Carbon* 3, 111-132 (2014), which is incorporated by reference herein. Further increasing carbonization temperature to 1400° C., however, resulted in a much lower surface area of 782 $m^2/g$. This was attributed to the carbothermic reduction of silicon dioxide clusters and the formation silicon carbide. See, e.g., Martin, H.-P., Ecke, R. & Müller, E. Synthesis of nanocrystalline silicon carbide powder by carbothermal reduction. *J. Eur. Ceram. Soc.* 18, 1737-1742 (1998), which is incorporated by reference herein. Based on XPS, RFN30-1100C also contained the highest oxygen content of 9.5 at. %. This high oxygen content likely originated from the out-diffusion of oxygen species from polysiloxane during carbonization (FIG. 44 and Supplementary Table 5). See, e.g., Dresselhaus, M. S. et al. New characterization techniques for activated carbon fibers. *Carbon N. Y.* 30, 1065-1073 (1992), which is incorporated by reference herein. Sample RFN30-1100C was used for all subsequent adsorption studies due to its combination of high surface area and oxygen content.

Disclosed herein are the synthesis and application of microporous carbon nanofibers, beginning with the synthesis of the organic nanofiber precursor. In certain embodiments, the precursor to the carbon nanofiber can be an organosilicon nanofiber containing a bacteriophage core. After the precursor is carbonized, the bacteriophage is also carbonized and the silicon moieties are washed/etched out. In certain embodiments, carbon nanofibers can also be prepared by using resorcinol-formaldehyde with ethylenediamine crosslinking to produce nanofibers with less microporosity.

This synthesis method couples the use of biological and molecular templating to directly produce high surface area (~2000 $m^2/g$) carbon nanofibers without need for post-processing and activation required of existing methods. This method allows to access dimensions (~20 nm) that are exceedingly difficult with other approaches. Using very simple adjustments to the reaction condition, 3-dimensional self-assembly can be induced.

In general, a composition can include a carbon nanofiber, wherein a precursor for the carbon nanofiber includes an alcohol and an aldehyde crosslinked by a primary amine. In certain embodiments, carbon nanofibers can be biotemplated. This method combines templating at two different length scales (molecular+nanometer morphology) to produce carbon nanofibers that are difficult to access otherwise. Biological templating enables precise control of morphology at the nanometer scale, while molecular templating allows control of carbon nanotexture and structure at the sub-nanometer scale. In certain embodiments, molecular templating can be achieved by modifying the resorcinol-formaldehyde precursor with organosilicon moieties. In certain embodiments, nanometer morphology can be achieved by using a template. In certain embodiments, M13 bacteriophage can be used as a template. In certain embodiments, M13 bacteriophage can be genetically modified. In certain embodiments, M13 bacteriophage can be genetically unmodified. In certain other embodiments, carbon nanotubes or iron oxide nanoparticles can be used as a template.

Described herein, "nanotexture" of the carbon nanofiber includes the disorder and bonding state of carbon atom ($\pi$-electron delocalization) at the molecular level, and the graphitic crystallite size (in-plane $L_a$ and inter-planar $L_c$) and order (interlayer spacing, stacking) at the microstructural level. The nanotexture of the carbon directly determines material properties such as surface area and electrical conductivity. Carbon nanotexture can be controlled by introducing a molecular template to constrain the carbonization process.

In certain embodiments, M13 bacteriophage can be used to synthesize ultrafine carbon nanofibers with simultaneous control over structure and self-assembly. In certain embodiments, the p8 protein of the M13 bacteriophage can be modified by inserting an EEAE peptide moiety. Genetically inserting an EEAE sequence improves the uniformity of the nanofibers. The synthesis then involved a two-step process of (1) templating an organosilicon-modified resorcinol-formaldehyde nanofiber and (2) carbonization. The molecular structure of the resorcinol-formaldehyde nanofiber is shown in FIG. 1.

Carbon nanofibers synthesized in this way can have hierarchical pore distribution with micropores smaller than 2 nm and macropores bigger than 100 nm. In certain embodiments, carbon nanofibers can have micropores smaller than 20 nm. Surface area of the carbon nanofibers can be tuned in the range of 200 $m^2/g$ to 2000 $m^2/g$. In certain embodiments, the synthesis of highly uniform carbon nanofibers with ~20 nm diameter and ~2000 $m^2/g$ surface area is possible without activation. The combination of ultrafine dimensions and high microporosity is ideal for application as a rapid adsorbent. In certain embodiments, the carbon nanofibers can be used as a rapid adsorbent for environmental remediation and gastric decontamination. In certain embodiments, the carbon nanofibers can be used as a rapid adsorbent for small molecules (e.g. phenolic compounds), pharmaceutics, heavy ions (e.g. $Pb^{2+}$, $Sr^{2+}$), organophosphates (e.g. pesticides, insecticides), chemical warfare agents (e.g. sarin gas, mustard gas), organic dyes, gases (carbon dioxides, methane). Rapid adsorption is related to the adsorption kinetics, which is up to 30 times faster than activated charcoal. The adsorption rate was almost instantaneous in some cases. Rapid adsorption is particularly important for detoxication in cases of drug overdose. For industrial dye removal, a methylene blue uptake of 902 mg/g was amongst the highest values recorded. For medical applications such as the treatment of drug overdose, a 30× improvement in the adsorption rate of propranolol was recorded over commercial charcoal. Further, the incorporation of an ultrathin ~5 µm carbon nanofiber interlayer in lithium-sulfur batteries can improve reversible capacity by 70%.

Here, by coupling biological and molecular templating, it is possible to synthesize ultrafine carbon nanofibers with exact precision and control over the nanotexture, morphology and self-assembly. Using this virus-based approach, highly uniform, microporous carbon nanofibers with diameters less than 20 nm could be synthesized, achieving a level precision that is exceedingly difficult to access using conventional methods such as electrospinning. See Inagaki, M., Yang, Y. & Kang, F. Carbon nanofibers prepared via electrospinning. *Adv. Mater.* 24, 2547-2566 (2012), and Rahaman, M. S. A., Ismail, A. F. & Mustafa, A. A review of heat treatment on polyacrylonitrile fiber. *Polym. Degrad. Stab.* 92, 1421-1432 (2007), each of which is incorporated by reference in its entirety. Furthermore, the option to integrate molecular templating allowed the carbon nanotexture to be tuned, introducing up to 2000 $m^2/g$ surface area without activation. The ability to tune structure and properties at multiple length-scales allowed these materials to be used in applications such as rapid adsorption and energy storage. Rapid adsorption of pharmaceutics is critical to detoxication during drug overdose, and biotemplated carbon nanofibers can remove pharmaceutics 30 times faster than commercial adsorbents. In another example, it is possible to improve the reversible capacity of lithium-sulfur batteries by up to 70% by inserting an ultrathin interlayer of biotemplated carbon nanofibers.

Experimental Methods

Resorcinol-Formaldehyde Synthesis.

Concentrated precursor solutions were freshly prepared immediately before synthesis according to Supplementary Table 1. In a typical large-scale reaction, 2 L of virus suspension at a concentration of $3.2 \times 10^{11}$ pfu/mL was preheated to ~50° C. Precursor solutions were then added to the virus suspension under vigorous stirring. The volume of precursors added depended on the final polysiloxane content and was adjusted according to Supplementary Table 2. After thorough mixing of precursors, the suspension was transferred to an oven and incubated at 80° C. overnight. After the reaction, nanofiber precipitates were collected by filtering over a 0.2 µm membrane, and thoroughly rinsed with distilled water then lyophilized.

Carbon Nanofiber Synthesis.

The lyophilized nanofibers were carbonized at a set temperature (800° C., 1100° C. or 1400° C.) for at least 4 hours in flowing Argon, with a heating rate of 2° C./min. The carbonized nanofibers were then etched in 2 M sodium hydroxide at 80° C. overnight. After etching, the carbon nanofibers were thoroughly rinsed using distilled water over a 0.2 µm filter until the rinse water reached neutral pH, to indicate that all sodium hydroxide was removed.

Imaging.

Transmission electron microscopy (TEM) was carried out using the FEI Tecnai G2 and the JEOL 2010 High Resolution microscopes at 120 kV and 200 kV, respectively. The Image J software was used to process the images. To improve the clarity of carbon textures, images were with Fast Fourier Transform and the image brightness/contrast were adjusted. No further imaging processing was done. Scanning transmission electron microscopy (STEM) and energy dispersive x-ray spectroscopy (EDX) line-scans were carried out using the JEOL 2010F High Resolution at 200 kV.

Chemical/Surface Characterization.

Fourier-transform infrared spectroscopy (FTIR) was carried out using the Bruker Lumos FTIR in ATR mode. A background correction was used and $CO_2/H_2O$ peaks were corrected. X-ray electron spectroscopy (XPS) spectra were collected using the Thermo Scientific K-Alpha and Thermo Scientific K-Alpha+systems. An ion flood gun was used for all samples, and the peaks were charge corrected by setting the aliphatic C1s peak to 284.6 eV. All peaks were fitted using Voigt profiles (Gaussian:Lorentzian ratio 7:3). Raman spectra were obtained using the Horiba LabRam HR800 using a 532 nm light source.

Structural Characterization.

X-ray diffractometry (XRD) was carried out using the Panalytical X'Pert Pro Multipurpose Diffractometer. Data was collected in the Bragg-Brentano geometry between 10° and 60° 2θ using a copper anode, and using an automatic divergence slit. Wide-angle x-ray scattering (WAXS) experiments were conducted using the Rigaku H3R with Bruker Nanostar system. Samples were embedded in Kapton tape, and the Kapton tape background was subtracted after measurement.

Physical Characterization.

Brunauer-Emmett-Teller (BET) measurements were obtained using the Micromeritics ASAP 2020. Pore size distribution was determined using DFT calculations and micropore contributions were estimated using the t-plot method. Thermogravimetric analysis (TGA) and differential scanning calorimetry (DSC) were carried out using the TA Instruments Discovery systems. TGA thermograms were obtained under nitrogen, using a linear ramp mode (10° C./min) from 40° C. to 800° C. DSC was obtained using a linear ramp cycle from 40° C. to 300° C. and back.

Electrical Conductivity.

Electrical conductivity was measured for carbon nanofiber films. The films were made by mixing carbon with Teflon 8A in a 9:1 weight ratio using mortar and pestle, then rolled into films of thickness ≤100 μm. Because of the low density of the nanofiber powder, it was not possible to prepare the thin film sample of pure carbon. The 4-point probe sheet resistance was then measured using the Keithley SCS-4200 instrument with probe spacing of 1.27 mm, and resistivity calculated by:

$$\rho = 4.5324 t\left(\frac{v}{i}\right)$$

Where ρ is the resistivity in Ω·cm, t is the film thickness in cm, v/i is the voltage/current slope in V/A.

Synthesis and Characterization of Resorcinol-Formaldehyde Nanofibers

Figures 2A, 2B, 2C, 2D, 2E, 2F:
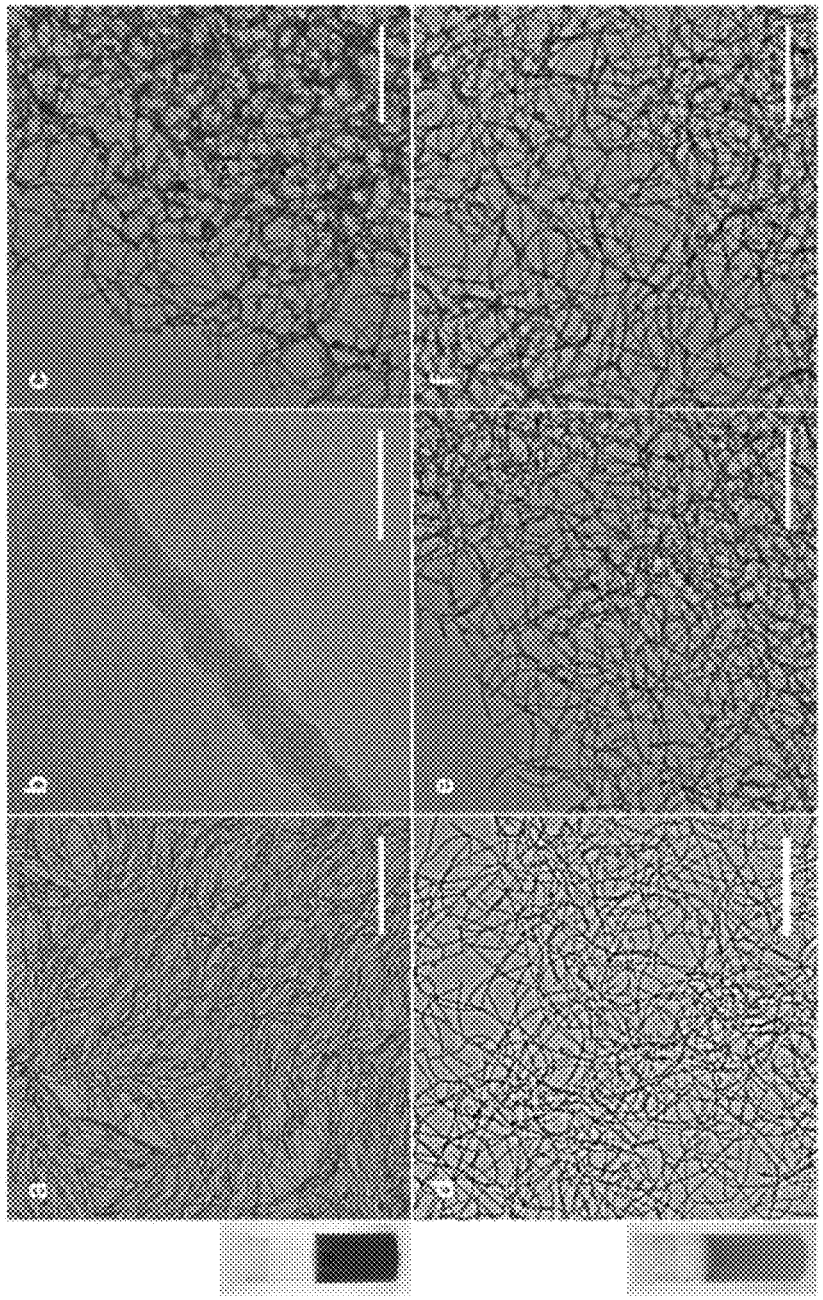
FIGS. 2A-2H show morphological and chemical characterization of biotemplated resorcinol-formaldehyde nanofibers. TEM micrographs of colloidally dispersed RFN10 is shown in FIGS. 2A and 2B. The photograph insert next to FIG. 2A shows colloidally stable RFN10 after at least 1 year storage. Ethylenediamine modified RF nanofibers (RFN) are shown in FIG. 2C; scale bar 1 μm ATPMS modified RF nanofibers (RFN10, RFN30 and RFN50) are shown FIGS. 2D, 2E and 2F in order. The photograph insert next to FIG. 2D shows as-synthesized RFN10 hydrogel. FTIR spectra and XPS survey spectra of the M13 bacteriophage, pure RF resin and all resorcinol-formaldehyde nanofibers are shown in FIGS. 2G and 2H, respectively.
Figure 2G:
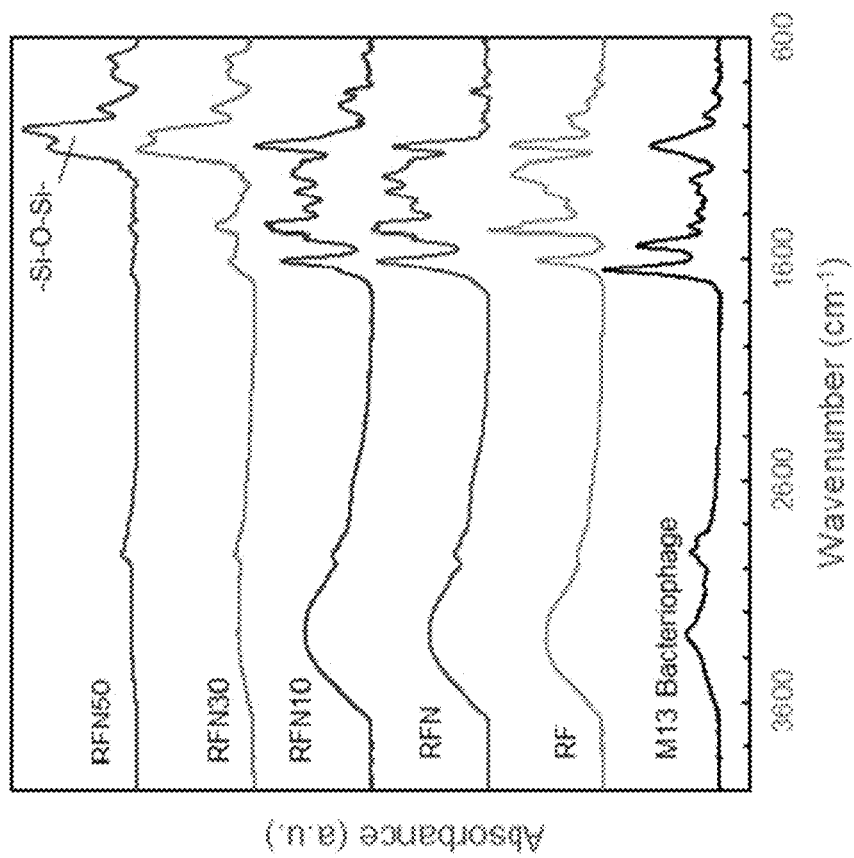
Figure 2H:
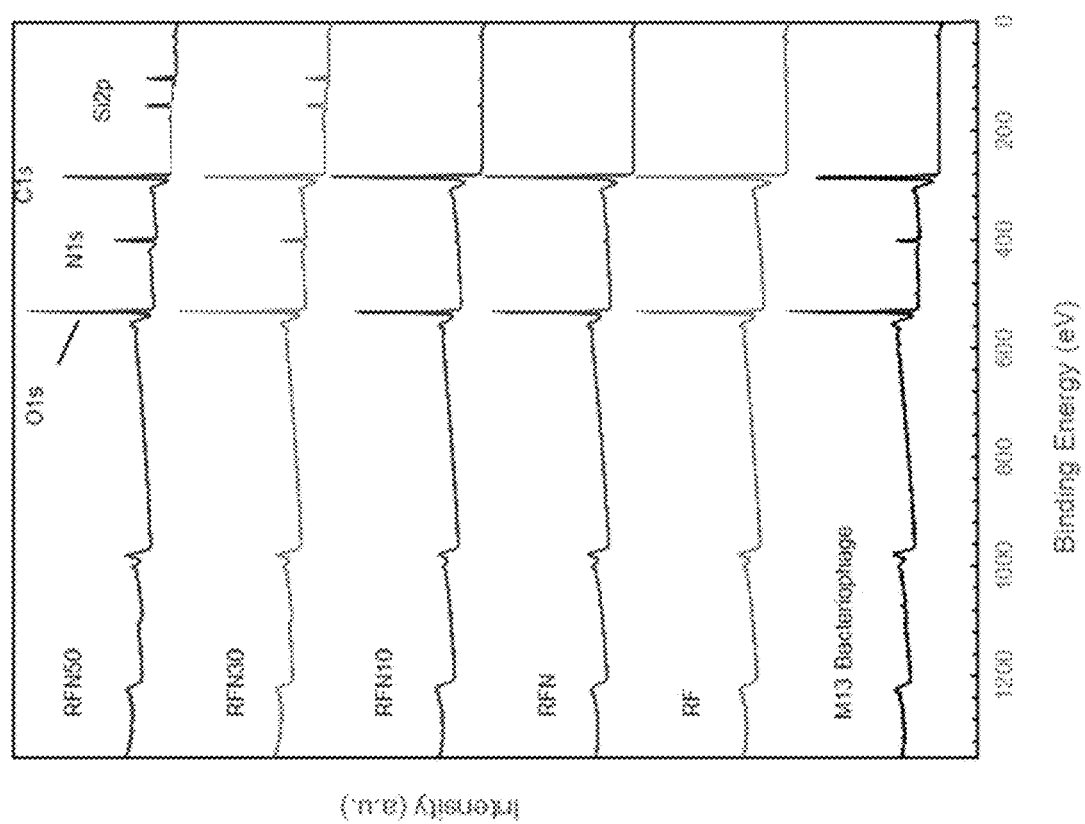
Figures 2I, 2J:
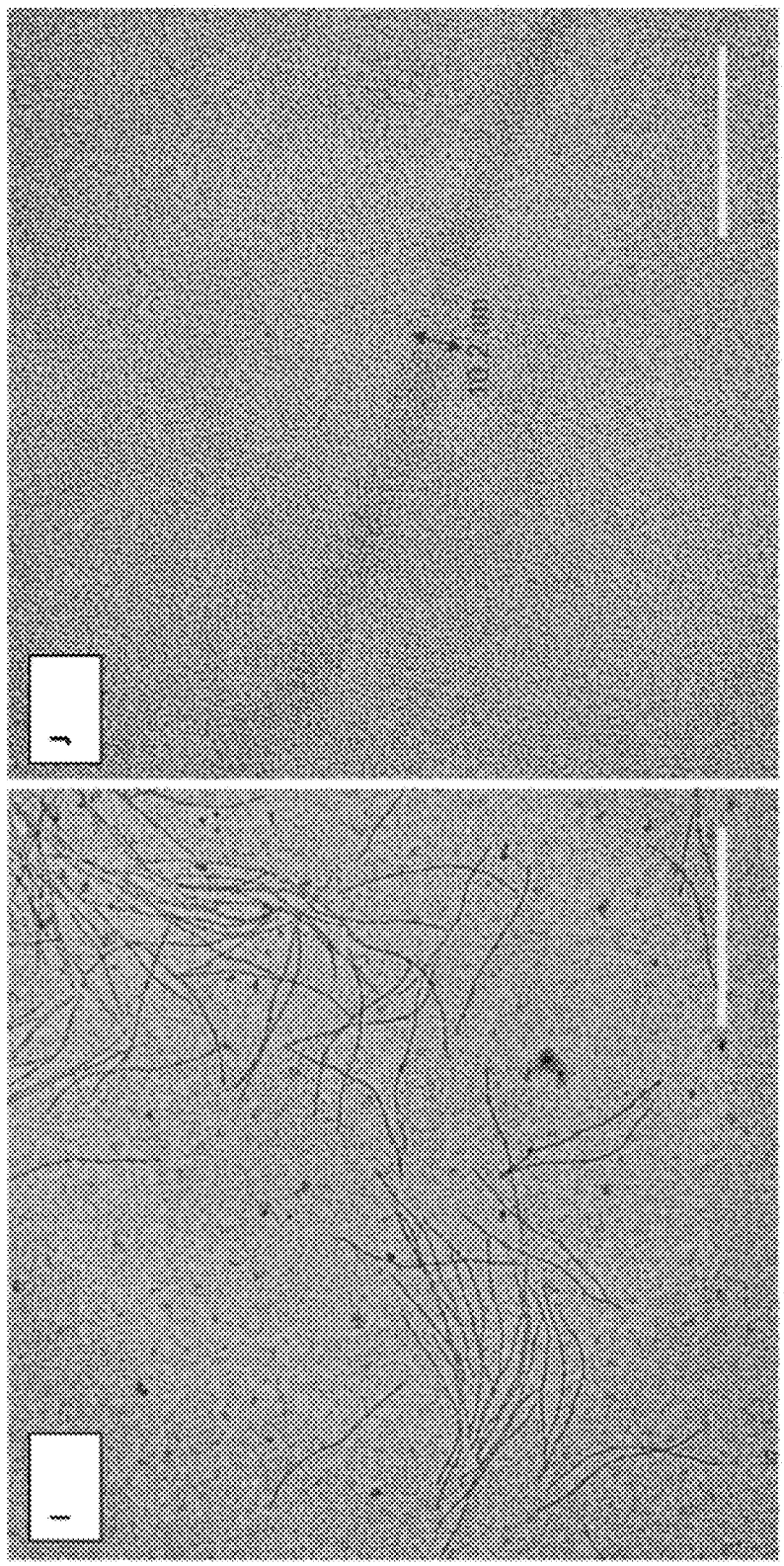
FIGS. 2I-2J show TEM micrographs of M13 bacteriophage.
Figure 6:
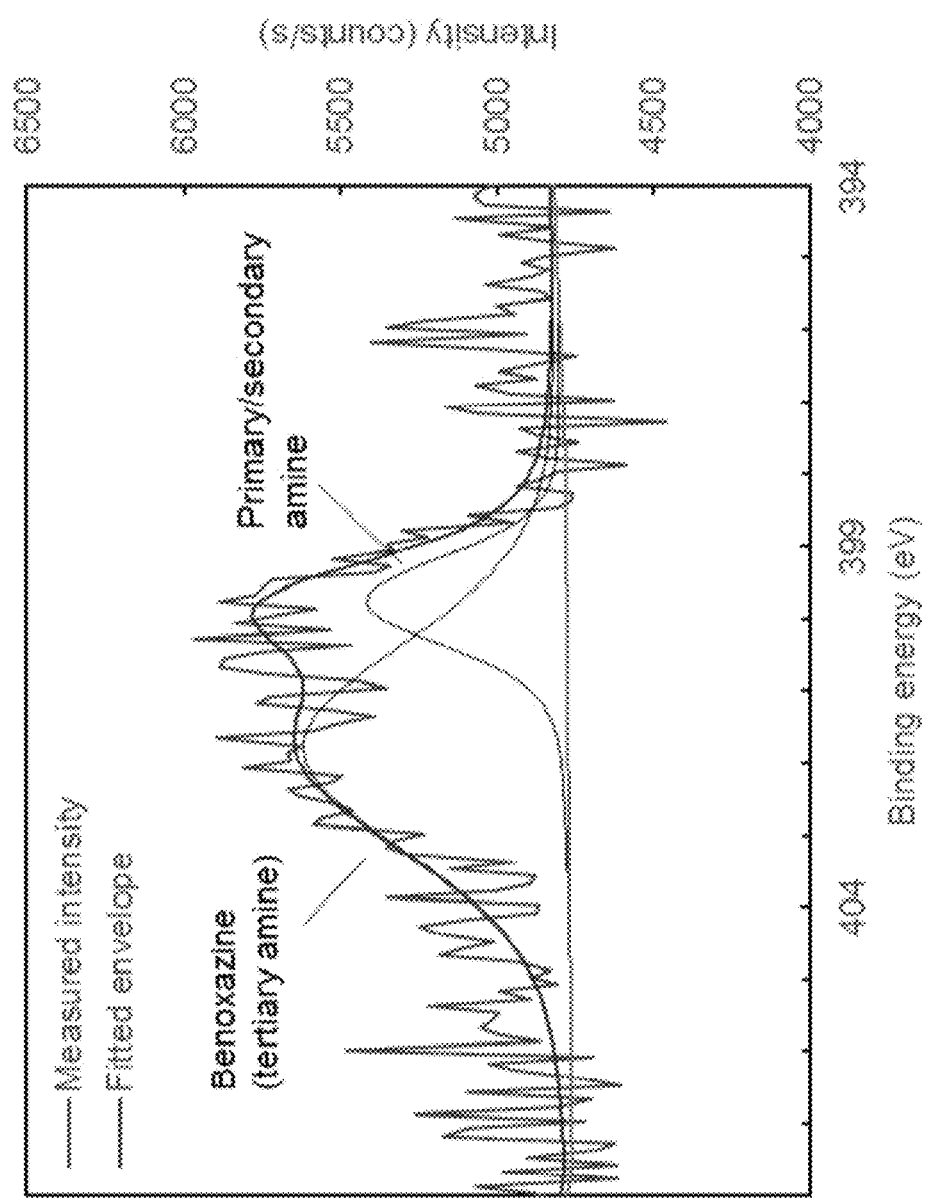
FIG. 6 shows high resolution XPS N1s spectrum of RFN.

There is significant interest in using resorcinol-formaldehyde (RF) resin as a carbon precursor due to its good char yield and its ability to form porous mesostructures. However, colloidal synthesis of RF resin is currently limited to 0-dimensional particles at the submicron scale. See Horikawa, T., Hayashi, J. & Muroyama, K. Size control and characterization of spherical carbon aerogel particles from resorcinol-formaldehyde resin. *Carbon N. Y.* 42, 169-175 (2004), Liu, J. et al. Extension of the stober method to the preparation of monodisperse resorcinol-formaldehyde resin polymer and carbon spheres. *Angew. Chemie—Int. Ed.* 50, 5947-5951 (2011), Elkhatat, A. M. & Al-Muhtaseb, S. A. Advances in tailoring resorcinol-formaldehyde organic and carbon gels. *Adv. Mater.* 23, 2887-2903 (2011), and Al-Muhtaseb, S. A. & Ritter, J. A. Preparation and properties of resorcinol-formaldehyde organic and carbon gels. *Adv. Mater.* 15, 101-114 (2003), each of which is incorporated by reference in its entirety. Higher dimensional nanoparticles have not been demonstrated. The difficulty lies in the need to reconcile reaction conditions with colloidal stability. RF resin forms by a two-step reaction: (1) base-catalyzed addition of resorcinol and formaldehyde to form molecular adducts followed by (2) acid-catalyzed polycondensation of these RF adducts. See Elkhatat, A. M. & Al-Muhtaseb, S. A. Advances in tailoring resorcinol-formaldehyde organic and carbon gels. *Adv. Mater.* 23, 2887-2903 (2011), and Al-Muhtaseb, S. A. & Ritter, J. A. Preparation and properties of resorcinol-formaldehyde organic and carbon gels. *Adv. Mater.* 15, 101-114 (2003), each of which is incorporated by reference in its entirety. Particle stability is difficult to achieve at the low pH or high monomer concentration required for the polycondensation step. Reaction of resorcinol and formaldehyde using ~17 mM monomer concentration at even slightly elevated pH >8.3 resulted only in the formation of RF adducts (deep red solution), but no particle nucleation. To drive nucleation, a secondary crosslinking mechanism was introduced. Primary amines are known to react with resorcinol and formaldehyde by Mannich condensation to form benzoxazine groups. See Arnebold, A., Schorsch, O., Stelten, J. & Hartwig, A. Resorcinol-Based Benzoxazine with Low Polymerization Temperature. 1693-1699 (2014), Agag, T., Geiger, S. & Ishida, H. in *Handbook of Benzoxazine Resins* (eds. Ishida, H. & Agag, T.) 263-305 (Elsevier Science, 2011), and Wang, M. W., Jeng, R. J. & Lin, C. H. Study on the ring-opening polymerization of benzoxazine through multisubstituted polybenzoxazine precursors. *Macromolecules* 48, 530-535 (2015), each of which is incorporated by reference in its entirety. Thus ethylenediamine (a bifunctional amine) was shown to be an effective secondary crosslinker, because it allowed a dibenzoxazine bridge to be formed between two resorcinol molecules at relatively low temperatures (~60° C.). Even when a low concentration of ethylenediamine was added (4.5 mM ethylenediamine to 16.7 mM resorcinol, resorcinol in ~4 times excess), precipitation of highly uniform resorcinol-formaldehyde nanofibers (RFN) was observed (FIG. 2C). Incorporation of amine moieties into the resin backbone was confirmed by Fourier transform infrared (FTIR) spectroscopy. The 837 $cm^{-1}$ peak in RFN was absent in pure RF, and was attributed to C—N—C stretching (FIG. 2G). The ether (C—O—C stretch at 1216 $cm^{-1}$ and 1090 $cm^{-1}$) and benzene (aromatic ring stretch at 1605 $cm^{-1}$; vibrations at 1472 $cm^{-1}$ and 1446 $cm^{-1}$ characteristic of 1,2,3,5 and 1,2,3 substituted benzene) vibrations characteristic of pure RF was also observed in RFN. See Ebewele, R. O., River, B. H. & Koutsky, J. A. Relationship between phenolic adhesive chemistry and. *J. Appl. Polym. Sci.* 31, 2275-2302 (1986), and Poljanšek, I. & Krajnc, M. Characterization of phenol-formaldehyde prepolymer resins by in line FT-IR spectroscopy. *Acta Chim. Slov.* 52, 238-244 (2005), each of which is incorporated by reference in its entirety. Chemical bonding states were further probed by X-ray photoelectron spectroscopy (XPS), which confirmed the incorporation of 1.4 at. % nitrogen in RFN (FIG. 2H). The N1s peak of RFN was deconvoluted into two peaks at 401.8 eV (nitrogen moiety in benzoxazine ring) and 399.8 eV (primary or secondary amine) (FIG. 6). The spectrum was deconvoluted into two peaks at 399.8 eV and 401.8 eV, attributed to nitrogen in hydrolyzed (secondary amine) and non-hydrolyzed (tertiary amine) benzoxazine rings respectively. This is the high resolution XPS scan of the N1s peak for RFN, the idea of including this was merely to show that the benzoxazine groups in this material may have partially hydrolyzed in water. It was added for completeness more than anything else.

Figure 7:
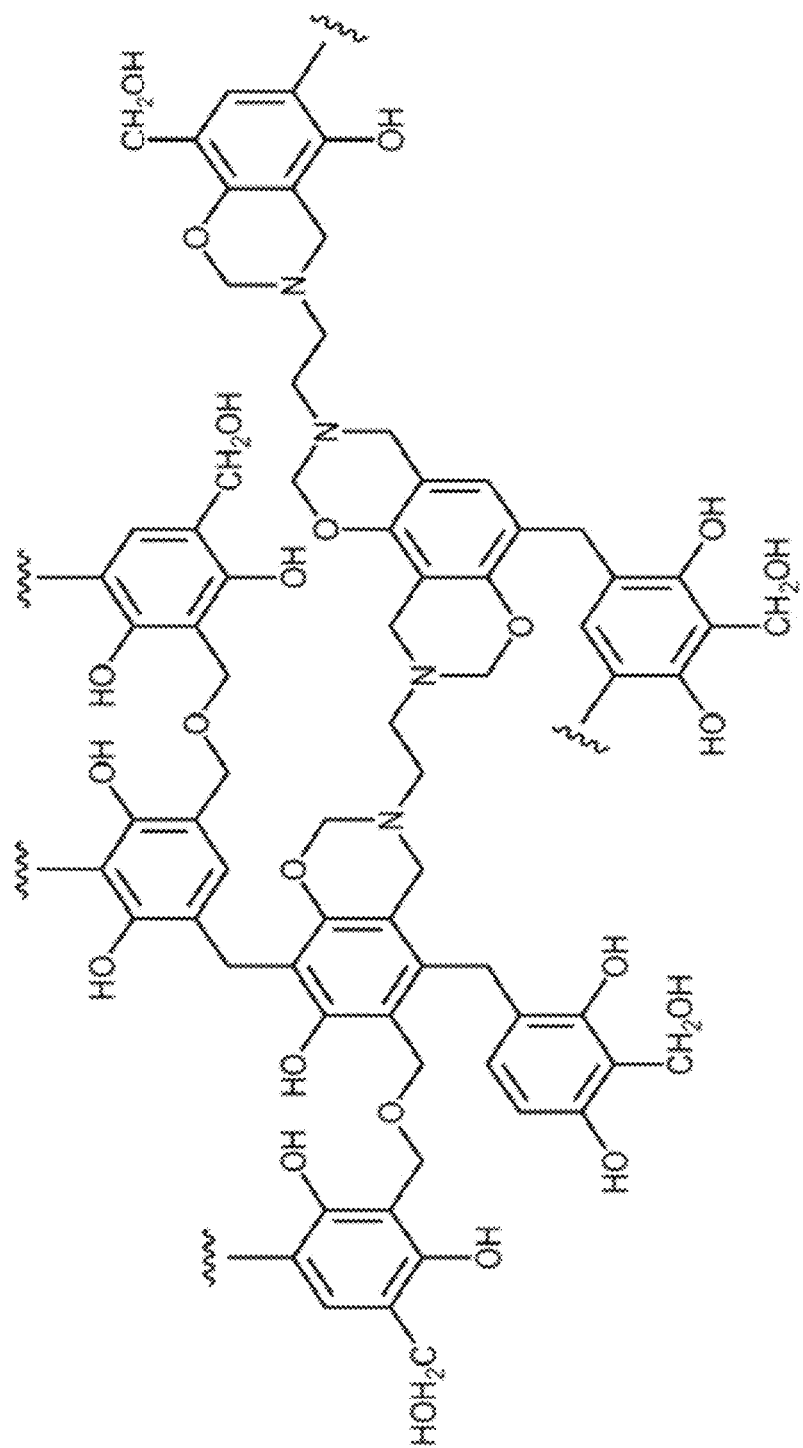
FIG. 7 shows proposed molecular structure of RFN
Figure 8:
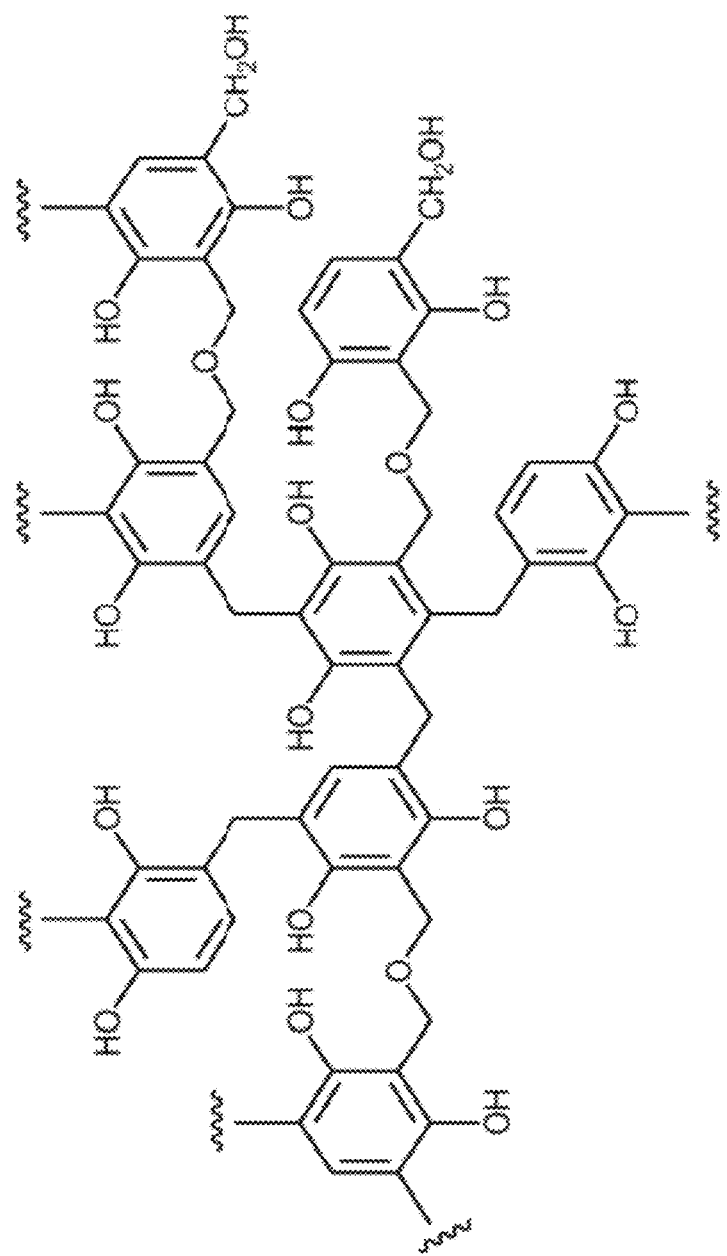
FIG. 8 shows molecular structure of pure RF.

The presence of the latter peak (~25% intensity) can either be attributed to the hydrolysis of benzoxazine rings forming secondary amines or unreacted primary amines, although the latter is unlikely because resorcinol and formaldehyde were used in excess. See Agag, T., Geiger, S. & Ishida, H. in *Handbook of Benzoxazine Resins* (eds. Ishida, H. & Agag, T.) 263-305 (Elsevier Science, 2011), and Moloney, G., Craik, D. & Iskander, M. Qualitative analysis of the stability of the oxazine ring of various benzoxazine and pyridooxazine derivatives with proton nuclear magnetic resonance spectroscopy. *J. Pharm. Sci.* 81, 692-697 (1992), each of which is incorporated by reference in its entirety. These observations show that the molecular structure of RFN is very similar to pure RF, and even though ethylenediamine actively participates in the condensation of RF through the formation of dibenzoxazine bridges, methylene/ether bridges remain the dominant crosslinking groups (>90% by nitrogen content). Thus the precipitation of RF resin can proceed through the initial crosslinking of resorcinol and formaldehyde into small molecular adducts, which subsequently undergo secondary crosslinking by ethylenediamine. The proposed molecular structure of RFN is shown in FIG. 7; for comparison, the molecular structure of pure RF is shown in FIG. 8.

The benzoxazine driven nucleation of RF nanofibers provides a useful framework for further modifications to the molecular structure, for example, incorporating organosilicon moieties. To achieve this, 3-aminopropyltrimethoxysilane (APTMS) was used as a secondary crosslinker in place of ethylenediamine (Table 1). ATPMS is thought to participate in two types of reactions. Its primary amine group undergoes Mannich condensation in the same way as ethylenediamine, forming a single benzoxazine group. Simultaneously, the methoxysilane of APTMS hydrolyzes and condenses to form polysiloxane moieties with a neighboring ATPMS molecules. The addition of a small amount of APTMS (RFN10) did not yield significant changes to the FTIR spectrum compared to pure RF and RFN. However, when an excess of APTMS was added (RFN30 and RFN50), the FTIR spectra were dominated by doublet peaks characteristic of polysiloxane (RFN 30: 1037 $cm^{-1}$, 1109 $cm^{-1}$; RFN50: 1016 $cm^{-1}$, 1096 $cm^{-1}$). See Coates, J. Interpretation of Infrared Spectra, A Practical Approach. *Encycl. Anal. Chem.* 10815-10837 (2006), which is incorporated by reference in its entirety. The drop in intensity of the O—H (~3200 $cm^{-1}$) and C—O—C stretch ~1100 $cm^{-1}$ reflects a reduction in the number of ether bridges. While the loss of aromatic ring vibrations between 1440~1610 $cm^{-1}$ is concomitant with the increase in polysiloxane contribution. Thermogravimetric analysis (TGA) was used to quantify the mass contribution of organosilicon groups. Residual silicon dioxide masses of 11.9 wt. %, 30.2 wt. % and 46.9 wt. % were recorded for RFN10, RFN30 and RFN50 (FIGS. 10A-10D), which is in general agreement with the XPS measured values of silicon content: 1.27 at. %, 9.34 at. % and 13.18 at. % (FIG. 2H). TGA was done in flowing nitrogen using a constant heating rate of 10° C./min. These are thermogravimetric analysis of RFN, RFN10, RFN30 and RFN50 conducted in air at a heating rate of 10° C./min. The weight residue at 800° C. is pure silicon dioxide, and this value was used to determine the total amount of silicon heteroatoms in the resin.

Figure 9:
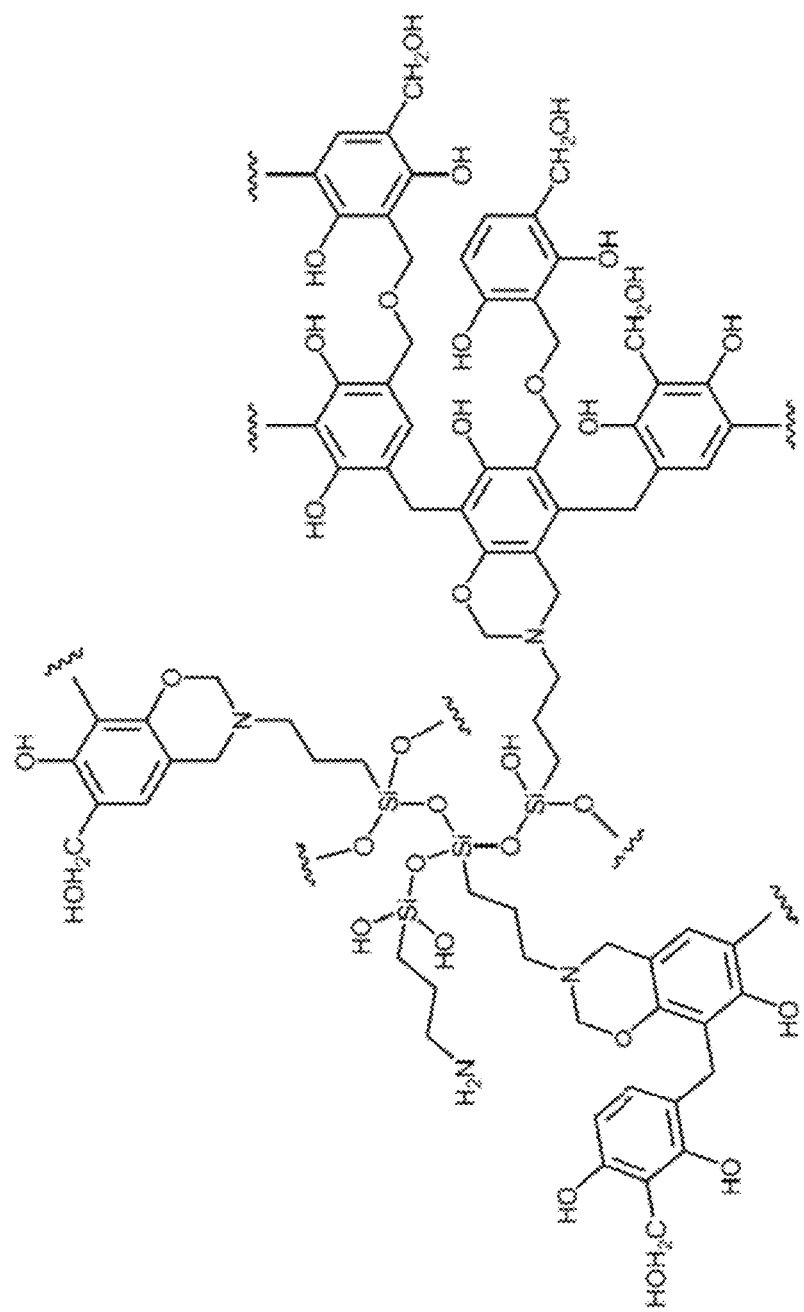
FIG. 9 shows proposed molecular structure of RFN.
Figure 10A:
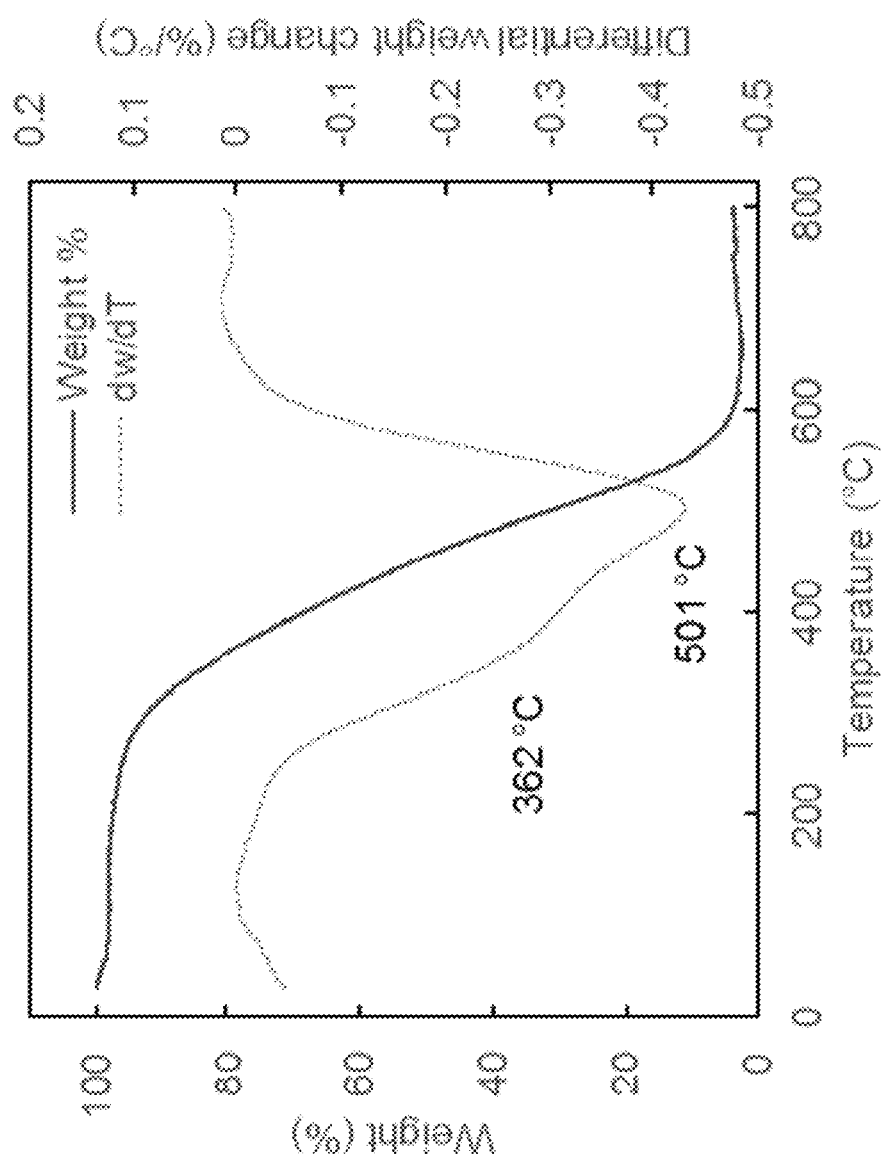
FIGS. 10A-10D show TGA thermograms of RFN (FIG. 10A), RFN10 (FIG. 10B), RFN30 (FIG. 10C) and RFN50 (FIG. 10D).
Figure 10B:
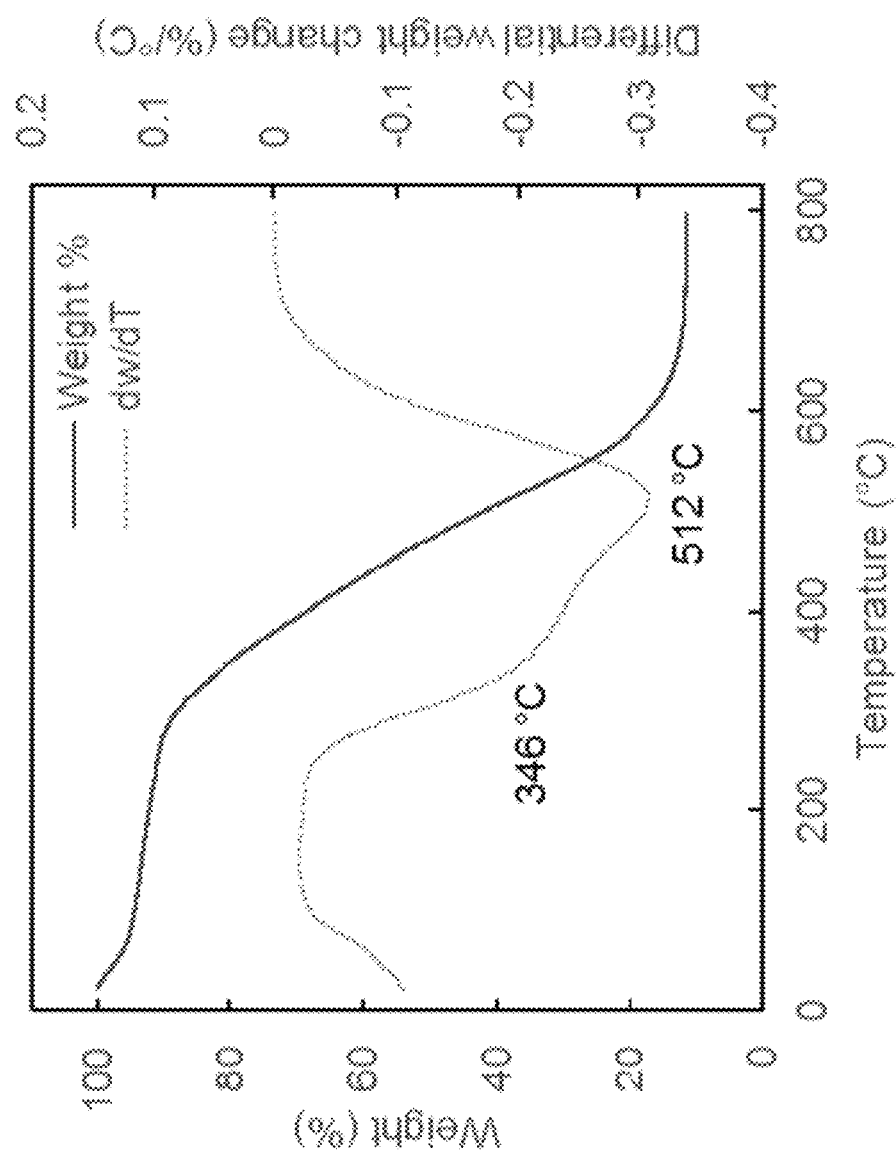
Figure 10C:
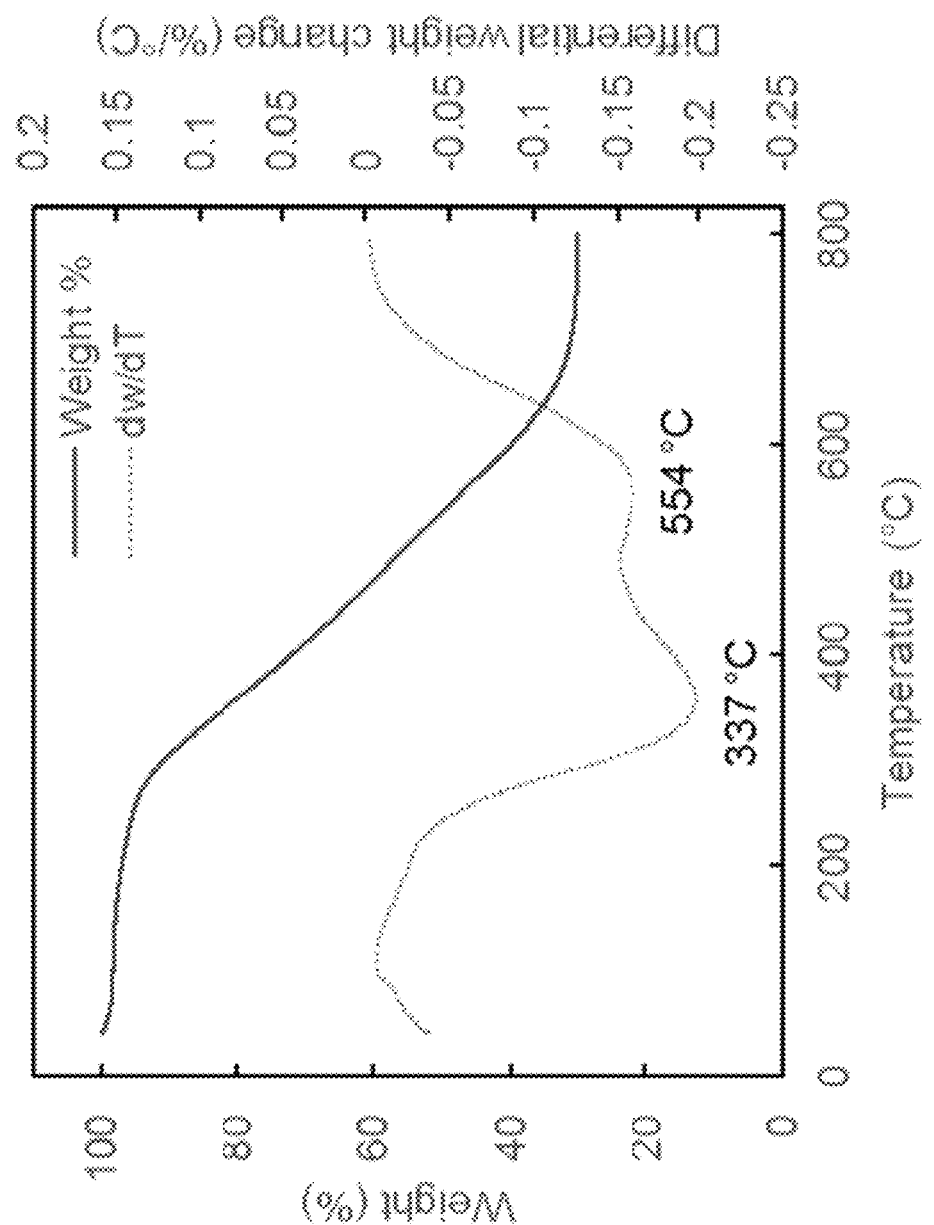
Figure 10D:
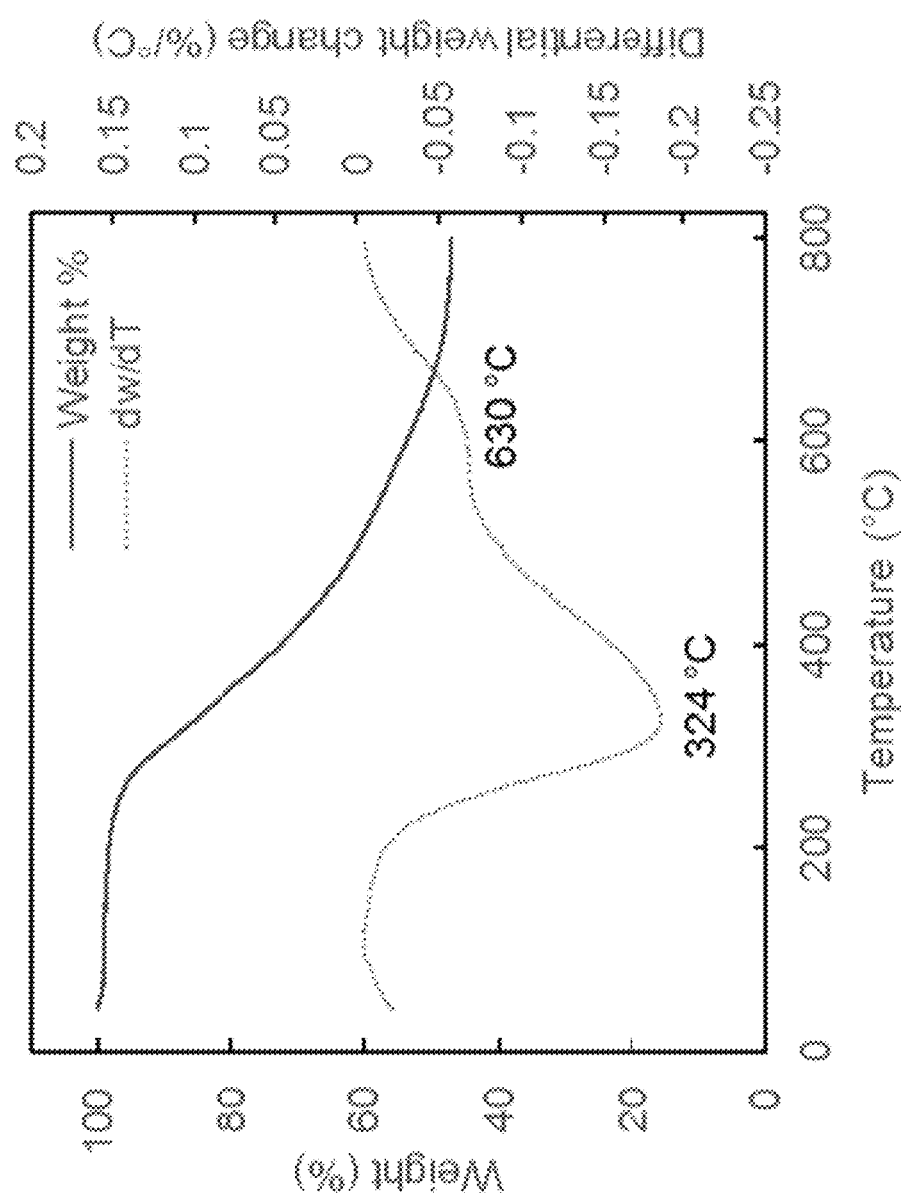

However, even with a high number of organosilicon moieties, the presence of a separate silicon dioxide phase could be resolved using transmission electron microscopy (TEM) (FIGS. 2A, 2B, 2D, 2E and 2F). Therefore, the molecular structure of this APTMS-modified RF resin can include a single phase of crosslinked polysiloxane, aliphatic and phenolic moieties. However, as the organosilicon content increases, the molecular backbone of the RF resin becomes dominated by polysiloxane regions and aliphatic carbons, while phenolic contributions become minimal. The proposed molecular structure for RFN10, RFN30 and RFN50 is shown in FIG. 9. For comparison, addition of tetraethyl orthosilicate in place of ATPMS resulted only in the formation of spherical silicon dioxide particles.

TABLE 1

Summary of resorcinol-formaldehyde samples

| Sample | Secondary crosslinker | Resorcinol:crosslinker molar ratio | Residual $SiO_2$ (wt. %) |
|---|---|---|---|
| RFN | Ethylenediamine | 3.7 | — |
| RFN10 | APTMS | 2.7 | 11.9 |
| RFN30 | APTMS | 0.013 | 30.2 |
| RFN50 | APTMS | 0.00087 | 46.9 |

Figure 11:
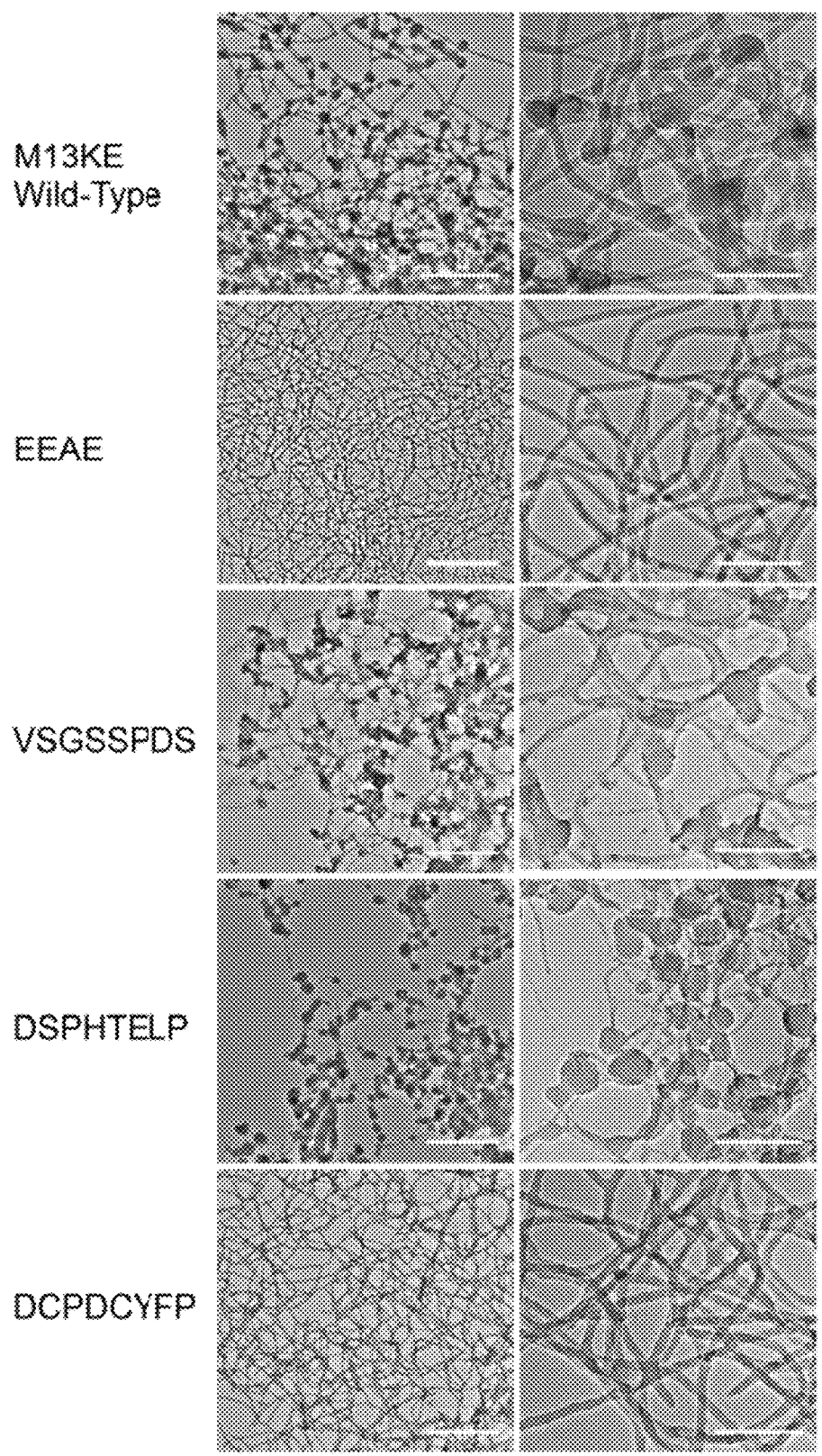
FIG. 11 shows RFN10 synthesized using different virus clones: M13KE wild-type, EEAE, VSGSSPDS, DSPHT-ELP and DCPDCYFP.

Various clones of the M13 bacteriophage expressing different surface moieties were studied for their effect on nanofiber morphology. Each clone was a genetically-modified version of the M13KE wild-type, where a peptide sequence of up to 8 amino acids was expressed on the p8 capsid protein (1 M13KE wild-type, 2 EEAE, 3 VSGSSPDS, 4 DSPHTELP, 5 ENKVE and 6 DCPDCYFP). A similar trend was observed for both ethylenediamine (RFN) and APTMS (RFN10) modifications. No nanostructures were templated by clone 5. A mixture of nanofibers and spherical nanoparticles were templated by clones 1, 3 and 4. Highly uniform nanofibers were templated by clones 2 and 6 (FIG. 11). FIG. 11 shows RFN10 samples synthesized in the exact same way using different clones of the M13 bacteriophage. The wild-type virus was not modified. The other clones had a particular amino acid sequence inserted near the end of the p8 protein (which makes up the viral capsid) as labeled.

These morphological differences illustrate the high sensitivity of organic-organic interfaces to changes in protein sequence resulting in different surface chemistries. While both clones 2 and 6 are both promising from a synthesis point of view, clone 2 is more practical because it exhibits a higher amplification yield and greater purity. The amplification yield of clone 2 is close to 70% that of wild-type and ~10 times higher than clone 6. Furthermore, the high specificity of clone 2 to RF allowed the reaction to be carried out under monomer excess without formation of non-templated particles, which enabled facile scale-up of the reaction volume up to at least 3 liters.

Synthesis carried out in the pH range below 8.3 with no mechanical agitation yields a hydrogel formed by the self-assembly of virus-templated nanofibers. Synthesis in the pH between 8.3~8.8 with (or without) mechanical agitation yields a colloidal dispersion of virus-templated nanofibers. For example, the synthesis of colloidally stable nanofiber was carried out in the pH range of 8.3~8.8 under gentle stirring. Uniform nanofibers with adjustable diameters (between 11~40 nm) and minimal polydispersity were synthesized (FIGS. 2A and 2B). No particle aggregation was observed even after prolonged storage. Reactions conditions, specifically pH and the degree of mechanical agitation, could be used to drive the self-assembly of RF nanofibers into 3-dimensional scaffolds (FIG. 2D). To promote self-assembly, the reaction was carried out at pH slightly below 8.3 under no mechanical agitation. The absence of virus bundling suggests this self-assembly is driven by an interplay of covalent crosslinking and electrostatic repulsion (RF ζ-potential ~−50.5 mV in 2 mM sodium chloride solution).

In a typical synthesis, M13 bacteriophage can be added to an aqueous solution of resorcinol, formaldehyde and 3-aminopropyltrimethoxysilane (APTMS) and incubated at 80° C. overnight to allow complete precipitation. Various M13 bacteriophage clones were screened to find the optimal clone that could be used as a biotemplate. A clone was defined as a genetically-modified version of the M13KE wild-type bacteriophage, where a peptide sequence of up to 8 amino acids was inserted into the p8 capsid protein so as to alter its surface properties. The clones that were screened against are tabulated in Supplementary Table 3.

Figure 1C:
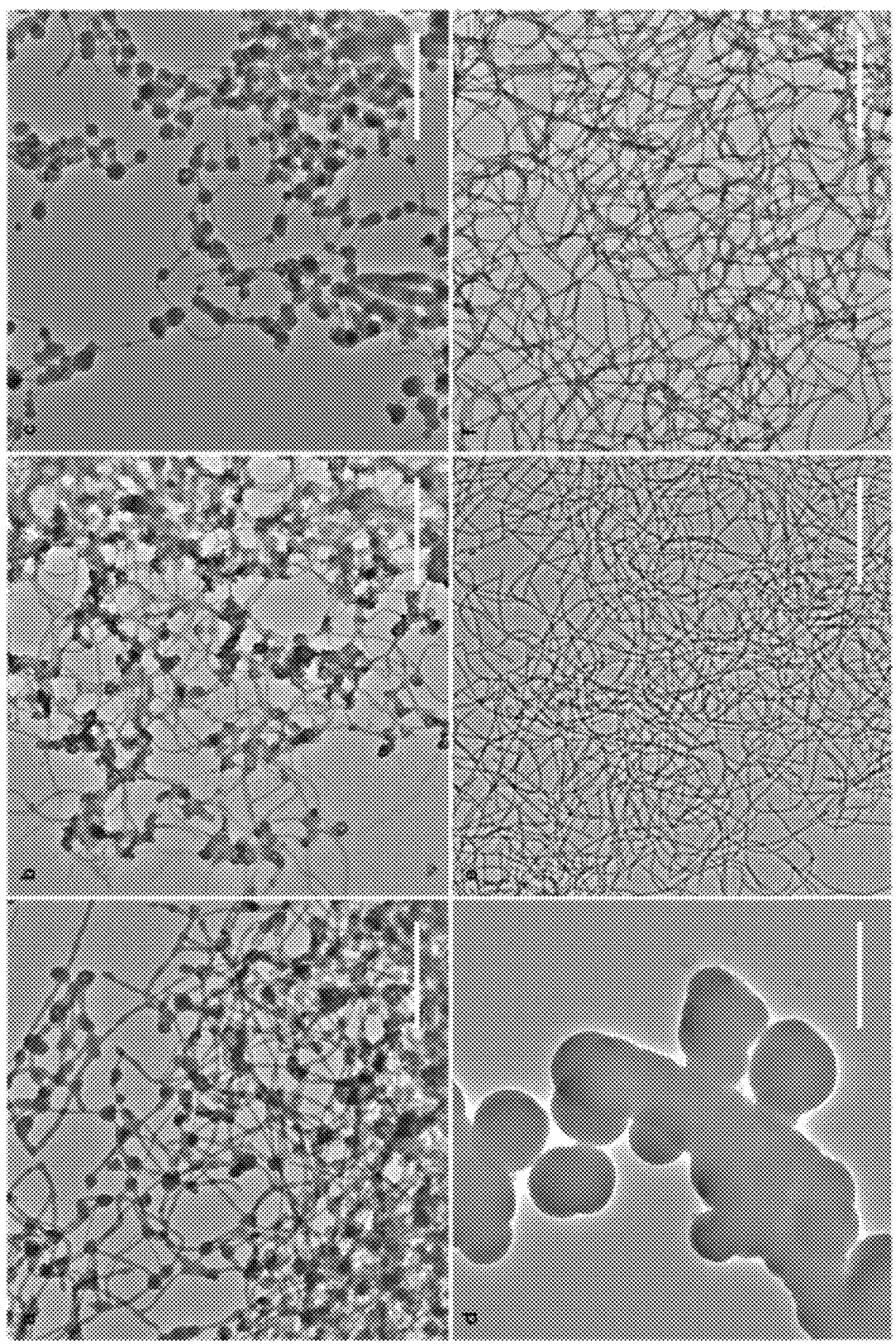
FIG. 1C shows the morphology of the resulting RF resin from an RF precipitation reaction in the presence of each clone under identical reaction conditions.

Referring to FIG. 1C, the RF precipitation reaction was carried out in the presence of each clone under identical reaction conditions, and compared the morphology of the resulting RF resin using transmission electron microscopy (TEM) as shown in FIG. 1C. No distinct morphology was observed for RF resin precipitated using the ENKVE clone, indicating a weak interaction between the viral capsid and RF resin. Comparison of different M13 bacteriophage clones for effectiveness in templating polysiloxane-containing resorcinol-formaldehyde resin (RFN10). The indicators (a)-(f) are representative TEM micrographs of resin synthesized in the presence of clones 1-6 in that order. Clones (e) and (f) showed high specificity, and was able to template highly uniform nanofibers. Clones (a), (b) and (c) showed some specificity. Clone (d) was ineffective, and resulted in the precipitation of large resin aggregates. Scale bars are 1 μm.

A mixture of nanofibers and nanospheres were formed when using wild-type M13 bacteriophage and the VSGSSPDS and DSPHTELP clones, indicating moderate interaction. Highly uniform nanofibers were synthesized using the EEAE and DCPDCYFP clones, indicating strong interactions. The inserts for these two latter clones were on average more acidic than the other inserts. EEAE contained three glutamic acid groups while DCPDCYFP contained two aspartic acid groups. Surface acidity was important to this reaction, because the condensation step in the precipitation of RF resin was proton catalyzed, so acidic functional groups on the coat protein likely helped to promote localized condensation. See, e.g., Elkhatat, A. M. & Al-Muhtaseb, S. A. Advances in tailoring resorcinol-formaldehyde organic and carbon gels. *Adv. Mater.* 23, 2887-2903 (2011), which is incorporated by reference herein. These two clones were also the most negatively charged at pH 8.5 (roughly the initial pH of our reactions) (Supplementary Table 3). See, e.g., Sims, P. A. Use of a spreadsheet to calculate the net charge of peptides and proteins as a function of pH: An alternative to using 'canned' programs to estimate the isoelectric point of these important biomolecules. *J. Chem. Educ.* 87, 803-808 (2010), which is incorporated by reference herein. This would likely have promoted electrostatic attraction between the bacteriophage and the positively-charged, protonated methylol resorcinol intermediates that formed by the addition of resorcinol and formaldehyde. See, e.g., Elkhatat, A. M. & Al-Muhtaseb, S. A. Advances in tailoring resorcinol-formaldehyde organic and carbon gels. *Adv. Mater.* 23, 2887-2903 (2011), which is incorporated by reference herein. In addition, DCPDCYFP was also relatively hydrophobic, likely rendering the surfaces more favorable for nucleating organic materials based on stronger hydrophobic-hydrophobic interactions (Supplementary Table 3). Of these two clones, the EEAE clone was selected for large-scale synthesis, because it was most amendable to large-scale amplification due to its higher amplification yield. In general, the amplification yield of a genetically modified M13 bacteriophage is substantially lower than the wild-type bacteriophage. However, the amplification yield of EEAE reached as high as 70% that of wild-type, making it one of the fastest growing clones that has been designed.

Polysiloxane moieties were incorporated into the RF resin by the addition of APTMS. APTMS was used in order to exploit the Mannich condensation of its primary amine group with resorcinol and formaldehyde. This allowed the polysiloxane to be covalently incorporated into the RF resin backbone, forming the macromolecular structure shown in FIG. 1B. Polysiloxane content could be controlled by tuning the ratio of APTMS to resorcinol and formaldehyde. In order to systematically study the effect of polysiloxane on the properties of the final carbon nanofibers, 3 RF nanofiber samples were prepared with increasing polysiloxane content (RFN10, RFN30 and RFN50). A control sample (RFN) was prepared without polysiloxane by replacing APTMS with a small amount of ethylenediamine (EDA). In the absence of EDA, RF precipitation was much less efficient as shown in FIGS. 2G and 2H. EDA was thought to facilitate RF polymerization by acting as both a catalyst, as well as a secondary crosslinker. See, e.g., Arnebold, A., Schorsch, O., Stelten, J. & Hartwig, A. Resorcinol-based benzoxazine with low polymerization temperature. *J. Polym. Sci. Part A Polym. Chem.* 52, 1693-1699 (2014).

Figure 28:
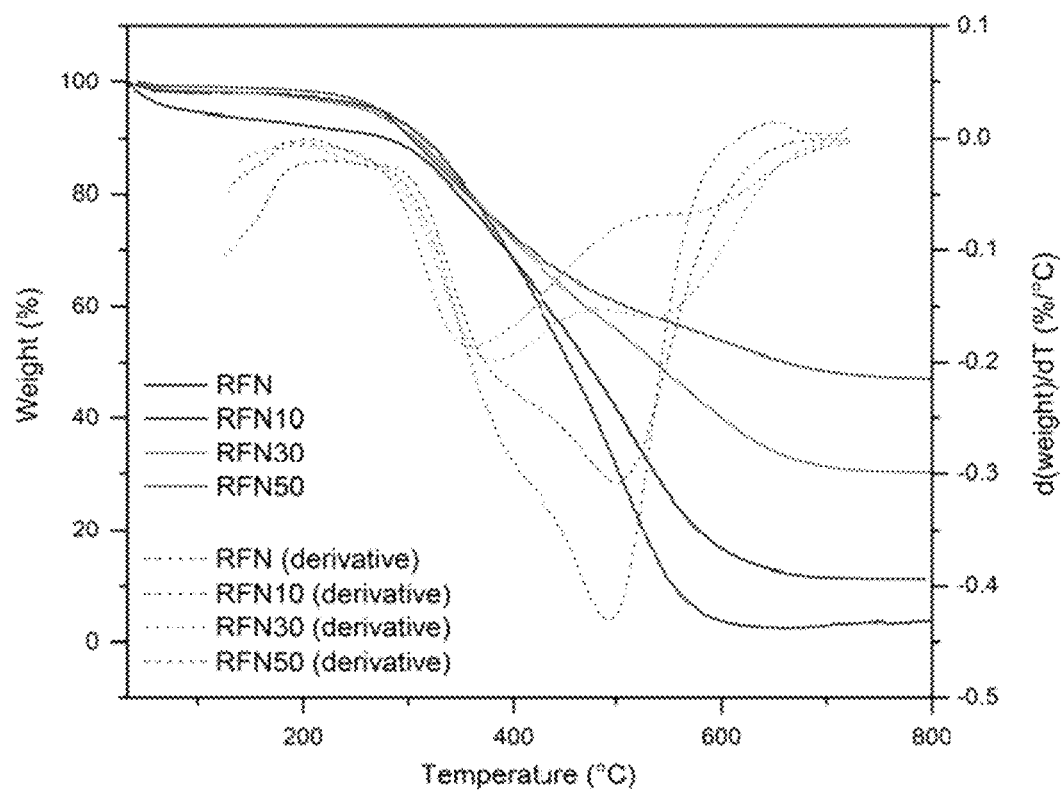
FIG. 28 shows a TGA thermograms of RFN, RFN10, RFN30 and RFN50. All samples showed two major phases of weight loss. The first phase is in the range 300~400° C., while the second is in the range 500~600° C.
Figure 29:
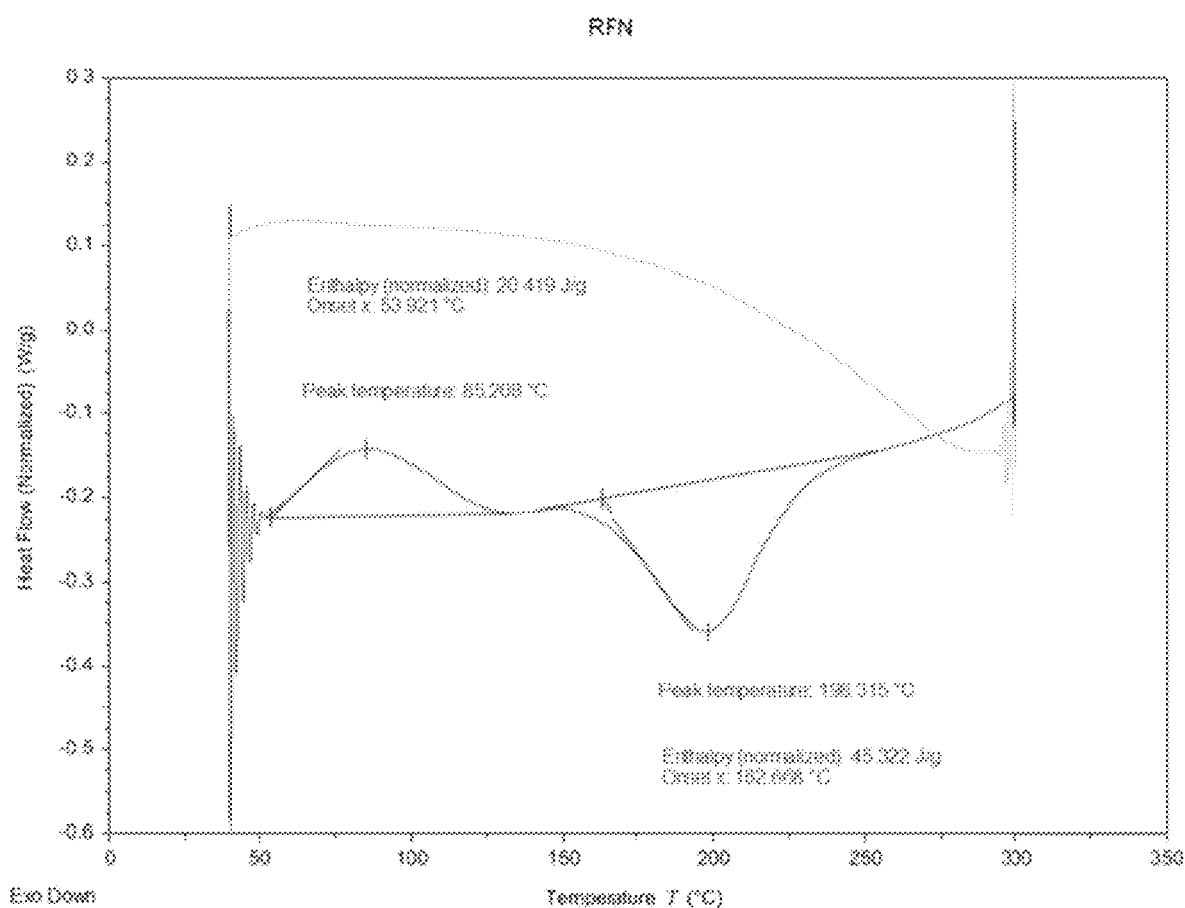
FIG. 29 shows a DSC thermogram of RFN using a scan rate of 10° C./min (black line: heating, light blue line: cooling).
Figure 30:
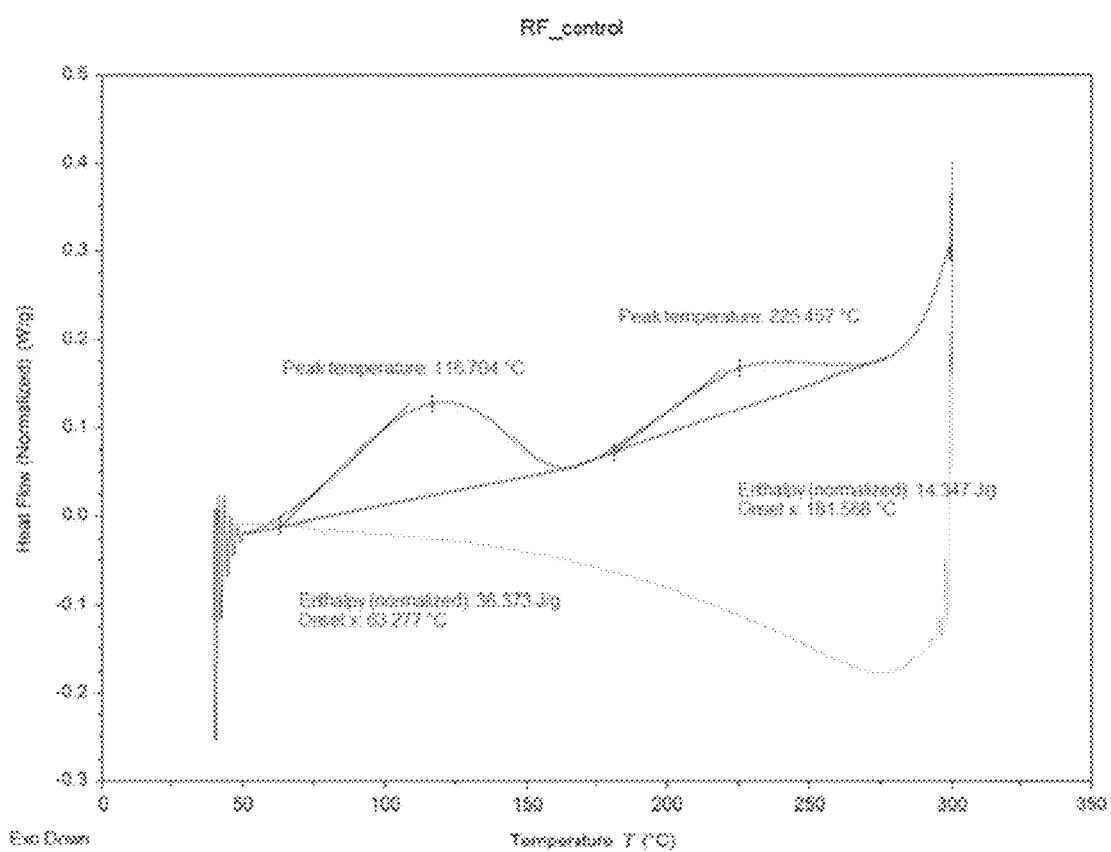
FIG. 30 shows a DSC thermogram of pure RF resin using a scan rate of 10° C./min (black line: heating, light blue line: cooling).
Figure 31:
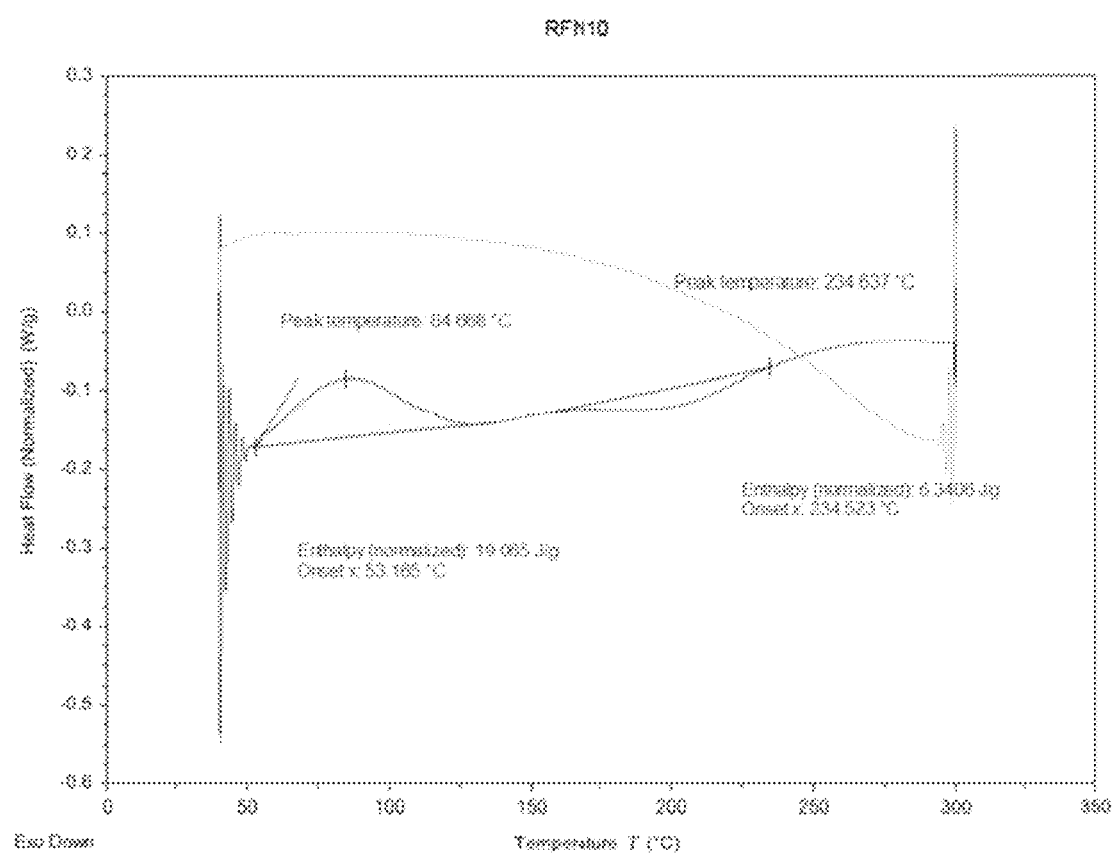
FIG. 31 shows a DSC thermogram of RFN10 using a scan rate of 10° C./min (black line: heating, light blue line: cooling).
Figure 32:
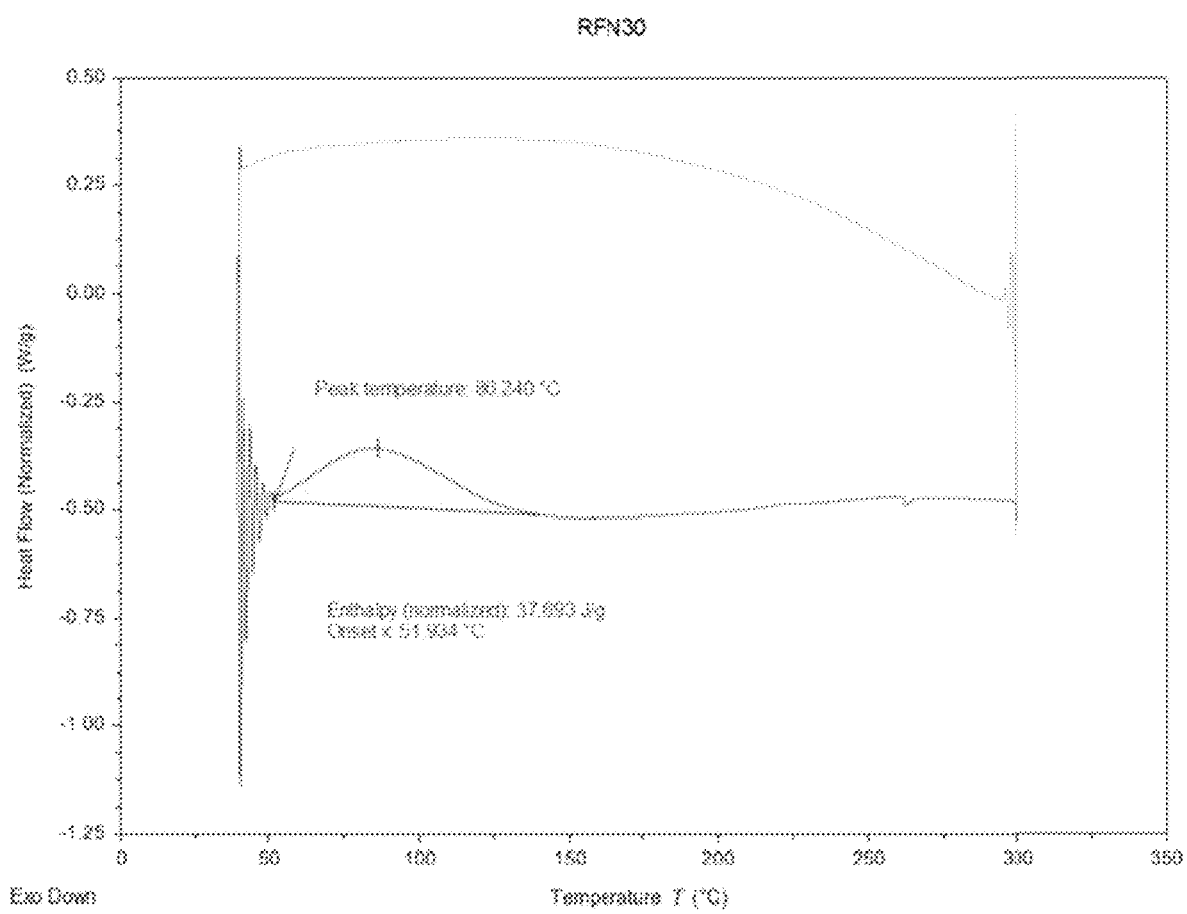
FIG. 32 shows a DSC thermogram of RFN30 using a scan rate of 10° C./min (black line: heating, light blue line: cooling).
Figure 33:
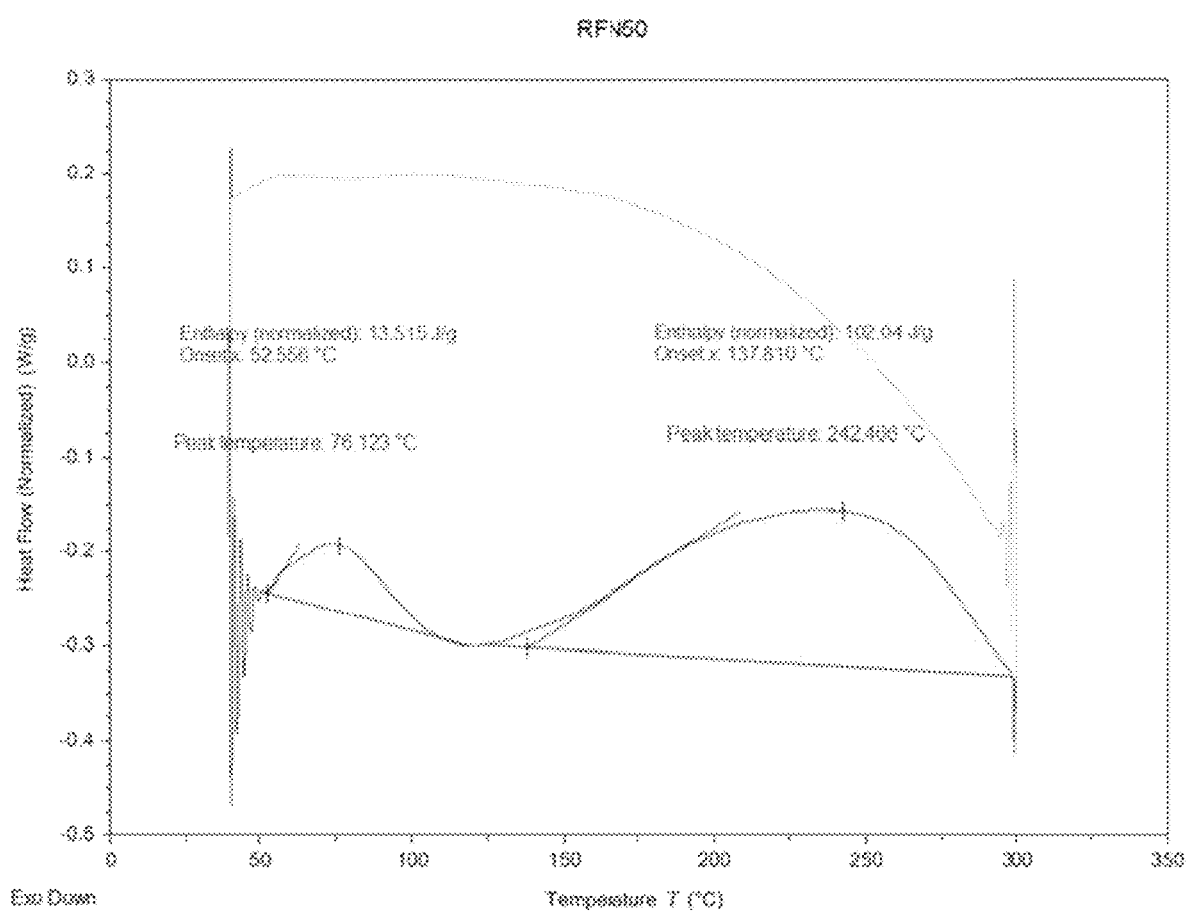
FIG. 33 shows a DSC thermogram of RFN50 using a scan rate of 10° C./min (black line: heating, light blue line: cooling).
Figure 34:
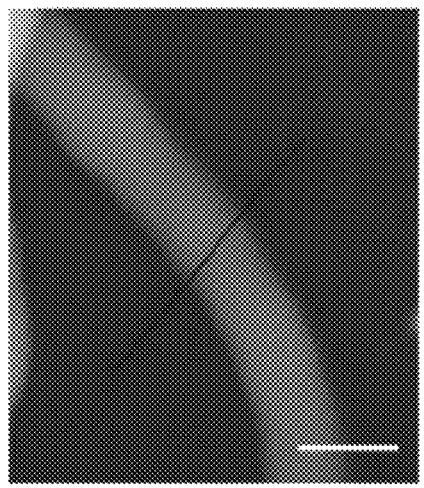
FIG. 34 shows a STEM micrograph of RFN (left). The dark-red line marks the position of the EDX line-scan. Scale bar: 50 nm. Elemental intensities for silicon and oxygen across the line-scan are shown on the right.
Figure 34:
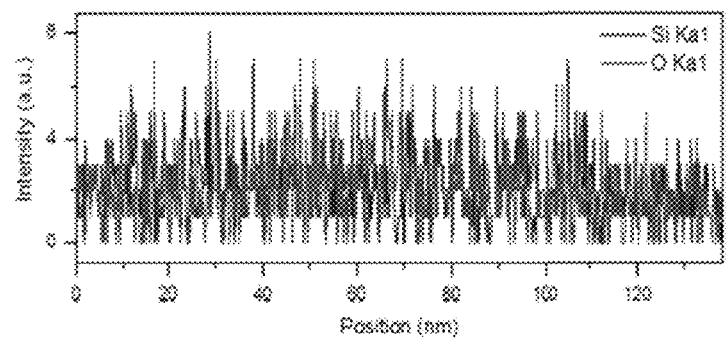
Figure 35:
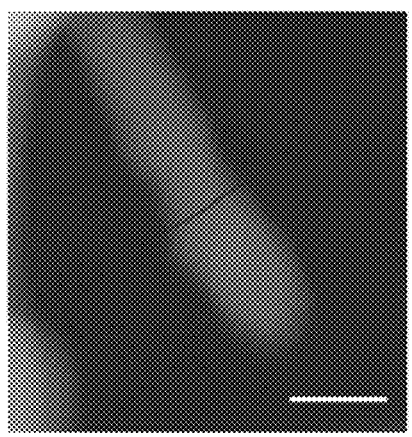
FIG. 35 shows a STEM micrograph of RFN10 (left). The dark-red line marks the position of the EDX line-scan. Scale bar: 50 nm. Elemental intensities for silicon and oxygen across the line-scan are shown on the right.
Figure 35:
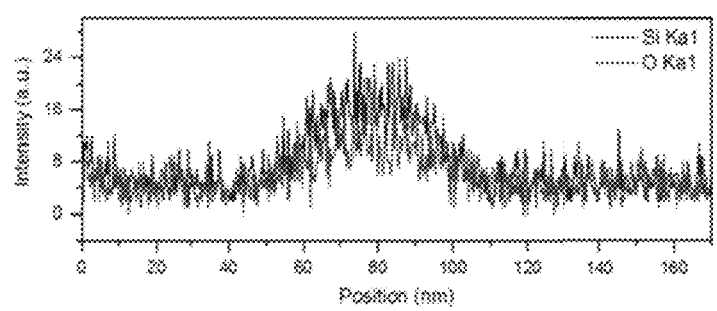
Figure 36:
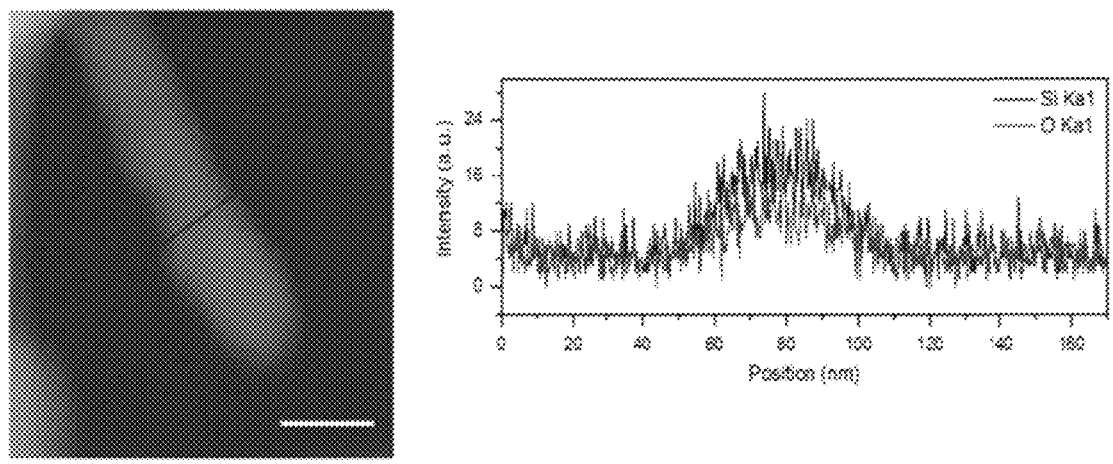
FIG. 36 shows a STEM micrograph of RFN30 (left). The dark-red line marks the position of the EDX line-scan. Scale bar: 50 nm. Elemental intensities for silicon and oxygen across the line-scan are shown on the right.
Figure 37:
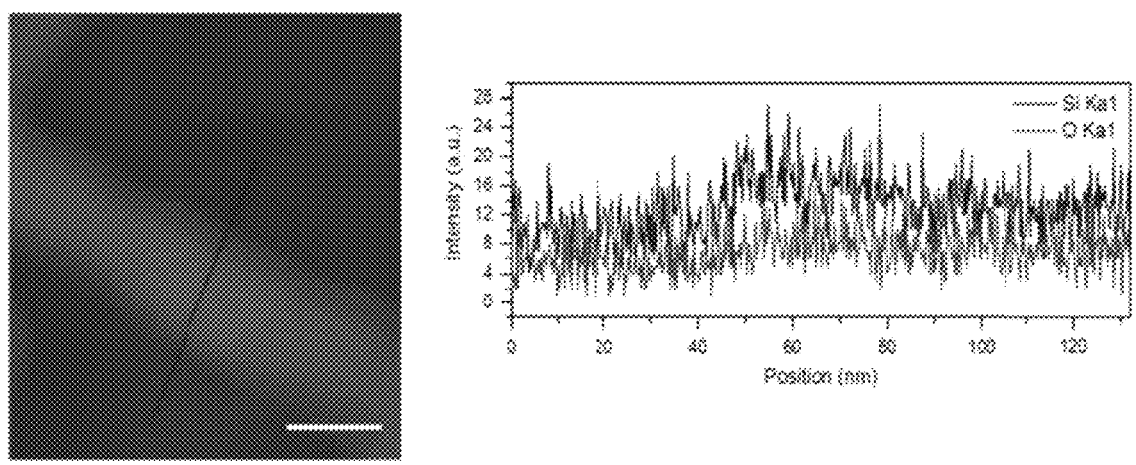
FIG. 37 shows a STEM micrograph of RFN50 (left). The dark-red line marks the position of the EDX line-scan. Scale bar: 50 nm. Elemental intensities for silicon and oxygen across the line-scan are shown on the right.

Transmission electron micrographs in FIG. 19 confirm uniform networks of individual RF nanofibers were formed for all samples, regardless of polysiloxane content. Average nanofiber diameters ranged from 32 to 42 nm (FIG. 24, FIG. 25, FIG. 26 and FIG. 27). The length of individual fibers was ~900 nm, which indicated that no bundling of the viruses had occurred during synthesis. The increasing concentration of polysiloxane in RFN10 to RFN50 was visible from the color change from dark-red to off-white (Error! Reference source not found. B), and was confirmed using various spectroscopic and thermogravimetric techniques. In particular, the presence of strong FTIR doublet peaks in RFN30 (1037 $cm^{-1}$, 1109 $cm^{-1}$) and RFN50 (1016 $cm^{-1}$, 1096 $cm^{-1}$) corresponded to polysiloxane moieties (Error! Reference source not found). See, e.g., Coates, J. Interpretation of Infrared Spectra, A Practical Approach. Encycl. *Anal. Chem.* 10815-10837 (2006). doi:10.1002/9780470027318.a5606, which is incorporated by reference herein. This was further corroborated by the increasing silicon content from XPS analysis (Error! Reference source not found. D). Residual weights from thermogravimetric analysis of 11.9 wt. %, 30.2 wt. % and 46.9 wt. % for RFN10, RFN30 and RFN50 corresponded to pure silicon dioxide after complete oxidation of the organic component (FIG. 28). Differential scanning calorimetric (DSC) scan of RFN revealed an exothermic peak at 198° C. with an enthalpy of 45.3 J/g that was characteristic of the thermal ring-opening polymerization of benzoxazine (FIG. 29). See, e.g., Wang, M. W., Jeng, R. J. & Lin, C. H. Study on the ring-opening polymerization of benzoxazine through multisubstituted polybenzoxazine precursors. *Macromolecules* 48, 530-535 (2015), which is incorporated by reference herein. This exothermic peak was not observed in pure RF resin, which instead exhibited an endothermic peak at 225° C. (FIG. 30). A much smaller exothermic peak was observed in RFN10 at 234.5° C. with an enthalpy of 6.3 J/g (FIG. 31), while the same peak was altogether absent in RFN30 and RFN50 (FIG. 32 and FIG.

33). The gradual reduction and elimination of this peak with increasing polysiloxane content could be attributed to the increasing rigidity of the resin backbone.

Characterization of Biotemplated Carbon Nanofibers

The incorporation of organosilicon moieties into RF nanofibers allowed microporous carbon nanofibers with up to ~2000 m$^2$/g surface area to be directly synthesized by carbonization (FIGS. 3A, 3B, 3C, 3D and Table 2). Due to the low carbon-to-silicon ratio of ~4, RFN50 could not be used as a carbon precursor, therefore only carbon nanofibers derived from RFN, RFN10 and RFN30 are discussed (Table 2). The unique advantage of this approach over conventional activation methods was that the nanotexture of the carbon nanofiber could precisely controlled at multiple levels simply by tuning the organosilicon content. The nanotexture of the carbon nanofiber includes the disorder and bonding state of carbon atom (π-electron delocalization) at the molecular level, and the graphitic crystallite size (in-plane $L_a$ and inter-planar $L_c$) and order (interlayer spacing, stacking) at the microstructural level. The nanotexture of the carbon directly determines material properties such as surface area and electrical conductivity. Furthermore, self-assembly of the nanofibers at the microscopic level allowed facile fabrication of 3-dimensional carbon nanostructures such as aerogels.

TABLE 2

Summary of carbon nanofiber samples.

| Sample | Precursor | BET surface area (m$^2$/g) | t-Plot micropore area (m$^2$/g) | Sheet resistivity (Ωm) | $L_a$ (Raman) (nm) | $I_D/I_G$ ratio |
|---|---|---|---|---|---|---|
| RFN-1100C | RFN | 365 | 251 | $2.28 \times 10^{-3}$ | 2.6 | 1.68 |
| RFN10-1100C | RFN10 | 776 | 643 | $2.80 \times 10^{-3}$ | 1.8 | 1.74 |
| RFN30-1100C | RFN30 | 1934 | 1549 | $5.24 \times 10^{-1}$ | 1.6 | 1.38 |

Figures 3A, 3B, 3C, 3D:
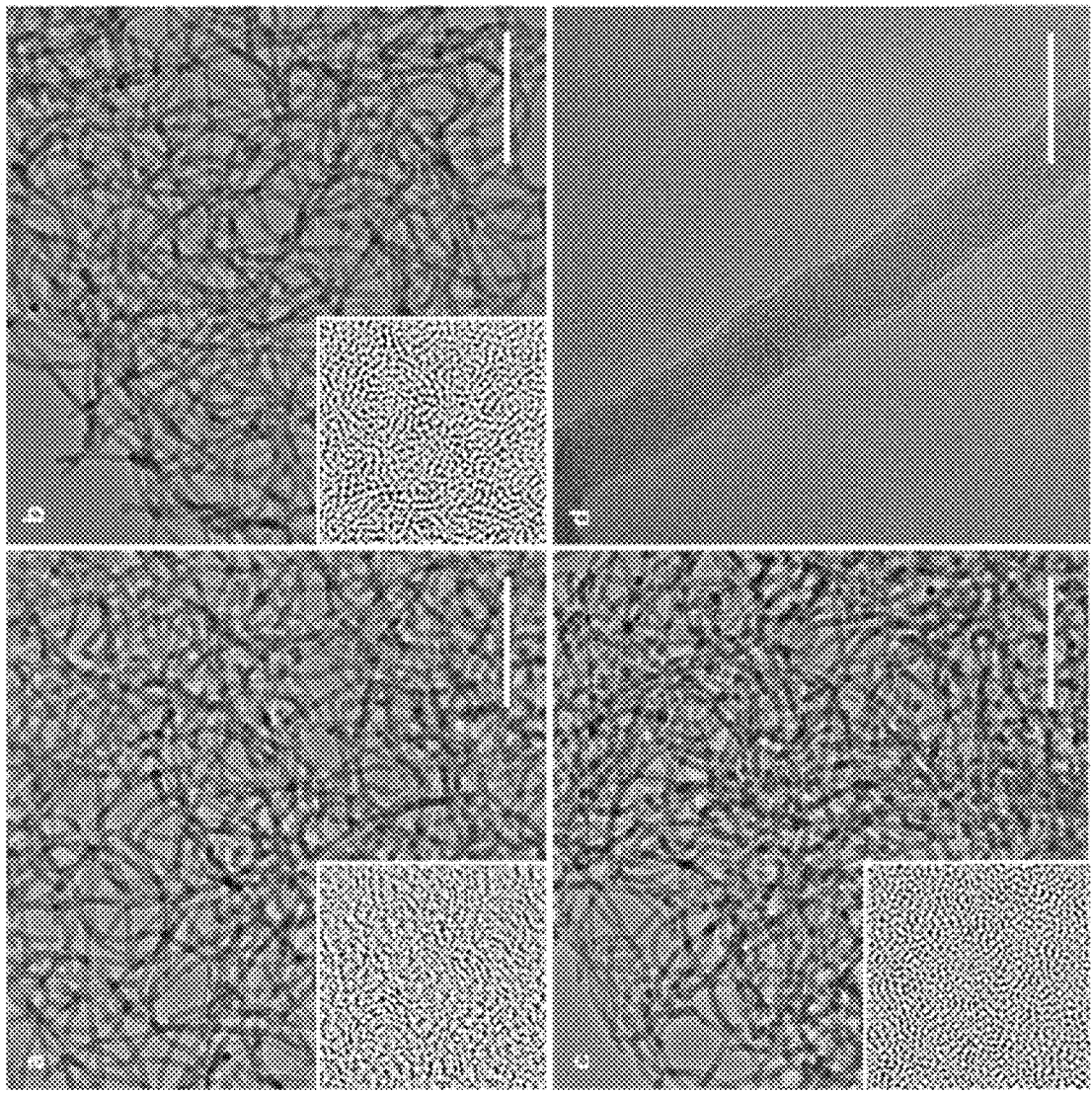
FIGS. 3A-3H show morphological and structural characterizations of biotemplated carbon nanofibers.

Carbon nanotexture was directly observed using high resolution TEM (FIGS. 3A, 3B and 3C insets). Fast Fourier transform (FFT) was used to clean the TEM images, and the image entropies were calculated (see Methods). The degree of disorder and crystallite size could be directly observed and qualitatively compared. RFN-1100C has a prototypical turbostratic texture with clear local domains of graphene stacking (image entropy of 0.0062). RFN10-1100C and RFN30-1100C show much higher degree of disorder, and stacking domains were not observed (higher image entropies of 0.0118 and 0.0148 respectively).

Figure 3E:
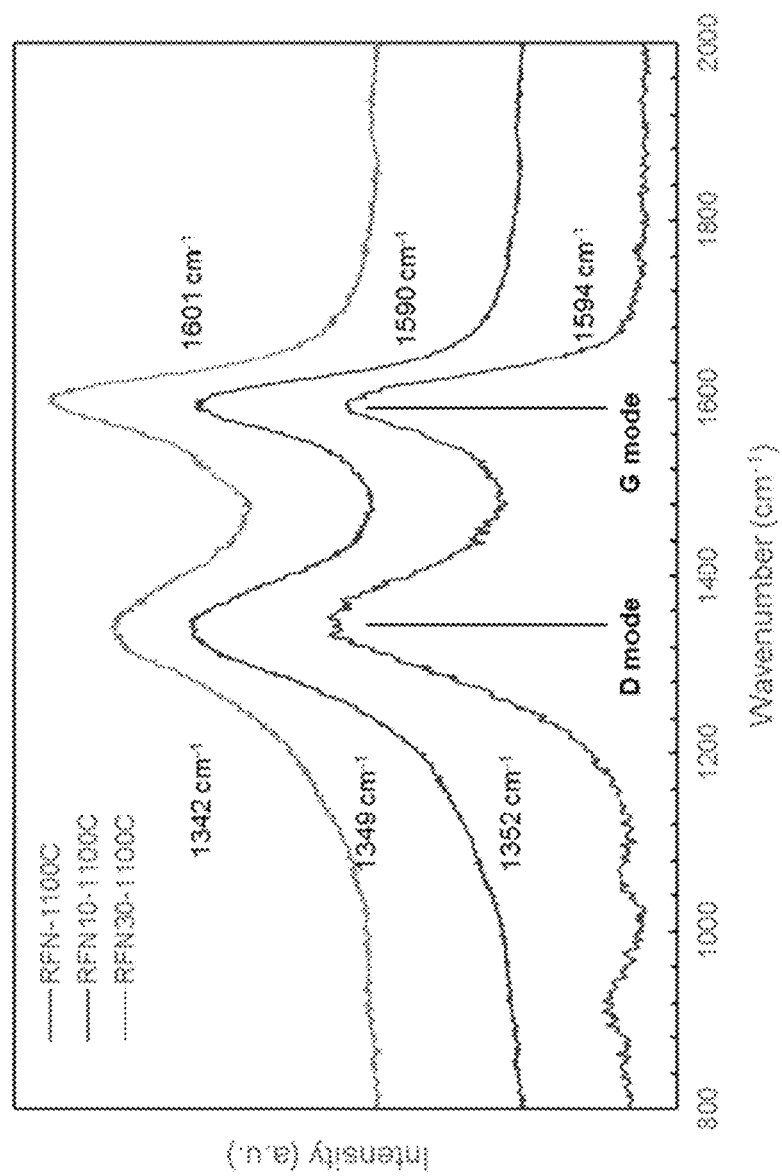
Figure 3F:
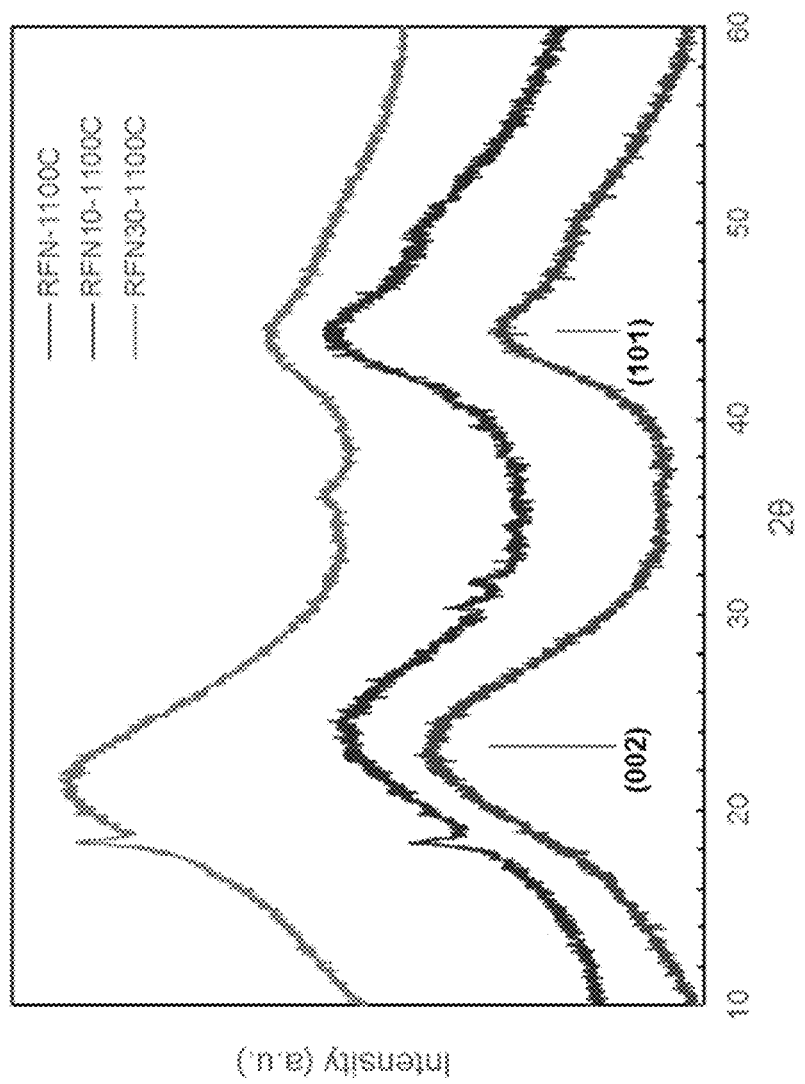

Crystallite size, carbon bonding state and geometric distortions in graphene stacking were studied using Raman spectroscopy and XRD. See Dresselhaus, M. S. et al. New characterization techniques for activated carbon fibers. *Carbon N. Y.* 30, 1065-1073 (1992), Wang, Y., Alsmeyer, D. C. & McCreery, R. L. Raman Spectroscopy of Carbon Materials: Structural Basis of Observed Spectra. *Chem. Mater.* 2, 557-563 (1990), Ferrari, A. C. & Robertson, J. Interpretation of Raman spectra of disordered and amorphous carbon. 61, 95-107 (2000), and Li, Z. Q., Lu, C. J., Xia, Z. P., Zhou, Y. & Luo, Z. X-ray diffraction patterns of graphite and turbostratic carbon. *Carbon N. Y.* 45, 1686-1695 (2007), each of which is incorporated by reference in its entirety. The Raman spectra for all samples comprised of two major peaks associated with the G mode (1590~1600 cm$^{-1}$) and D mode (~1350 cm$^{-1}$) vibrations (FIG. 3E). The intensity ratios $I_D/I_G$ were calculated by integrating peak areas and summarized in Table 2. When a small amount of organosilicon moieties were added (RFN10-1100C compared with RFN-1100C), $I_D/I_G$ increased slightly. However, when a larger amount of silicon moieties were added (RFN30-1100C compared with RFN10-1100C), $I_D/I_G$ decreased. The G mode peak position was similar for RFN-1100C and RFN10-1100C, but was slightly upshifted to 1601 cm$^{-1}$ for RFN30-1100C. These two observations imply an increase in the degree of disorder, decrease in the in-plane crystallite size ($L_a$) and a corresponding decrease π-electron delocalization with increasing organosilicon content. This is rationalized as follows: the G mode vibration is due to the relative in-plane stretch of sp$^2$ carbon atoms ($E_{2g}$ symmetry) and the D mode vibration is a breathing mode ($A_{1g}$ symmetry), the latter of which is physically constrained to single 6-member aromatic rings or small clusters. When carbon disorder is lower in the case of RFN-1100C ($L_a$>~20 Å), further increasing disorder reduces crystallite size and loosens the restriction on breathing mode vibrations, corresponding to an increase in D mode intensity following the Tuinstra-Koenig correlation. See Tuinstra, F. & Koenig, J. L. Raman Spectrum of Graphite. *J. Chem. Phys.* 53, 1126-1130 (1970), which is incorporated by reference in its entirety. When the level of disorder increases further and turbostratic carbon gives way to more amorphous carbon (RFN30-1100C relative to RFN10-1100C), the number of 6-member rings decreases as the sp$^2$ carbon atoms become increasingly olefinic in nature, and D mode intensity drops according to the Ferrari-Robertson correlation. See Ferrari, A. C. & Robertson, J. Interpretation of Raman spectra of disordered and amorphous carbon. 61, 95-107 (2000), which is incorporated by reference in its entirety. The increasing proportion of olefinic sp$^2$ stretch, which is slightly higher energy than the corresponding aromatic stretch, was further corroborated by the upshift in G mode peak position. Id. XRD provides further insight into the state of graphene stacking and their geometric distortions. Three major peaks were observed in all samples between 10° and 60° 2θ (FIG. 3F). The peak at ~23° is attributed to diffraction at (002) planes and yields the interlayer spacing $d_{002}$. The peak at ~44° is mainly attributed hexagonal (101) diffraction planes, but likely consists of multiple diffraction planes. These may include the hexagonal (100) planes, but also (101) and (102) planes more characteristic of a rhombohedral crystal structure that arise due to the translational mismatch in graphene stacking. Similarly, the ~48° may be a combination of hexagonal (102) and (004) planes. See Inagaki, M. & Kang, F. *Fundamental Science of Carbon Materials. Materials Science and Engineering of Carbon: Fundamentals* (2014), which is incorporated by reference in its entirety. The peak intensity ratios are similar for RFN-1100C and RFN10-1100C, but an upshift in (002) peak position (23.8° compared to 22.6°) as well as broadening was observed in the latter (FWHM of 0.26° compared to 0.14°). This suggests a simultaneous decrease in inter-planar crystallite size $L_c$ along with reduction in interlayer spacing, and possibly greater fluctuations in spacing. The diffractogram for RFN30-1100C was significantly different to RFN10-1100C, where a downward shift in (002) position was observed along with a significant decrease in the (101)/(002) intensity ratio. The decrease in (002) position reflects an increase in average interlayer spacing, which can be explained by irregularities in graphene stacking that is commensurate with higher levels of imperfections in the graphene planes (greater proportion of olefinic sp$^2$ carbons). The loss of (101) peak intensity cannot be adequately explained by translational mismatch alone nor by crystallite size reduction due to the decrease in peak (101)/(002) peak intensity ratio, and is likely due additional rotational crystallite distortions. See Li, Z. Q., Lu, C. J., Xia, Z. P., Zhou, Y. & Luo, Z. X-ray diffraction patterns of graphite and turbostratic carbon. *Carbon N. Y.* 45, 1686-1695 (2007), which is incorporated by reference in its entirety. The effect of increasing organosilicon content on the resulting carbon can be summarized: (1) increase in molecular defects of graphene layers and localization of π-electron; (2) reduction in in-plane ($L_a$) and inter-planar ($L_c$) crystallite size; and (3) increase in crystallite geometric distortion and packing disorder.

A molecular templating mechanism can explain these differences in nanotexture. At the atomic level, carbonization is associated with the cyclization of carbon atoms to form graphitic planes. See Liu, J. et al. Extension of the stober method to the preparation of monodisperse resorcinol-formaldehyde resin polymer and carbon spheres. *Angew. Chemie—Int. Ed.* 50, 5947-5951 (2011), which is incorporated by reference in its entirety. A few graphitic planes stack together to form crystallites that assemble in a disorderly fashion into a turbostratic microstructure with inbuilt microporosity. As carbon is heated above 800~900° C., crystallites begin to partially align leading to a loss of microporosity. See Dresselhaus, M. S. et al. New characterization techniques for activated carbon fibers. *Carbon N. Y.* 30, 1065-1073 (1992), Inagaki, M. & Kang, F. *Fundamental Science of Carbon Materials. Materials Science and Engineering of Carbon: Fundamentals* (2014), and Qian, W. et al. Human hair-derived carbon flakes for electrochemical supercapacitors. *Energy Environ. Sci.* 7, 379-386 (2013), each of which is incorporated by reference in its entirety. The organosilicon moieties in the organosilicon precursor can affect micropore formation in two ways: (1) confining crystallite formation and (2) restricting crystallite alignment. When the organosilicon content is high, the molecular structure comprises of organic clusters embedded in a Si—O—Si percolating backbone. Formation and growth of graphitic planes is geometrically confined to the size of the organic clusters and assembly of individual graphene platelets into a coherent superlattice is impeded (RFN50 represents the limiting condition where no coherent superlattice was formed). This partially explains why $L_a$ of RFN, RFN10 and RFN30 decrease in this order. The second contribution of organosilicon moieties is to physically constrict alignment of the graphitic crystallites. The Si—O—Si backbone is highly rigid and maintains its rigidity even at high temperatures due to the stability of the Si—O bond and its diamond-like configuration. Silicon dioxide clusters are retained in the carbon superlattice in between platelets and physically impede their alignment and graphitization at elevated temperatures.

Figure 3G:
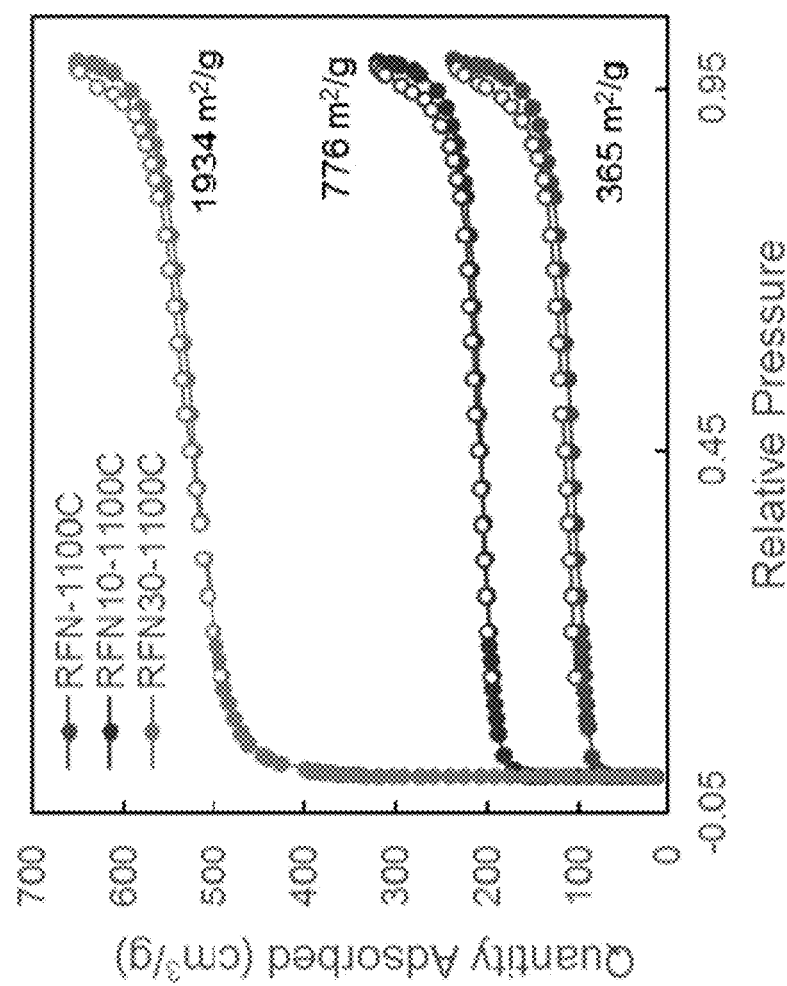
Figure 3H:
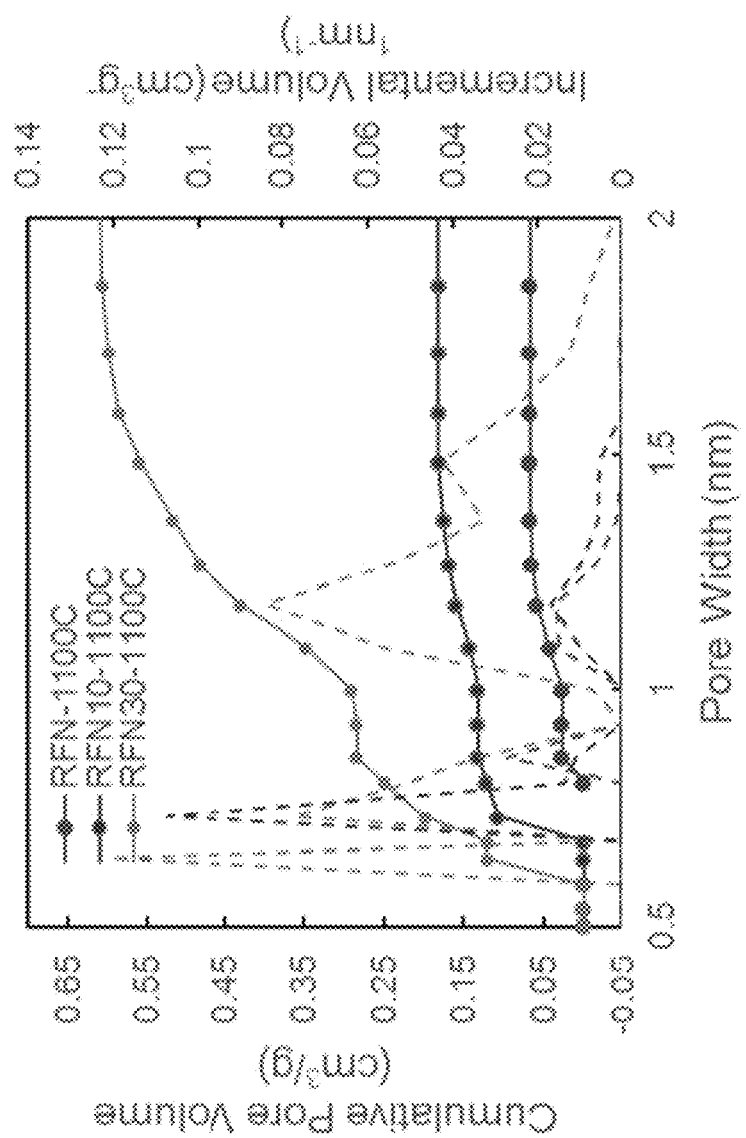

Macroscopically, structural changes to the carbon nanotexture manifest in an increase in surface area and decrease in electrical conductivity. Surface area was measured using Brunauer-Emmett-Teller (BET) analysis. A type II isotherm was observed with a bimodal micropore distribution (~0.7 nm and ~1.2 nm) characteristic of microporous carbons (FIGS. 3G and 3H). Total surface area, mostly attributed to micropores, increased with increasing organosilicon content up to 1934 $m^2/g$ (80.1% micropore) for RFN30-1100C (Table 2). The increase in surface area was consistent with the observed decrease in crystallite size. See Dresselhaus, M. S. et al. New characterization techniques for activated carbon fibers. *Carbon N. Y.* 30, 1065-1073 (1992), which is incorporated by reference. Electrical conductivity decreased with increasing organosilicon content, commensurate with the loss of π-electron delocalization (Table 2).

Applications of Biotemplated Carbon Nanofibers

Figure 4A:
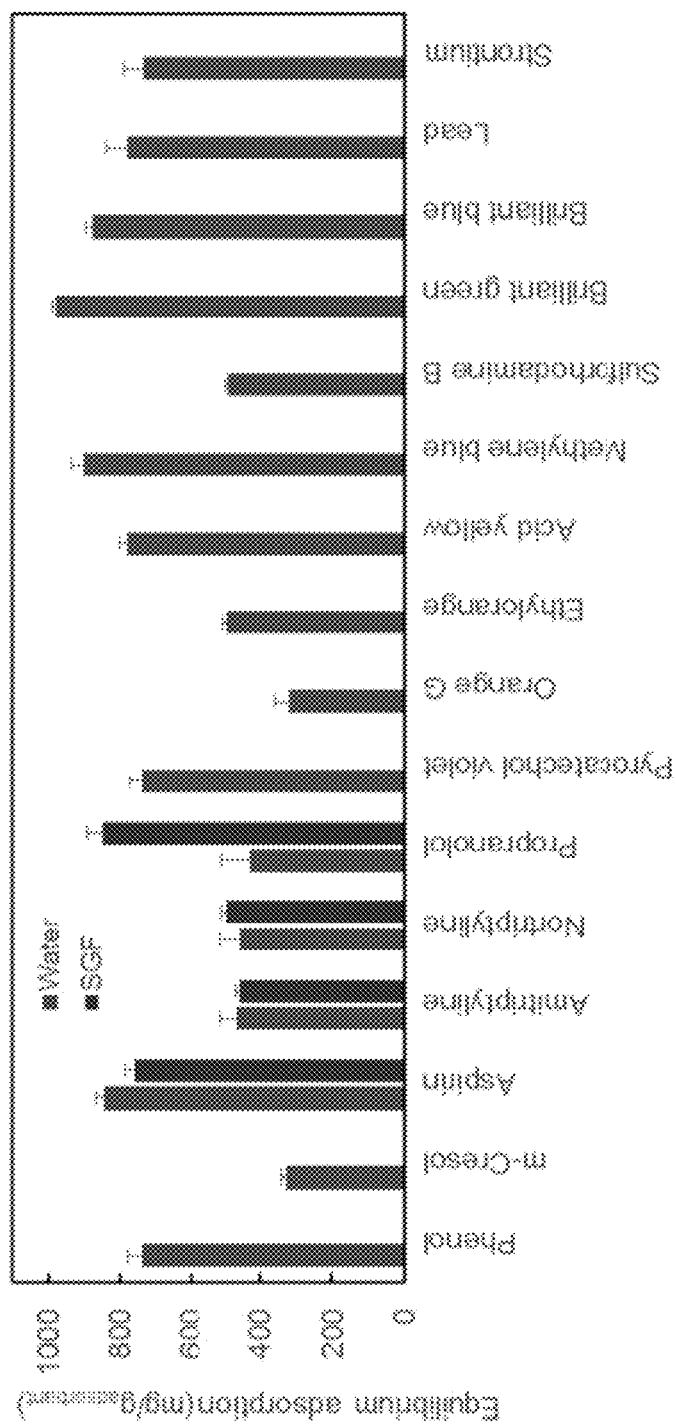
FIGS. 4A-4D show adsorption data for RFN30-1100C.
Figure 4B:
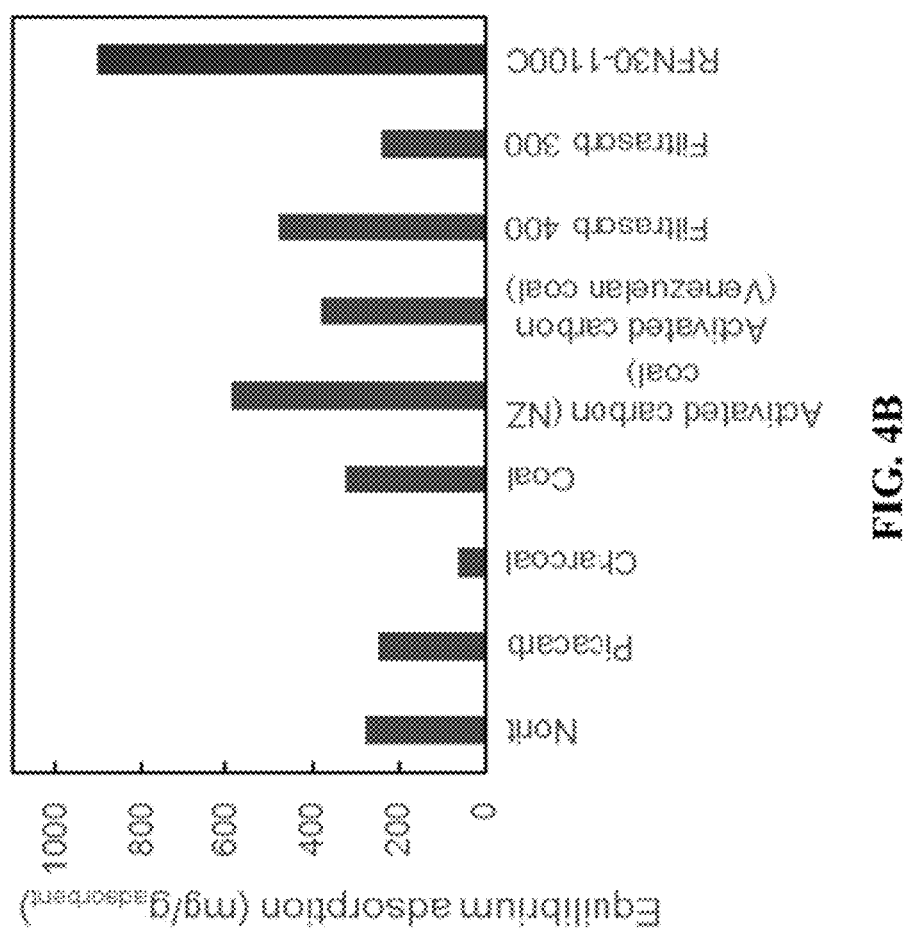
Figure 4C:
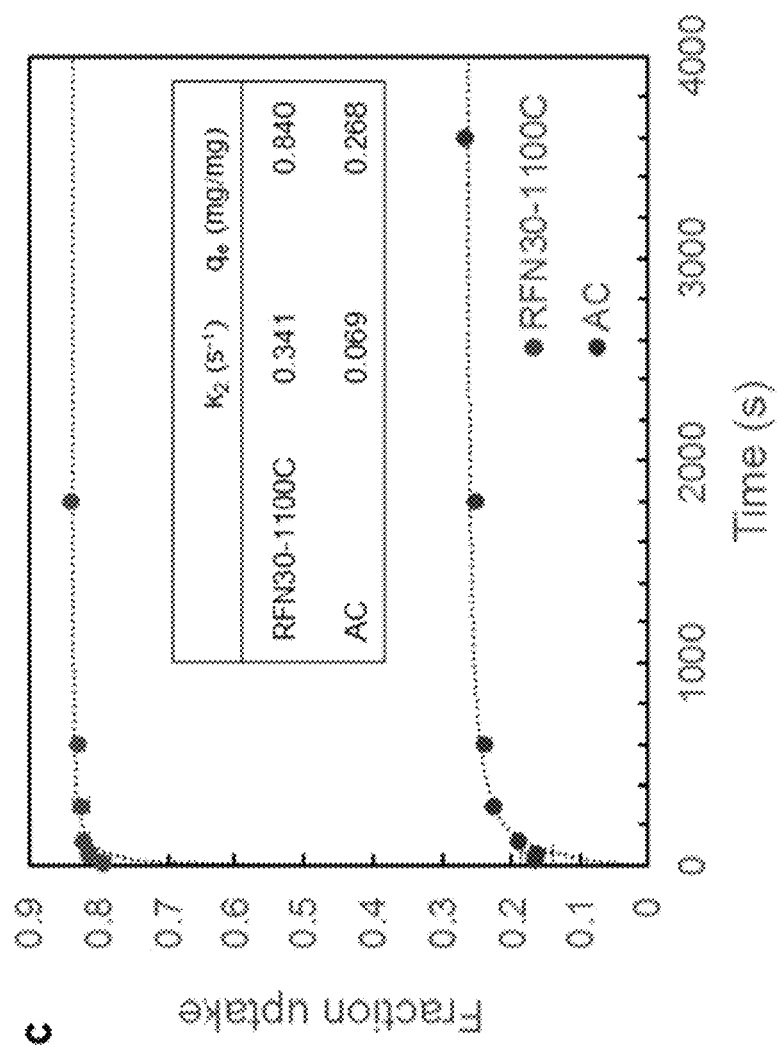
Figure 4D:
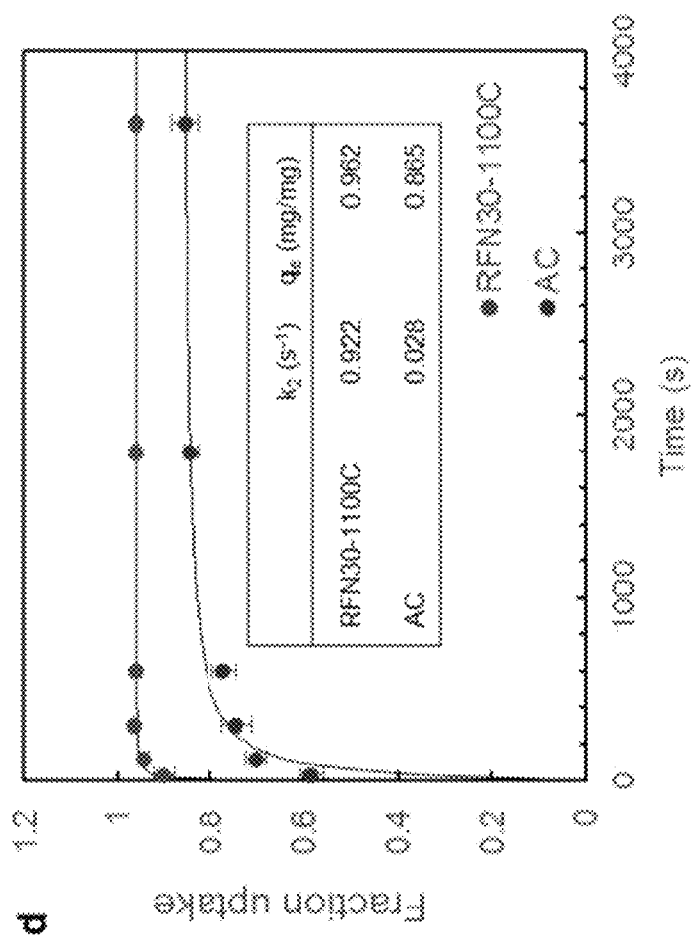

Due to their high surface area and low cost, microporous carbons have long been the preferred adsorbents to remove organic micropollutants (small molecules) and heavy ions in industrial waste water remediation, and to remove pharmaceutic toxins in the gastric tract to treat drug overdoses. See Dargan, P. I. An evidence based flowchart to guide the management of acute salicylate (aspirin) overdose. *Emerg. Med. J.* 19, 206-209 (2002), and Juurlink, D. N. Activated charcoal for acute overdose: A reappraisal. *Br. J. Clin. Pharmacol.* 81, 482-487 (2016), each of which is incorporated by reference in its entirety. Here, biotemplated carbon nanofibers (RFN30-1100C) can rapidly adsorb small molecules at up to 30 times the rate of commercial carbon adsorbents, and show significant uptake values for a range of organic pollutants including phenolic compounds, heavy metals (e.g. $Pb^{2+}$, $Sr^{2+}$), organophosphates (e.g. pesticides, insecticides), chemical warfare agents (e.g. sarin gas, mustard gas), organic dyes, gases (carbon dioxides, methane) and pharmaceutic molecules (FIG. 4A). Most adsorption data was taken in distilled water; adsorption for pharmaceutics was also studied in simulated gastric fluid (SGF) to reflect physiological conditions. The initial concentration of all substrates was 1 mg/mL. Uptake for all substrates tested was above 400 mg/g, with the exception of m-cresol and the orange G dye. The maximum uptake for methylene blue (the prototypical dye used for evaluating the adsorptive properties of carbon) was 902 mg/g, which exceeded the uptake of most commercial carbons by 1~2 fold and is amongst the highest values recorded (FIG. 4B). Adsorption data for commercial carbons are taken from the literature. See Rafatullah, M., Sulaiman, O., Hashim, R. & Ahmad, A. Adsorption of methylene blue on low-cost adsorbents: A review. *J. Hazard. Mater.* 177, 70-80 (2010), which is incorporated by reference in its entirety. Because adsorption rate is diffusion limited, the characteristic diffusion length could be tuned by reducing nanofiber diameter to ~20 nm (diffusion length $\sim d^{1/2}$) and allow for rapid adsorption. The adsorption rate for RFN30-1100C was comparable to the best rapid adsorbing polymers. See Alsbaiee, A. et al. Rapid removal of organic micropollutants from water by a porous β-cyclodextrin polymer. *Nature* 529, 190-194 (2016), which is incorporated by reference in its entirety. For example, when a 1:1 mass ratio of carbon nanofibers was added to a 1 mg/mL methylene blue solution, 79% of the dye (88% of the equilibrium uptake) was removed within ~15 s and 84% (93% of equilibrium uptake) within 1 minute (FIG. 4C). At 0.25 mg/mL, methylene blue completely discolored immediately upon shaking. In comparison, commercial activated charcoal removed 16% (52% of equilibrium uptake) of the dye after 1 minute, only reaching 85% of its equilibrium uptake (314 mg/g) at 1 hour. An important application of a rapid adsorbent is in the gastric decontamination of drug overdoses. Currently, gastric decontamination relies on ingesting activated charcoal at a dosage of 40 mg charcoal per 1 mg drug intake with limited effectiveness that is highly time-dependent. For example, the degree of decontamination decreased from 74.10% when administered within 5 minutes of overdose to 51.70% at 30 minutes and 38.14% at 60 minutes. See Chyka, P. A., Seger, D., Krenzelok, E. P. & Vale, J. A. Position Paper: Single-Dose Activated Charcoal. *Clin. Toxicol.* 43, 61-87 (2005), which is incorporated by reference in its entirety. Propranolol, a prototypical β-blocker with high overdose rate, was used as a model substrate. See Mowry, J. B., Spyker, D. A., Brooks, D. E., Zimmerman, A. & Schauben, J. L. 2015 Annual Report of the American Association of Poison Control Centers' National Poison Data System (NPDS): 33rd Annual Report. *Clin. Toxicol.* 54, 924-1109 (2016), which is incorporated by reference in its entirety. At a dosage of 4 mg carbon nanofibers per mg propranolol, a maximum of 96% reduction in propranolol concentration was recorded with 2 minutes. In comparison, a maximum reduction of 86% was reached only after 30~60 minutes using commercial activated charcoal. Adsorption kinetics was modeled using pseudo-second order kinetics. See Hameed, B. H., Din, A. T. M. & Ahmad, A. L. Adsorption of methylene blue onto bamboo-based activated carbon: Kinetics and equilibrium studies. *J. Hazard. Mater.* 141, 819-825 (2007), which is incorporated by reference in its entirety. For methylene blue, the second order rate constant was ~5 times higher for RFN30-1100C than the activated charcoal control. For propranolol, this value was ~30 times higher (FIG. 4D). Carbon dosage of 1 mg/mL was used for all tests.

Figure 5A:
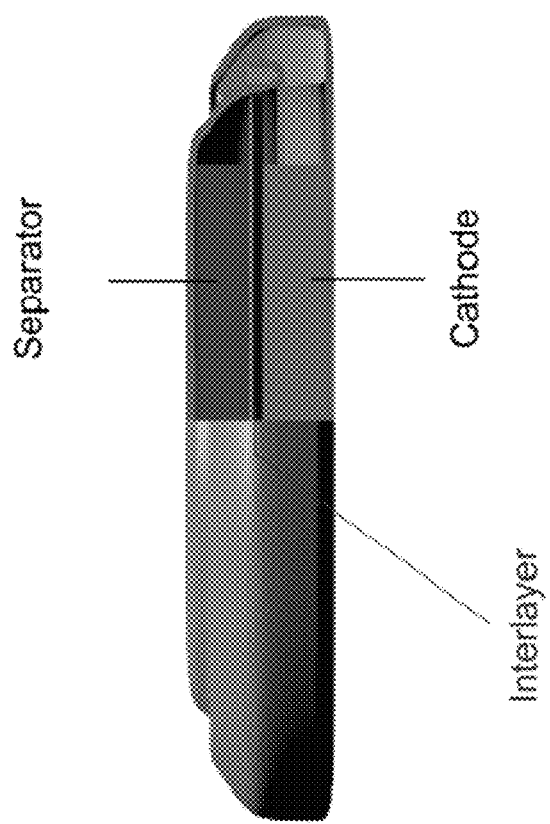
FIGS. 5A-5E shows electrochemical data showing improved lithium-sulfur battery performance using a biotemplated carbon nanofiber interlayer. A schematic for the cell assembly is shown in FIG. 5A. The EIS spectra of lithium-sulfur cells with and without interlayer are shown in FIG. 5B.
Figure 5B:
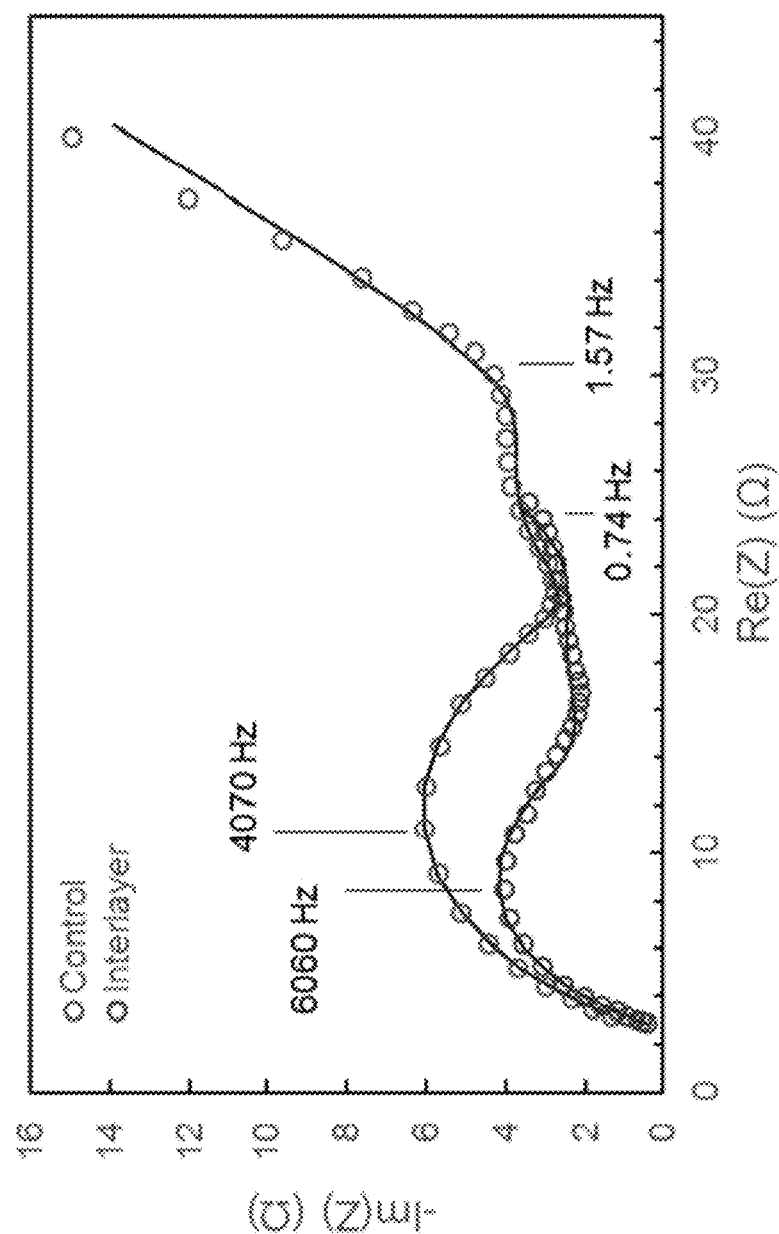
Figure 5C:
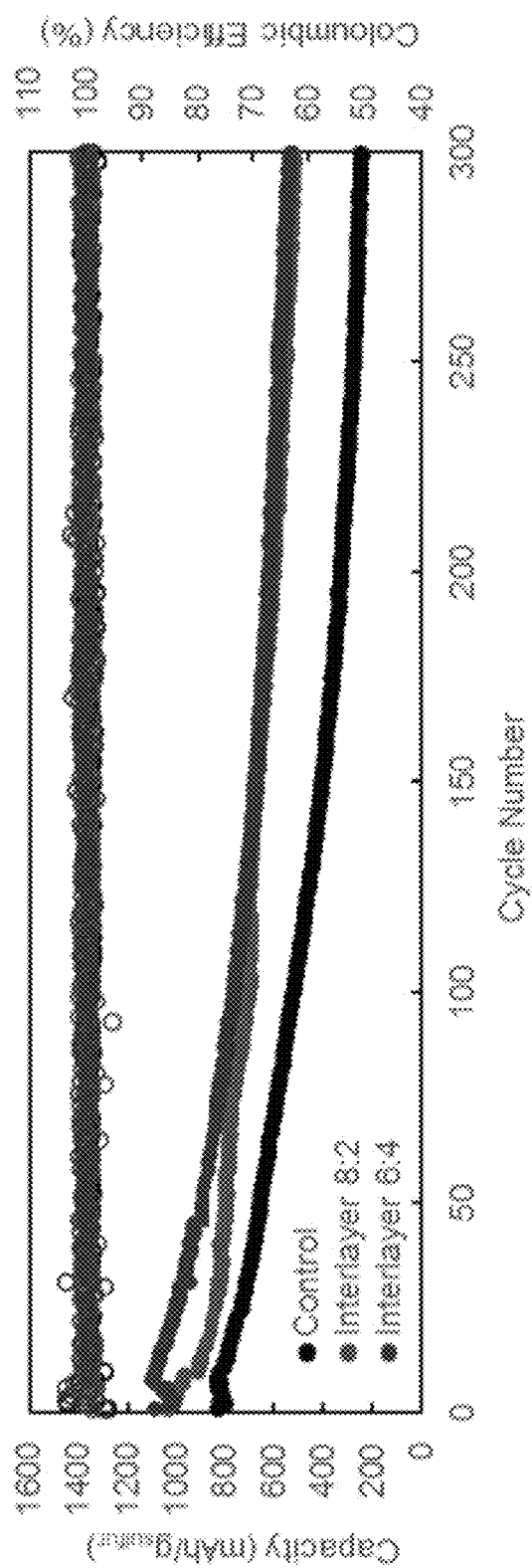
Figure 5D:
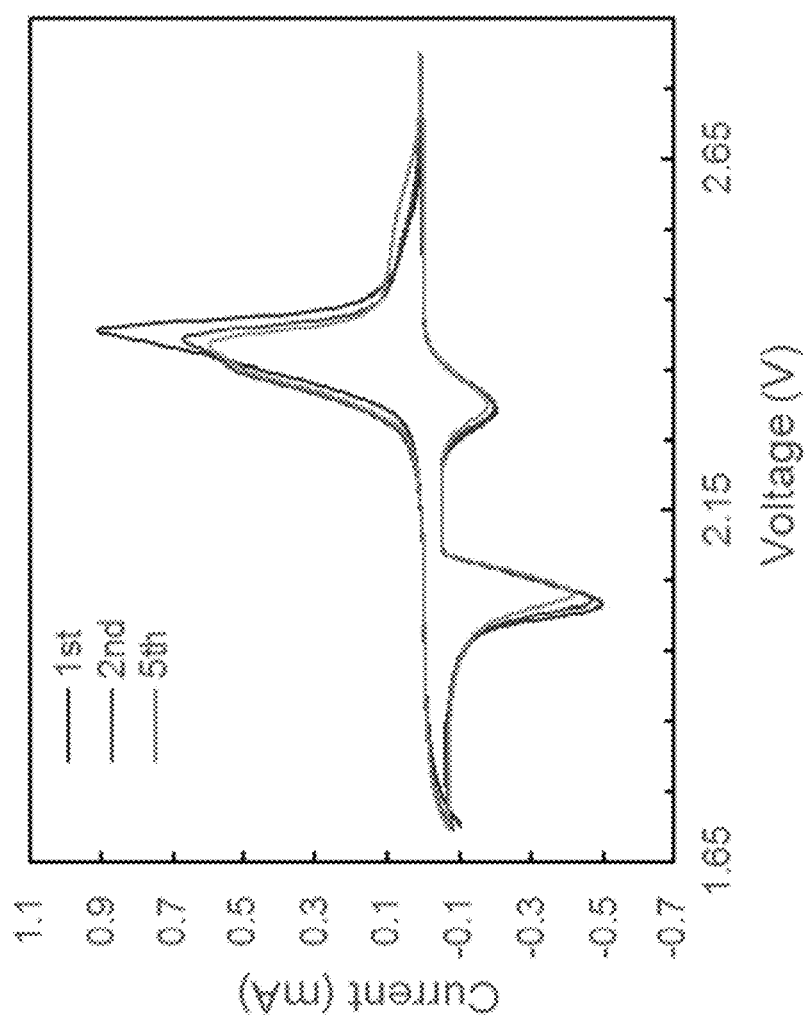
Figure 5E:
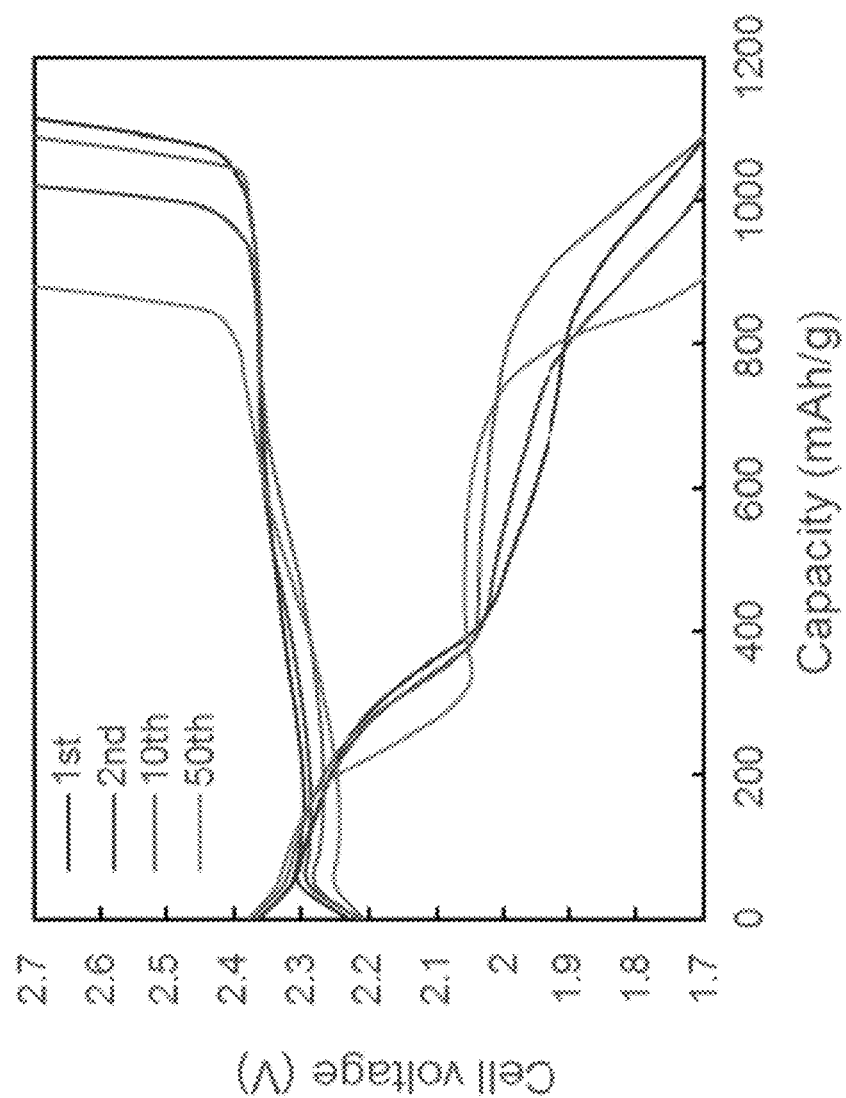
Figure 12:
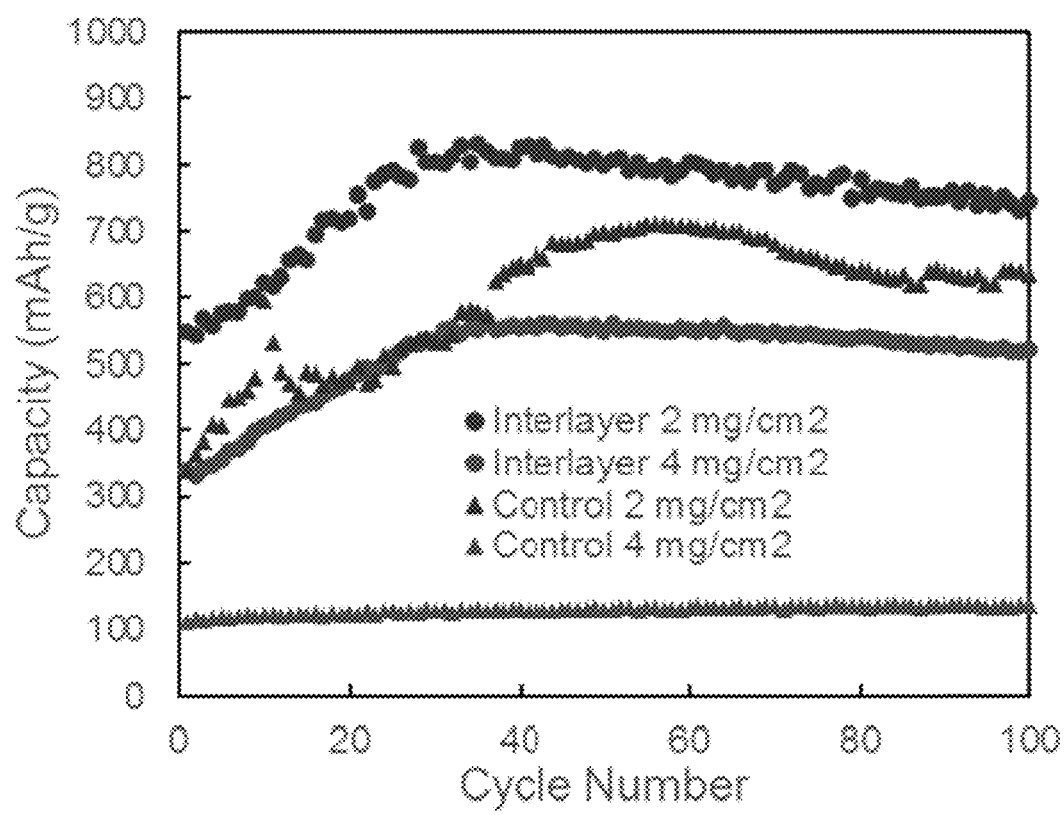
FIG. 12 shows galvanostatic cycling of thick lithium-sulfur electrodes (2 $mg/cm^2$ and 4 $mg/cm^2$ loading) with and without interlayer.
Figure 13:
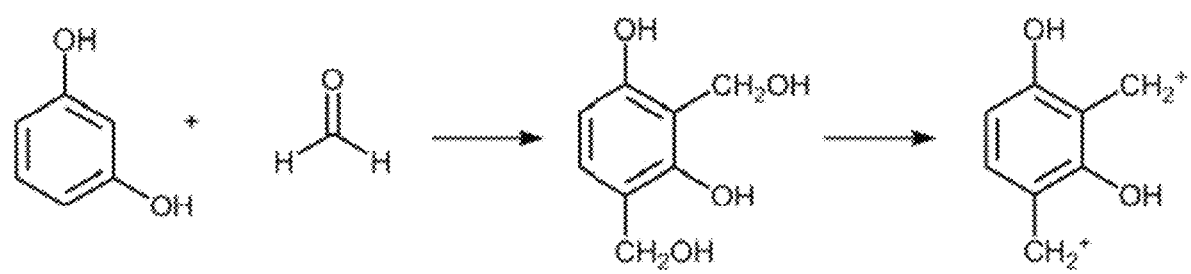
FIG. 13 shows addition of formaldehyde to a resorcinol molecule.
Figure 14:
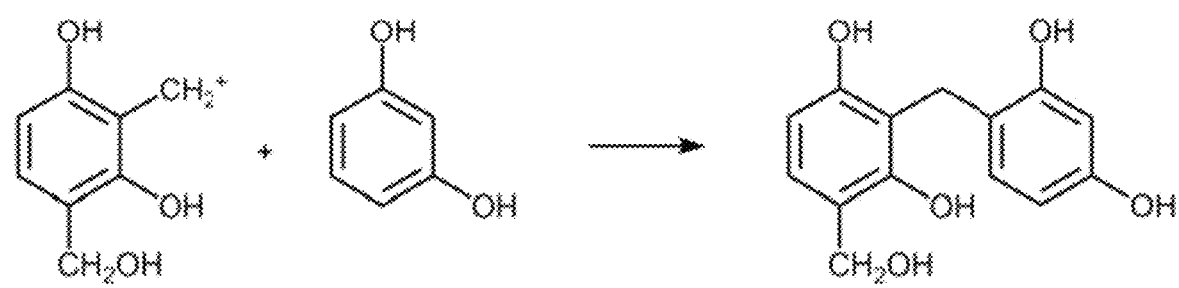
FIG. 14 shows condensation of resorcinol to form a methylene bridge.
Figure 15:
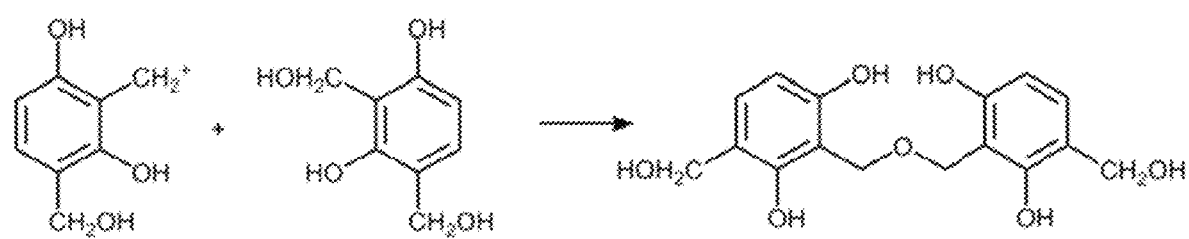
FIG. 15 shows condensation of resorcinol to form an ether bridge.
Figure 16:
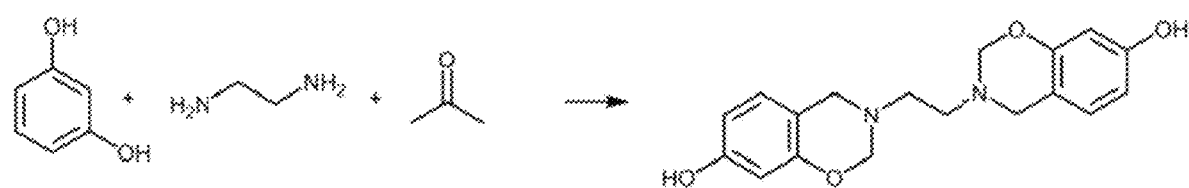
FIG. 16 shows reaction of resorcinol, formaldehyde and ethylenediamine to form benzoxazine bridges by Mannich condensation.

Microporous carbons have also been extensively studied for lithium-sulfur batteries. See Xu, Y. et al. Confined Sulfur in Microporous Carbon Renders Superior Cycling Stability in Li/S Batteries. *Adv. Funct. Mater.* 25, 4312-4320 (2015), Wei, S. et al. A stable room-temperature sodium-sulfur battery. *Nat. Commun.* 7, 1-10 (2016), Yin, Y.-X. X., Xin, S., Guo, Y.-G. G. & Wan, L.-J. J. Lithium-sulfur batteries: Electrochemistry, materials, and prospects. *Angew. Chemie—Int. Ed.* 52, 13186-13200 (2013), and Seh, Z. W., Sun, Y., Zhang, Q. & Cui, Y. Designing high-energy lithium-sulfur batteries. *Chem. Soc. Rev.* 45, 5605-5634 (2016), each of which is incorporated by reference in its entirety. Lithium-sulfur batteries are widely considered the most likely candidate for next generation lithium-ion batteries, due to its promise of 5 times higher specific gravimetric energy compared to the state-of-the-art cobalt oxide-based lithium-ion cells. See Yin, Y.-X. X., Xin, S., Guo, Y.-G. G. & Wan, L.-J. J. Lithium-sulfur batteries: Electrochemistry, materials, and prospects. *Angew. Chemie—Int. Ed.* 52, 13186-13200 (2013), which is incorporated by reference in its entirety. Having an electroactive component in sulfur also offers important cost advantages (price of sulfur is $0.04 per pound compared to $11.90 per pound for cobalt). See Seh, Z. W., Sun, Y., Zhang, Q. & Cui, Y. Designing high-energy lithium-sulfur batteries. *Chem. Soc. Rev.* 45, 5605-5634 (2016), Ma, L., Hendrickson, K. E., Wei, S. & Archer, L. A. Nanomaterials: Science and applications in the lithium-sulfur battery. *Nano Today* 10, 315-338 (2015), and Ober, J. A. *Mineral commodity summaries 2017. Mineral Commodity Summaries* (2017), each of which is incorporated by reference in its entirety. A typical cell comprises a sulfur cathode and a lithium anode. On discharge, the sulfur converts to lithium sulfide via various polysulfide intermediates. Long chain polysulfides such as $S_8^{2-}$ and $S_6^{2-}$, in particular, dissolve rapidly the in the organic electrolyte. When unconstrained, these polysulfides shuttle to the anode by diffusive and electrophoretic forces, react with the lithium anode both chemically and electrochemically (during recharge), then shuttle back to the cathode in a parasitic cycle. See Yin, Y.-X. X., Xin, S., Guo, Y.-G. G. & Wan, L.-J. J. Lithium-sulfur batteries: Electrochemistry, materials, and prospects. *Angew. Chemie—Int. Ed.* 52, 13186-13200 (2013), which is incorporated by reference in its entirety. This shuttling mechanism is detrimental to sulfur utilization, leads to poor Coulombic efficiency and rapid capacity decay. The conundrum is that the electroactivity of lithium-sulfur cell relies in part on the solubility of polysulfides, which enables a solid-to-liquid-to-solid reaction pathway that circumvents poor solid state lithium transport in sulfur and lithium sulfide. See Fan, F. Y., Carter, W. C. & Chiang, Y.-M. Mechanism and Kinetics of $Li_2S$ Precipitation in Lithium-Sulfur Batteries. *Adv. Mater.* 27, 5203-5209 (2015), which is incorporated by reference in its entirety. Therefore, it is crucial to localize polysulfide dissolution to simultaneously enable electrochemical activity while mitigating shuttling. See Yang, Y., Zheng, G. & Cui, Y. Nanostructured sulfur cathodes. *Chem. Soc. Rev.* 42, 3018-3032 (2013), which is incorporated by reference in its entirety. One promising strategy was to insert a carbon interlayer between a cathode and a separator. The interlayer functions as a secondary current collector, which cuts electron transport distance in the axial direction. It has also been hypothesized to increase capacity by adsorbing and reutilizing dissolved polysulfides. See Su, Y.-S. & Manthiram, A. Lithium-sulphur batteries with a microporous carbon paper as a bifunctional interlayer. *Nat. Commun.* 3, 1166 (2012), Wang, L. et al. A lightweight multifunctional interlayer of sulfur-nitrogen dual-doped graphene for ultrafast, long-life lithium-sulfur batteries. *J. Mater. Chem. A* 4, 15343-15352 (2016), Kong, W. et al. Ultrathin MnO2/Graphene Oxide/Carbon Nanotube Interlayer as Efficient Polysulfide-Trapping Shield for High-Performance Li—S Batteries. *Adv. Funct. Mater.* (2017), Hwang, J. Y. et al. High-Energy, High-Rate, Lithium-Sulfur Batteries: Synergetic Effect of Hollow TiO2-Webbed Carbon Nanotubes and a Dual Functional Carbon-Paper Interlayer. *Adv. Energy Mater.* 6, 1-7 (2016), Singhal, R., Chung, S., Manthiram, A. & Kalra, V. A free-standing carbon nanofiber interlayer for high-performance lithium-sulfur batteries. *J. Mater. Chem. A Mater. energy Sustain.* 3, 4530-4538 (2015), Balach, J., Jaumann, T., Klose, M., Eckert, J. & Giebeler, L. Mesoporous Carbon Interlayers with Tailored Pore Volume as Polysulfide Reservoir for High-Energy Lithium-Sulfur Batteries. 1-8 (2015), and Wei, S., Choudhury, S., Tu, Z., Zhang, K. & Archer, L. A. Electrochemical Interphases for High-Energy Storage Using Reactive Metal Anodes. *Acc. Chem. Res.* acs.accounts.7b00484 (2017), each of which is incorporated by reference in its entirety. So far, the carbon-based interlayers employed had thicknesses in the range of 30~250 μm with mass loadings greater than 4 mg/cm², but this is at least as thick as a typical Celgard 2400 separator (~25 μm) and sometimes thicker than commercial cathodes (~100 μm). The need for a thick interlayer may in part be attributed to the poor accessibility of electroactive carbon surfaces due to ionic transport inside micropores. Biotemplated carbon nanofibers, with a combination of high surface area, small diameters and an openly accessible scaffold structure, would enable efficient utilization of the entire carbon surface area. To demonstrate this, the Celgard separator was coated with a dispersion of RFN10-1100C (which has a combination of high electrical conductivity and surface area) in lithiated Nafion solution to fabricate ultrathin interlayers, with thicknesses between 5~6 μm and carbon loading ~70 μg/cm²— which is up to 100 times less carbon than other reported interlayers. Id. In order to focus on the role of the interlayer, a standard sulfur electrode was prepared by mixing sulfur with Ketjen black (4:1 weight ratio). As expected, interface charge transfer resistance as measured by EIS decreased with the addition of the interlayer, commensurate with an effective reduction in the electron transport distance through the electrode (FIG. 5B). Both initial capacity (sulfur utilization) and capacity retention were improved with the addition of the interlayer (FIG. 5C). The control had an initial discharge capacity of 821 mAh/g at a discharge rate of 1 C. The discharge capacity increased to 1035 mAh/g, corresponding to an improvement of 26%, with the interlayer. Retained capacity after 300 cycles increased by 70% with the addition of the interlayer, from 242 mAh/g to 518 mAh/g. The voltage profiles remained stable through at least the first 300 cycles with the interlayer. An initial increase in the potential of the second discharge plateau was observed over the first 10 cycles with a corresponding decrease in cell polarization and increase in discharge capacity (FIGS. 5D and 5E). This effect has been well-documented and was attributed to electrode restructuring. The enhanced improvement in sulfur utilization was even more pronounced when thicker cathodes were used. For a cathode with 2 mg/cm$^2$ sulfur loading, the discharge capacity after 100 cycles increased by 43%, while a 78% increase was recorded for a 4 mg/cm$^2$ cathode (FIG. 12).

In sum, synthesis of highly uniform, ultrafine carbon nanofibers can be enabled by coupling biological and molecular templating. Biological templating enables precise control of morphology at the nanometer scale, while molecular templating allows control of carbon nanotexture and structure at the sub-nanometer scale. The synergistic control of structure and properties at multiple length-scales makes this approach particularly versatile. The practical utility of biotemplated carbon nanofibers was demonstrated in the rapid adsorption of small molecules and in lithium-sulfur batteries, taking advantage of their morphology, physical properties and 3-dimensional assembly.

Resorcinol-Formaldehyde Synthesis.

Concentrated precursor solutions were freshly prepared immediately before synthesis according to Supplementary Table 1. In a typical large-scale reaction, 2 L of virus suspension at a concentration of 3.2×10$^{11}$ pfu/mL was preheated to ~50° C. Precursor solutions were then added to the virus suspension under vigorous stirring. The volume of precursors added depended on the final polysiloxane content and was adjusted according to Supplementary Table 2. After thorough mixing of precursors, the suspension was transferred to an oven and incubated at 80° C. overnight. After the reaction, nanofiber precipitates were collected by filtering over a 0.2 μm membrane, and thoroughly rinsed with distilled water then lyophilized.

Carbon Nanofiber Synthesis.

The lyophilized nanofibers were carbonized at a set temperature (800° C., 1100° C. or 1400° C.) for at least 4 hours in flowing Argon, with a heating rate of 2° C./min. The carbonized nanofibers were then etched in 2 M sodium hydroxide at 80° C. overnight. After etching, the carbon nanofibers were thoroughly rinsed using distilled water over a 0.2 μm filter until the rinse water reached neutral pH, to indicate that all sodium hydroxide was removed.

Imaging.

Transmission electron microscopy (TEM) was carried out using the FEI Tecnai G2 and the JEOL 2010 High Resolution microscopes at 120 kV and 200 kV, respectively. The Image J software was used to process the images. To improve the clarity of carbon textures, images were with Fast Fourier Transform and the image brightness/contrast were adjusted. No further imaging processing was done. Scanning transmission electron microscopy (STEM) and energy dispersive x-ray spectroscopy (EDX) line-scans were carried out using the JEOL 2010F High Resolution at 200 kV.

Chemical/Surface Characterization.

Fourier-transform infrared spectroscopy (FTIR) was carried out using the Bruker Lumos FTIR in ATR mode. A background correction was used and $CO_2/H_2O$ peaks were corrected. X-ray electron spectroscopy (XPS) spectra were collected using the Thermo Scientific K-Alpha and Thermo Scientific K-Alpha+systems. An ion flood gun was used for all samples, and the peaks were charge corrected by setting the aliphatic C1s peak to 284.6 eV. All peaks were fitted using Voigt profiles (Gaussian:Lorentzian ratio 7:3). Raman spectra were obtained using the Horiba LabRam HR800 using a 532 nm light source.

Structural Characterization.

X-ray diffractometry (XRD) was carried out using the Panalytical X'Pert Pro Multipurpose Diffractometer. Data was collected in the Bragg-Brentano geometry between 10° and 60° 2θ using a copper anode, and using an automatic divergence slit. Wide-angle x-ray scattering (WAXS) experiments were conducted using the Rigaku H3R with Bruker Nanostar system. Samples were embedded in Kapton tape, and the Kapton tape background was subtracted after measurement.

Physical Characterization.

Brunauer-Emmett-Teller (BET) measurements were obtained using the Micromeritics ASAP 2020. Pore size distribution was determined using DFT calculations and micropore contributions were estimated using the t-plot method. Thermogravimetric analysis (TGA) and differential scanning calorimetry (DSC) were carried out using the TA Instruments Discovery systems. TGA thermograms were obtained under nitrogen, using a linear ramp mode (10° C./min) from 40° C. to 800° C. DSC was obtained using a linear ramp cycle from 40° C. to 300° C. and back.

Electrical Conductivity.

Electrical conductivity was measured for carbon nanofiber films. The films were made by mixing carbon with Teflon 8A in a 9:1 weight ratio using mortar and pestle, then rolled into films of thickness ≤100 μm. Because of the low density of the nanofiber powder, it was not possible to prepare the thin film sample of pure carbon. The 4-point probe sheet resistance was then measured using the Keithley SCS-4200 instrument with probe spacing of 1.27 mm, and resistivity calculated by:

$$\rho = 4.5324 t \left(\frac{v}{i}\right)$$

Where ρ is the resistivity in Ω·cm, t is the film thickness in cm, v/i is the voltage/current slope in V/A., Adsorption and Neutralization of Toxic Compounds Toxic compounds can be micropollutants, toxic industrial chemicals (TICs) and chemical warfare agents (CWAs). These chemicals can pose significant risks to human health. The most salient example is chemical warfare agents (CWAs), which are man-made chemicals that have been used for the mass destruction of human life. These include blistering agents such as 2,2'-dichloro diethyl sulfide (distilled mustard, HD), and nerve agents such as (RS)—O-isopropyl methylphosphonofluoridate (Sarin, GB) and O-pinacolyl methylphosphonofluoridate (Soman, GD). The acute toxicities of CWAs can result in symptoms and potential death within minutes of exposure, and are therefore incredibly dangerous to both military personnel and civilians. See, e.g., Russell, A. J., Berberich, J. A., Drevon, G. F. & Koepsel, R. R. Biomaterials for Mediation of Chemical and Biological Warfare Agents. *Annu. Rev. Biomed. Eng.* 5, 1-27 (2003), which is incorporated by reference herein. Another prevalent example is toxic industrial chemicals (TICs) such as ammonia, hydrogen sulfide, sulfur dioxide and chlorine. These gaseous chemicals are manufactured in massive quantities for use in industrial processes, and accidental release of these chemicals into the environment presents a significant risk to chemical workers. Some TICs are also released to the environment through human activities such as burning fossil fuel, and contribute to the depletion of the ozone layer and global warming. See, e.g., Bobbitt, N. S. et al. Metal-organic frameworks for the removal of toxic industrial chemicals and chemical warfare agents. *Chem. Soc. Rev.* 46, 3357-3385 (2017), which is incorporated by reference herein.

A third example of toxic chemicals is water soluble micropollutants such as organic dyes, pharmaceutics and heavy ions. These pollutants are common industrial run offs, and pose significant risks of contaminating drinking waters and the aquatic food chain.

The large variety of chemical threats necessitates the development of sorbent materials that are universally effective, and not overly chemical specific. Currently, activated carbons are perhaps the most widely used materials for chemical removal, because they combine lightweight with high surface area. See, e.g., Smith, S. C. & Rodrigues, D. F. Carbon-based nanomaterials for removal of chemical and biological contaminants from water: A review of mechanisms and applications. *Carbon N. Y.* 91, 122-143 (2015), which is incorporated by reference herein. As such, they are ubiquitously found in protective equipment such as gas masks and protective clothing. Nevertheless, the range of chemicals that can be removed using activated carbons is limited. Because activated carbons predominantly rely on relatively weak physical adsorption and not reactive mechanisms, they are generally ineffective at filtering gases of high vapor pressure. The lack of inherent reactivity is also problematic when activated carbons are used to filter CWAs. For this application, the lack of a self-decontaminating mechanism would result in a concentrating effect that eventually may lead to persistent desorption of these chemicals. See, e.g., Russell, A. J., Berberich, J. A., Drevon, G. F. & Koepsel, R. R. Biomaterials for Mediation of Chemical and Biological Warfare Agents. *Annu. Rev. Biomed. Eng.* 5, 1-27 (2003), which is incorporated by reference herein. In practice, carbon sorbents must be impregnated with reactive additives to compensate for this shortcoming. See, e.g., Linders, M. J. G., Mallens, E. P. J., Van Bokhoven, J. J. G. M., Kapteijn, F. & Moulijn, J. A. Breakthrough of shallow activated carbon beds under constant and pulsating flow. *Am. Ind. Hyg. Assoc. J.* 64, 173-180 (2003). Furthermore, the low surface charge density of activated carbons results in a lack of electrostatic interactions, which also limits their ability to adsorb ionic compounds. See, e.g., Smith, S. C. & Rodrigues, D. F. Carbon-based nanomaterials for removal of chemical and biological contaminants from water: A review of mechanisms and applications. *Carbon N. Y.* 91, 122-143 (2015), which is incorporated by reference herein. Lastly, poor diffusion through carbons with large mesh sizes limits their utilization under dynamic flow conditions.

Figure 23:
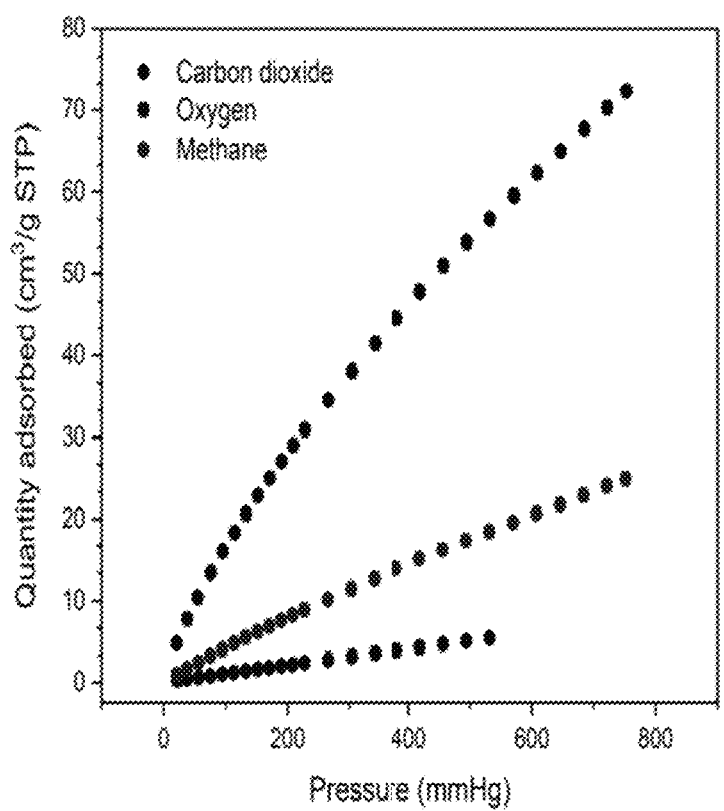
FIG. 23 shows the quantity of carbon dioxide, oxygen and methane absorbed as a function of pressure.
Figure 24:
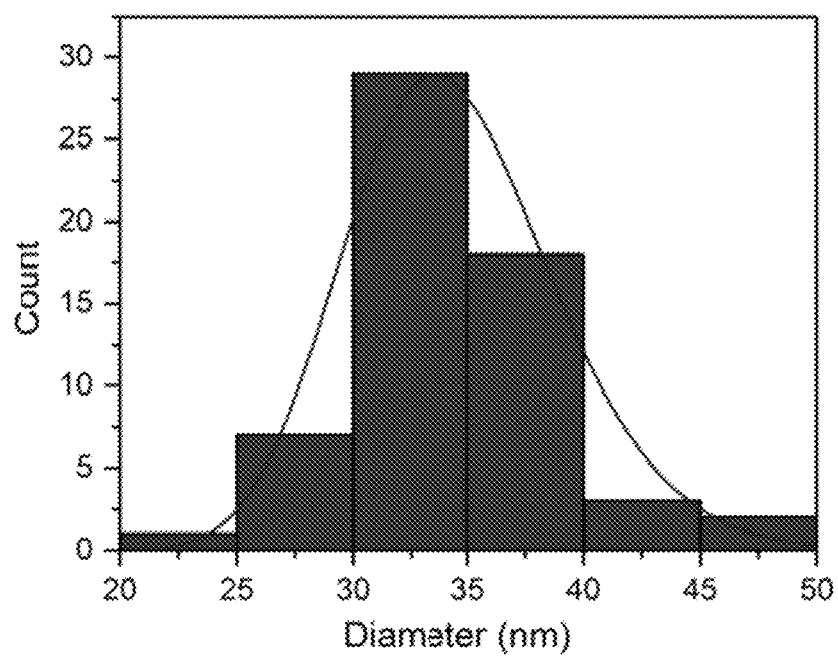
FIG. 24 shows a histogram of the distribution of RFN diameters (n=60). Average diameter is 34.5 nm with a standard deviation of 4.6 nm.
Figure 25:
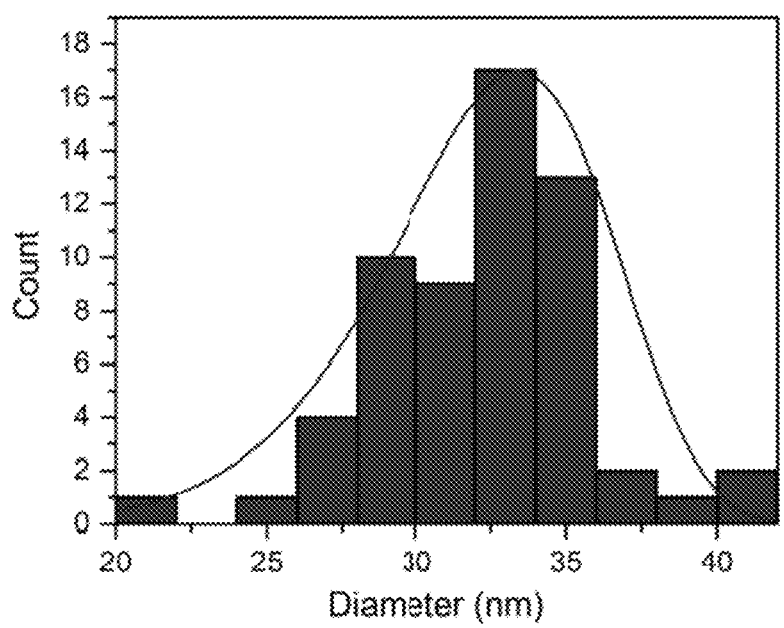
FIG. 25 shows a histogram of the distribution of RFN10 diameters (n=60). Average diameter is 32.2 nm with a standard deviation of 3.7 nm.
Figure 26:
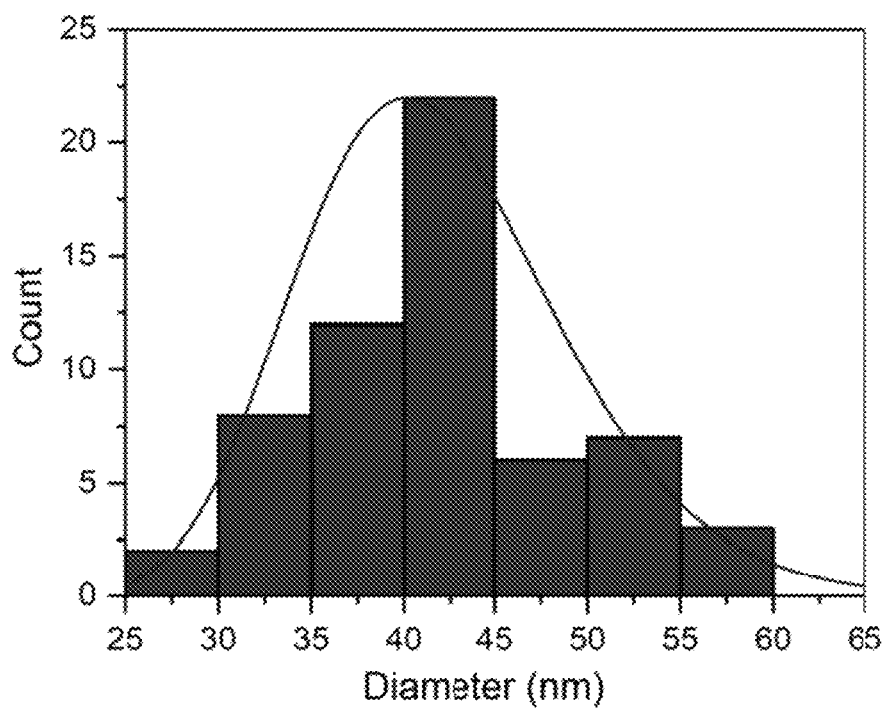
FIG. 26 shows a histogram of the distribution of RFN30 diameters (n=60). Average diameter is 41.9 nm with a standard deviation of 7.2 nm.
Figure 27:
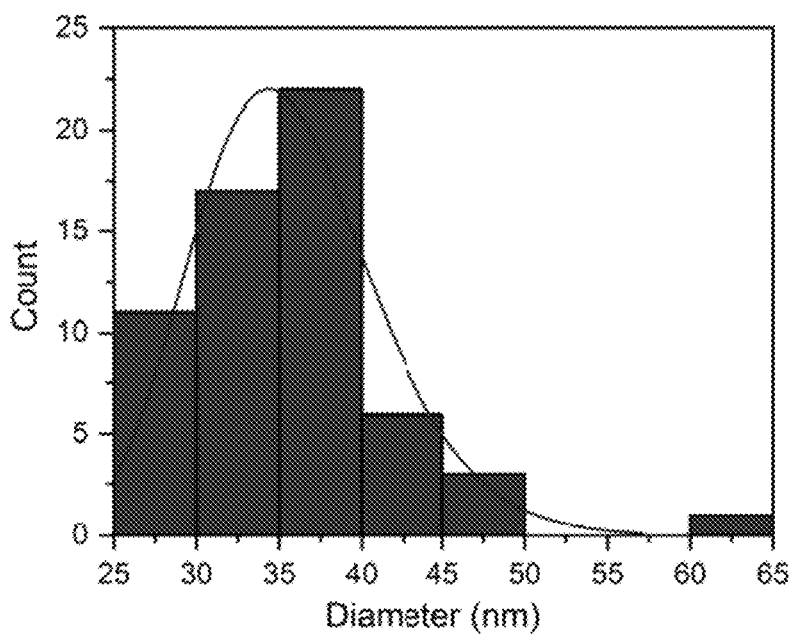
FIG. 27 shows a histogram of the distribution of RFN50 diameters (sample size 60). Average diameter is 35.7 nm with a standard deviation of 5.9 nm.

Referring to FIG. 23, this graph shows a comparison of the quantity of carbon dioxide, oxygen and methane absorbed as a function of pressure.

Figure 17:
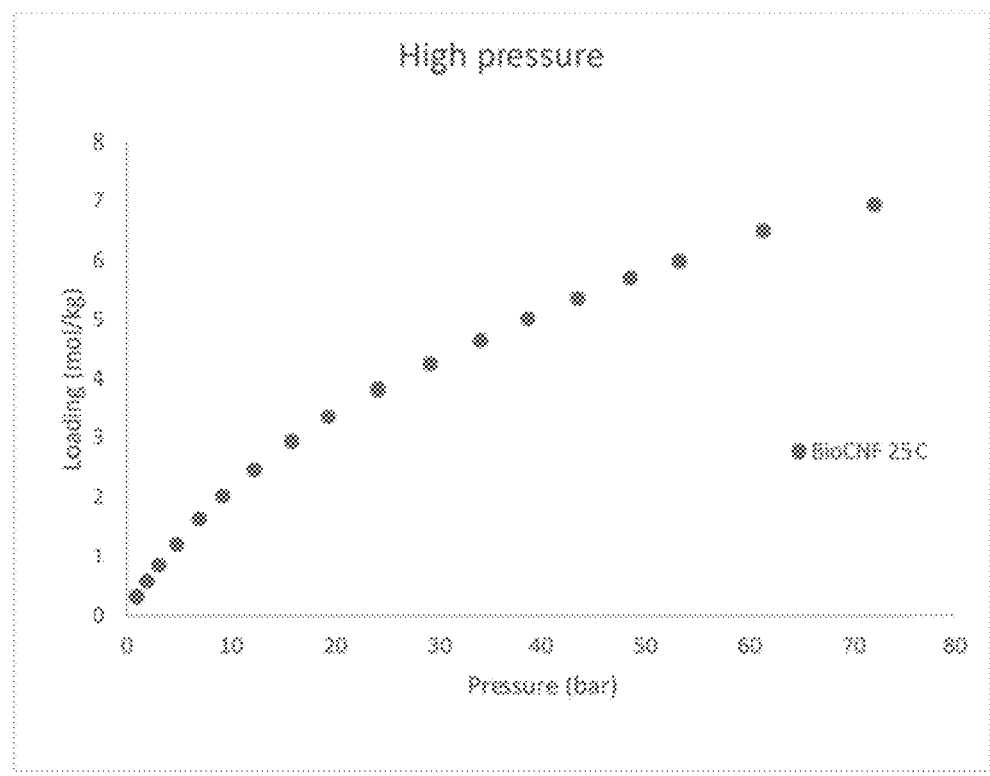
FIGS. 17-18 show the adsorption/storage of oxygen and methane at high pressures.
Figure 18:
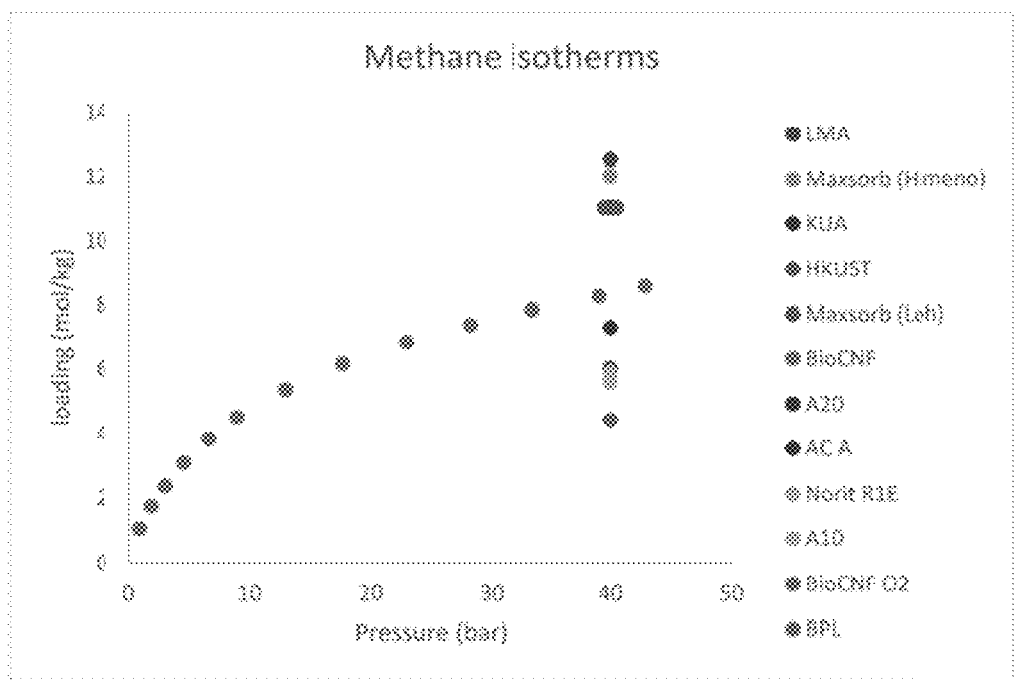

Referring to FIGS. 17-18, these graphs show the adsorption/storage of oxygen and methane at high pressures. The claimed material compares well against other materials used for oxygen and methane storage. FIG. 17 shows pressure loading of oxygen (25 degree C.). FIG. 18 shows high pressure loading of methane using our material compared against other methane storage materials (25 degree C.).

Electrochemistry

Microporous carbons have also been extensively studied for lithium-sulfur batteries. See, e.g., Dresselhaus, M. S. et al. New characterization techniques for activated carbon fibers. *Carbon N. Y.* 30, 1065-1073 (1992), which is incorporated by reference herein. Lithium-sulfur batteries are widely considered the most likely candidate for next generation lithium-ion batteries, due to its promise of 5 times higher specific gravimetric energy compared to the state-of-the-art cobalt oxide-based lithium-ion cells. See, e.g., Ferrari, A. C. & Robertson, J. Interpretation of Raman spectra of disordered and amorphous carbon. *Phys. Rev. B* 61, 95-107 (2000), which is incorporated by reference herein. Having an electroactive component in sulfur also offers important cost advantages (price of sulfur is $0.04 per pound compared to $11.90 per pound for cobalt). See, e.g., Li, Z. Q., Lu, C. J., Xia, Z. P., Zhou, Y. & Luo, Z. X-ray diffraction patterns of graphite and turbostratic carbon. *Carbon N. Y.* 45, 1686-1695 (2007), which is incorporated by reference herein. A typical cell comprises a sulfur cathode and a lithium anode. On discharge, the sulfur converts to lithium sulfide via various polysulfide intermediates. Long chain polysulfides such as $S_8^{2-}$ and $S_6^{2-}$, in particular, dissolve rapidly the in the organic electrolyte. When unconstrained, these polysulfides shuttle to the anode by diffusive and electrophoretic forces, react with the lithium anode both chemically and electrochemically (during recharge), then shuttle back to the cathode in a parasitic cycle. See, e.g., Ferrari, A. C. & Robertson, J. Interpretation of Raman spectra of disordered and amorphous carbon. *Phys. Rev. B* 61, 95-107 (2000), which is incorporated by reference herein. This shuttling mechanism is detrimental to sulfur utilization, leads to poor Coulombic efficiency and rapid capacity decay. The conundrum is that the electroactivity of lithium-sulfur cell relies in part on the solubility of polysulfides, which enables a solid-to-liquid-to-solid reaction pathway that circumvents poor solid state lithium transport in sulfur and lithium sulfide. See, e.g., Inagaki, M. & Kang, F. Fundamental Science of Carbon Materials. in *Materials Science and Engineering of Carbon: Fundamentals* 17-217 (2014). doi:10.1016/B978-0-12-800858-4.00002-4, which is incorporated by reference herein. Therefore, it is crucial to localize polysulfide dissolution to simultaneously enable electrochemical activity while mitigating shuttling. See, e.g., Liang, C., Li, Z. & Dai, S. Mesoporous carbon materials: Synthesis and modification. *Angew. Chemie—Int. Ed.* 47, 3696-3717 (2008), which is incorporated by reference herein. One promising strategy was to insert a carbon interlayer between the cathode and separator (FIG. 5A). The interlayer functions as a secondary current collector, which cuts electron transport distance in the axial direction. It has also been hypothesized to increase capacity by adsorbing and reutilizing dissolved polysulfides. See, e.g., Dresselhaus, M. S. NT10: Recent advances in carbon nanotube science and applications. ACS Nano 4, 4344-4349 (2010), which is incorporated by reference herein. So far, the carbon-based interlayers employed had thicknesses in the range of 30~250 μm with mass loadings greater than 4 mg/cm$^2$, but this is at least as thick as a typical Celgard 2400 separator (~25 μm) and sometimes thicker than commercial cathodes (~100 μm). The need for a thick interlayer may in part be attributed to the poor accessibility of electroactive carbon surfaces due to ionic transport inside micropores.

Demonstration of Efficacy

Biotemplated carbon nanofibers, with a combination of high surface area, small diameters and an openly accessible scaffold structure, can enable efficient utilization of the entire carbon surface area. To demonstrate this, the Celgard separator was coated with a dispersion of RFN10-1100C (which has a combination of high electrical conductivity and surface area) in lithiated Nafion solution to fabricate ultrathin interlayers, with thicknesses between 5~6 μm and carbon loading ~70 μg/cm$^2$—which is up to 100 times less carbon than other reported interlayers. See, e.g., Dresselhaus, M. S. NT10: Recent advances in carbon nanotube science and applications. ACS Nano 4, 4344-4349 (2010), which is incorporated by reference herein. In order to focus on the role of the interlayer, a standard sulfur electrode was prepared by mixing sulfur with Ketjen black (4:1 weight ratio). As expected, interface charge transfer resistance as measured by EIS decreased with the addition of the interlayer, commensurate with an effective reduction in the electron transport distance through the electrode (FIG. 5B). Both initial capacity (sulfur utilization) and capacity retention were improved with the addition of the interlayer (FIG. 5C). The control had an initial discharge capacity of 821 mAh/g at a discharge rate of 1 C. The discharge capacity increased to 1035 mAh/g, corresponding to an improvements of 26%, with the interlayer. Retained capacity after 300 cycles increased by 70% with the addition of the interlayer, from 242 mAh/g to 518 mAh/g. The voltage profiles remained stable through at least the first 300 cycles with the interlayer. An initial increase in the potential of the second discharge plateau was observed over the first 10 cycles with a corresponding decrease in cell polarization and increase in discharge capacity (FIGS. 5D and 5E). This effect has been well-documented and was attributed to electrode restructuring. The enhanced improvement in sulfur utilization was even more pronounced when thicker cathodes were used. For a cathode with 2 mg/cm$^2$ sulfur loading, the discharge capacity after 100 cycles increased by 43%, while a 78% increase was recorded for a 4 mg/cm$^2$ cathode.

SUPPLEMENTARY TABLE 1

Concentrations and detailed information about chemical reagents used for resorcinol-formaldehyde nanofiber synthesis.

| Chemical | Supplier | Purity | Stock concentration | Solvent |
|---|---|---|---|---|
| Ethylenediamine | Sigma-Aldrich | 99% | 10 v/v % | Ethanol |
| 3-Amino-propyltrimethoxysilane | Sigma-Aldrich | 97% | 10 v/v % | Ethanol |
| Resorcinol | Sigma-Aldrich | 99% | 1.67M | Ethanol |
| Formaldehyde | Alfa Aesar | 37% | 10 v/v % | Water |

SUPPLEMENTARY TABLE 2

Precursor volumes for a 150 mL reaction synthesis of resorcinol-formaldehyde (RFN) or organosilicon (RFN10, RFN30 and RFN50) nanofibers. All volumes are given in mL.

| | APTMS | Ethylenediamine | Resorcinol | Formaldehyde |
|---|---|---|---|---|
| RFN | — | 0.045 | 1.5 | 1.5 |
| RFN10 | 0.162 | — | 1.5 | 1.5 |
| RFN30 | 3.3 | — | 0.15 | 0.15 |
| RFN50 | 5 | — | 0.015 | 0.165 |

SUPPLEMENTARY TABLE 3

Summary of bacteriophage clones screened against resorcinol-formaldehyde resin (RFN10).

| | Peptide sequence | Net charge (pH = 8.5) | Average hydrophobicity (pH 7) |
|---|---|---|---|
| 1 | N/A (M13KE) | N/A | N/A |
| 2 | VSGSSPDS | −1 | 3.9 |
| 3 | DSPHTELP | −1 | 12.0 |
| 4 | ENKVE | −2 | 2.8 |
| 5 | EEAE | −3 | 0.9 |
| 6 | DCPDCYFP | −3.23 | 19.7 |

SUPPLEMENTARY TABLE 4

Summary of precursor and carbonization temperature on the physical properties of biotemplated carbon nanofibers.

| Precursor | Carbonization temperature (° C.) | BET surface area (m$^2$/g) | t-Plot micropore area (m$^2$/g) | Sheet resistivity (Ωm) | $I_D/I_G$ ratio | $L_a$ (nm) | $d_{002}$ (nm) |
|---|---|---|---|---|---|---|---|
| RFN | 1100 | 365 | 251 | 2.28 × 10$^{-3}$ | 1.68 | 2.6 | 0.38 |
| | 800 | 552 | 395 | | | | |
| RFN10 | 1100 | 776 | 643 | 2.80 × 10$^{-3}$ | 1.74 | 1.8 | 0.37 |
| | 1400 | 360 | 179 | | | | |
| | 800 | 1259 | 897 | | | | |
| RFN30 | 1100 | 1934 | 1549 | 5.24 × 10$^{-1}$ | 1.38 | 1.6 | 0.42 |
| | 1400 | 782 | 223 | | | | |

SUPPLEMENTARY TABLE 5

XPS-derived elemental compositions of carbon nanofibers with different precursors and different carbonization temperature.

| Precursor | Carbonization temperature (° C.) | At. % C | At. % O | At. % N | At. % Si |
|---|---|---|---|---|---|
| RFN | 1100 | 97.3 | 2.3 | 0.4 | 0 |
|  | 800 | 95.0 | 5.0 | 0 | 0 |
| RFN10 | 1100 | 95.1 | 4.5 | 0 | 0.4 |
|  | 1400 | 95.2 | 3.5 | 0 | 1.3 |
|  | 800 | 92.8 | 6.4 | 0.8 | 0 |
| RFN30-800C | 1100 | 88.0 | 9.5 | 1.9 | 0.6 |
|  | 1400 | 80.2 | 6.0 | 1.7 | 12.1 |

SUPPLEMENTARY TABLE 6

Dose-extraction of HD using BioCNF compared to BPL and a range of metal oxides.

| Substrate | % Removed after 24 hours |
|---|---|
| $Al_2O_3$ | 17.8 |
| $Mg(OH)_2$ | 1.4 |
| $TiO_2$ | 32.4 |
| $Fe_2O_3$ | 8.4 |
| $CeO_2$ | 17.6 |
| ZnO | 0 |
| BPL | 0 |
| BioCNF | 52 |

SUPPLEMENTARY TABLE 7

Fitting parameters for methylene blue uptake using various types of carbons. A pseudo-second order kinetic model was used for fitting. Initial methylene blue concentration was 1 mg/mL, carbon loading was 1 mg/mL for all samples.

| Carbon | $k_2$ (s$^{-1}$) | $q_e$ (mg/mg) |
|---|---|---|
| Biotemplated CNF (RFN30-1100C) | 0.456 | 0.877 |
| Charcoal (Pharmaceutical grade) | 0.105 | 0.336 |
| Activated carbon (Darco-G) | 0.068 | 0.757 |
| Carbon black (Ketjenblack ECP300JD) | 0.230 | 0.602 |

SUPPLEMENTARY TABLE 8

Fitting parameters for methylene blue uptake using various types of carbons. A pseudo-second order kinetic model was used for fitting. Initial methylene blue concentration was 1 mg/mL, carbon loading was 1 mg/mL for all samples.

| Carbon | k2 (s−1) | qe (mg/mg) |
|---|---|---|
| Biotemplated CNF (RFN30-1100C) | 0.456 | 0.877 |
| Charcoal (Pharmaceutical grade) | 0.105 | 0.336 |
| Activated carbon (Darco-G) | 0.068 | 0.757 |
| Carbon black (Ketjenblack ECP300JD) | 0.230 | 0.602 |

EXAMPLES

Synthesis of Resorcinol-Formaldehyde and Organosilicon Nanofibers

In a typical reaction, 150 mL of virus dispersion with concentration of $3.2 \times 10^{11}$ pfu/mL was preheated to 80° C. Ethanol solutions of either ethylenediamine (99%, Sigma-Aldrich) or 3-aminopropyltrimethoxysilane (97%, Sigma-Aldrich), followed by aqueous solutions of resorcinol (99%, Sigma-Aldrich) and formaldehyde (Alfa-Aesar) were added in the required ratio according to (see Table 3). All solutions were freshly prepared. The reaction mixture was thoroughly mixed, then incubated at 80° C. for at least 12 hours with no mechanical agitation. On completion, the nanofibers were collected by filtration then washed with water and ethanol. To synthesize colloidal nanofibers, the pH of the solution was adjusted to 8.3 using potassium hydroxide and the reaction was carried out under gentle stirring.

TABLE 3

Precursor volumes for a 150 mL reaction synthesis of resorcinol-formaldehyde (RFN) or organosilicon (RFN10, RFN30 and RFN50) nanofibers. All volumes are given in mL.

| | 10% APTMS | 10% Ethylenediamine | 1.67M Resorcinol | 10% Formaldehyde |
|---|---|---|---|---|
| RFN | — | 0.045 | 1.5 | 1.5 |
| RFN10 | 0.162 | — | 1.5 | 1.5 |
| RFN30 | 3.3 | — | 0.15 | 0.15 |
| RFN50 | 5 | — | 0.015 | 0.165 |

Synthesis of Carbon Nanofibers

The precursor nanofibers (RFN, RFN10 or RFN30) were heated to temperatures of 800° C., 1100° C. or 1400° C. in flowing Argon for at least 2 hours using a 2° C./min ramp rate. Nanofibers containing silicon moieties were washed with 2 M potassium hydroxide at 80° C. for at least 12 hours, then thoroughly washed again with water.

Imaging

Imaging was done using the FEI Tecnai G2 and the JEOL 2010 High Resolution TEM. To clarify carbon texture, high resolution micrographs were processing using FFT and the image brightness/contrast were adjusted. No further imaging processing was done, a best attempt was made to ensure the processing were consistent for all images. Image entropies were calculated using:

$$J = -\sum_i p_i \log_2 p_i$$

Chemical Characterization

FTIR spectra were collected using the Bruker Lumos FTIR in ATR mode. A background correction was used and $CO_2/H_2O$ peaks were removed. XPS spectra were collected using the Thermo Scientific K-Alpha. Ion flood gun was used for all samples. No post-measurement peak corrections were done. Peaks were fitted using Voigt profiles (Gaussian: Lorentzian ratio 7:3). Raman spectra were obtained using the Horiba LabRam HR800, using a 532 nm light source.

Microstructure Characterization

XRD diffractograms were collected using the Panalytical X'Pert Pro Multipurpose Diffractometer. Data was collected in the Bragg-Brentano geometry between 10° and 60° 2θ using a copper anode. All diffractograms were fitted using Voigt peaks with a constant linear background.

Physical Characterizations

BET measurements were obtained using the Micromeritics ASAP 2020. Pore size distribution was determined using DFT and micropore contributions were estimated using the t-plot method. TGA and DSC were measured using TA Instruments Discovery systems. TGA thermograms were obtained under nitrogen using a linear ramp mode (10° C./min) from 40° C. to 800° C. DSC was obtained using a linear ramp cycle from 40° C. to 300° C. and back.

Sheet Resistivity

Carbon nanofiber films were made by mixing with Teflon 8A in 9:1 weight ratio using mortar and pestle, then rolled into films of thickness ≤100 µm. The sheet resistance was measured using a 4-point probe (Keithley SCS-4200) with probe spacing of 1.27 mm, and resistivity calculated by:

$$\rho = 4.5324 t\left(\frac{v}{i}\right)$$

Small Molecule Adsorption

Molecules tested were dissolved in water to a concentration of either 0.25 mg/mL or 1 mg/mL. For pharmaceutical molecules, additional tests were conducted in simulated gastric fluid (0.2 w/v % sodium chloride in 0.7 v/v % hydrochloric acid, with a pH of 1). 1~10 mg of either RFN30-1100C or commercial activated charcoal (USP grade, Sigma-Aldrich) was used per test. To minimize the effect of entrapped air in rate tests, the carbon was wetted first and slightly concentrated solutions of the substrate were added to the required final concentration. Molecular concentrations in solution were determined by optical absorption, where a small aliquot of solution was removed and passed through a 0.2 µm filter to remove residual carbon measured using UV-Vis spectrophotometry (NanoDrop ND-1000). Ionic concentrations were determined using ICP-AES (Agilent 5100). Adsorption kinetics were fitted using pseudo-second order kinetics:

$$\frac{t}{q_t} = \frac{1}{k_2 q_e^2} + \left(\frac{t}{q_e}\right)$$

Lithium-Sulfur Battery Interlayer

Carbon nanofibers (RFN10-1100C) were dispersed in ethanol to a concentration of 100 mg/mL by either probe sonication for 2 hours or cup-horn sonication for 4 hours until a homogeneous ink was formed. Lithion (lithiated Nafion, Ion Power) was added to a final Lithion:carbon weight ratio of either 6:4 or 8:2. The mixture was used to coat a Celgard 2400 separator by doctor-blading. The sulfur-carbon (S/C) composite was prepared by infusing sulfur into Ketjen Black (EC-600JD, AkzoNobel) in 4:1 sulfur-to-carbon weight ratio at 155° C. for 12 hours in a sealed vial. 2032 coin-type cells were assembled using lithium metal (0.76 mm thick, Alfa Aesar) as the anode electrode, Celgard 2400 membranes as the separator, and a cathode composed of a mixture of the as-prepared C/S composite, 10% Super-P Li carbon black (TIMCAL,) and 10% poly(vinylidene difluoride) (Sigma-Aldrich), and an electrolyte of 40 µL of 1 M lithium bis(trifluoromethanesulfone)imide (LiTFSI) and 0.2 M LiNO$_3$ in 1,3-dioxolane/1,2-dimethoxyethane (v/v=1:1). Cell assembly was carried out in an argon-filled glovebox (MBraun Labmaster). The room-temperature cycling characteristics of the cells were evaluated under galvanostatic conditions using Land battery testers, and electrochemical processes in the cells were studied by cyclic voltammetry and impedance using the Biologic VMP-3 Potentiostat. FIG. 12 shows in the improvement in high loading lithium-sulfur battery cycling performance when a carbon nanofiber interlayer was added.

Demonstration of Efficacy

Figure 21:
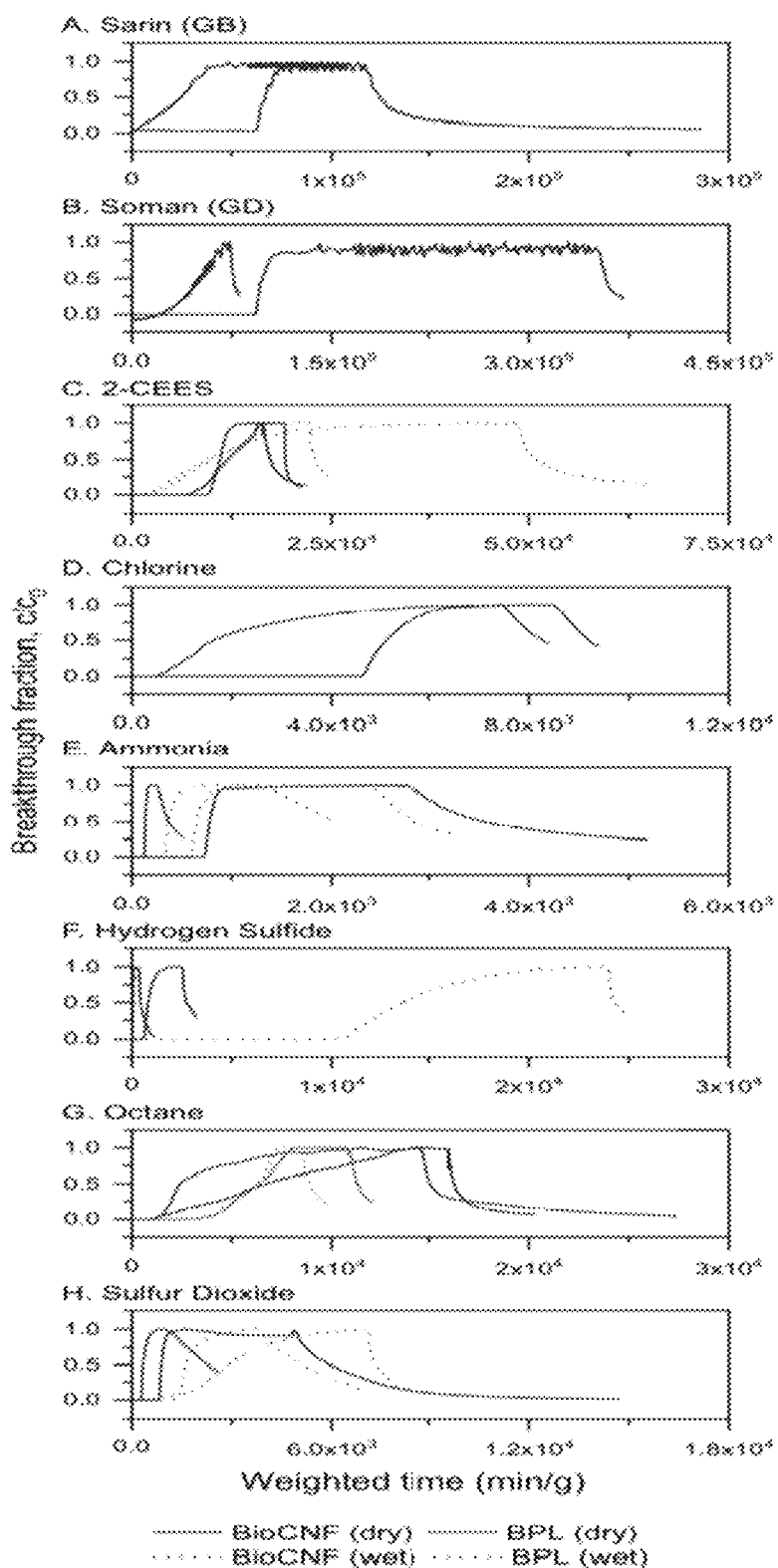
FIG. 21 shows the micro-breakthrough curves for the filtration of various toxic industrial chemicals and chemical warfare agents using biotemplated carbon nanofibers compared to BPL carbon.

The initial hypothesis was that the open network structure of biotemplated carbon nanofibers (BioCNF) and its small diameter would allow for optimal access to adsorptive sites and enhance removal of CWAs. To test this, micro-breakthrough experiments were carried out to compare breakthrough capacities against BPL activated carbon. BPL carbon is a particulate carbon sorbent that is commonly used as a benchmark for gas phase adsorption. The G-series nerve agents Sarin (GB) and Soman (GD) were tested because they are the primary filtration hazards due to their relatively high vapor pressure compared to other CWAs. Testing was done by charging the CWA into a flowing gas, at an inlet concentration of 750 mg/m$^3$ for GB and 375 mg/m$^3$ for GD. The gas was then filtered through either ~5 mg of BioCNF or ~20 mg of BPL, and the elute concentration was measured. A lower mass of BioCNF was used due to its higher specific volume. The GB and GD breakthrough curves are shown in FIG. 21A and FIG. 21B, respectively. Particle size and morphology had a significant effect on the shape of the breakthrough curve. For the granular BPL carbon, both GB and GD began breaking through immediately. On the contrary, BioCNF was able to completely suppress breakthrough until near saturation, at which point a steep response was observed. This suggested excellent mass transfer and access to active surface sites, and therefore highly efficient utilization of the available surfaces in support of our initial hypothesis.

Referring to FIG. 21A-H, each chemical was mixed with either dry or humid air at the desired challenge concentration and passed through the sorbent. After complete saturation of the sorbent, the initial elution of adsorbed chemicals was measured.

Figure 45:
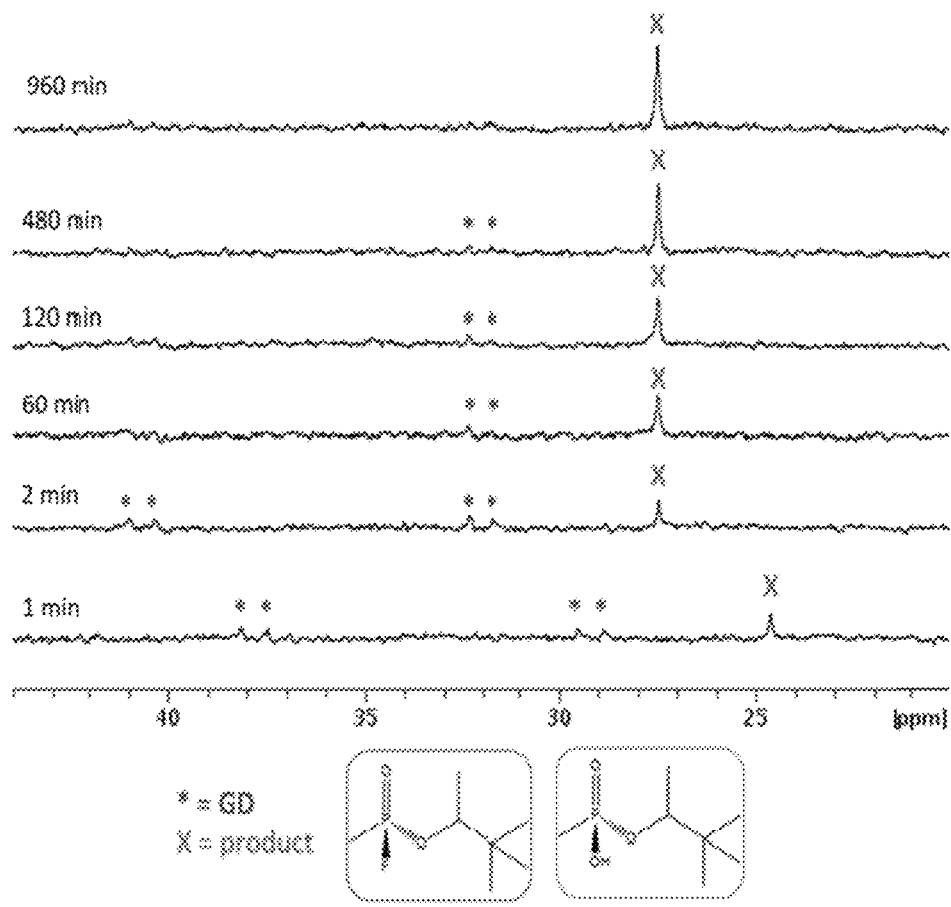
FIG. 45 shows an NMR spectrum taken at various time intervals, tracking the hydrolysis of GD on BioCNF. The main hydrolysis product was pinacolyl methylphosphonic acid (PMPA).

Total uptakes of the chemicals were calculated by integrating the breakthrough curves plotted against weighted time to account for differences in sorbent loading and tabulated in Table 0-3. To our surprise, the GB capacity of BioCNF was exceptionally high at 9.4 mol/kg, which was 3× higher than the capacity measured for BPL, which was 3.1 mol/kg. Likewise, the GD capacity of the BioCNF was over 2× higher than BPL, with a capacity of 5.9 mol/kg compared to a capacity of 2.8 mol/kg for BPL. It was hypothesized that removal of CWAs using BioCNF was facilitated by an additional reactive mechanism that was not present in BPL. To test this, a dose-extraction experiment was conducted. BioCNF and BPL were each dosed with GD and equilibrated for 24 hours. After dosage, the agent was extracted using excess acetonitrile, separated, and its concentration was measured. All of the GD dosed to BPL was extracted and recovered, indicating no reaction had occurred. Over the same period, 42% of the dosed GD was not recovered from BioCNF, indicating GD had likely undergone some reactive decomposition. However, it was not possible to extract the reaction byproducts using acetonitrile, indicating there may have been strong binding of these byproducts to BioCNF. To identify these byproducts, GD was spiked into a dispersion of BioCNF in water, and the reaction was continuously monitored using nuclear magnetic resonance (NMR) imaging. The major reaction product was identified as pinacolyl methylphosphonic acid (PMPA) (FIG. 45). This indicated that the decomposition of GD occurred by a hydrolysis mechanism, proceeding through a phosphorous $S_N2$ nucleophilic attack. During this reaction, the P—F bond was broken and replaced by a P—OH bond to yield a non-toxic product. See, e.g., Kim, K., Tsay, O. G., Atwood, D. A. & Churchill, D. G. Destruction and detection of chemical warfare agents. *Chem. Rev.* 111, 5345-5403 (2011), which is incorporated by reference herein. While this type of hydrolysis typically occurs in aqueous basic solutions, an analogous reaction was observed to occur on the surfaces of a range of metal oxides (MgO, $Al_2O_3$ and $TiO_2$). See, e.g., Wagner, G. W., Koper, O. B., Lucas, E., Decker, S. & Klabunde, K. J. Reactions of VX, GD, and HD with Nanosize CaO: Autocatalytic Dehydrohalogenation of HD. *J. Phys. Chem. B* 104, 5118-5123 (2000), which is incorporated by reference herein. It was thought that basic oxygen groups on these oxides acted to promote hydrolysis. Because a large amount of similar oxygen species were also present in BioCNF, the degradation of GD could likely be explained by a similar mechanism. See, e.g., Barton, S. S., Evans, M. J. B., Halliop, E. & MacDonald, J. A. F. Acidic and basic sites on the surface of porous carbon. *Carbon N. Y.* 35, 1361-1366 (1997). In addition, studies have pointed to the catalytic properties of intrinsic carbon defects, such as vacancies, holes and edges that break up the integrity of π-electron conjugation, and provide dangling bonds that promote radical chain oxidation. See, e.g., Navalon, S., Dhakshinamoorthy, A., Alvaro, M., Antonietti, M. & Garcia, H. Active sites on graphene-based materials as metal-free catalysts. *Chem. Soc. Rev.* 46, 4501-4529 (2017), which is incorporated by reference herein. It was likely that these reactive centers helped to catalyze the hydrolysis reaction. For this type of surface mediated reaction, the hydrolysis product is usually strongly bound to the surface as phosphonates of PMPA, which are difficult to dissolve under non-acidic conditions, and explains why extraction using acetonitrile was ineffective.

TABLE 0-3

Comparison of the micro-breakthrough capacities of BioCNF compared against the non-templated control and commercial BPL carbon for various toxic industrial chemicals and chemical warfare agents. Dry experiments were conducted at ~0% humidity. Wet experiments were conducted at ~80% humidity.

| Chemical | Type | Concentration (mg/m³) | Loading (mol/kg) BioCNF Dry | BioCNF Wet | Control Dry | Control Wet | BPL Dry | BPL Wet |
|---|---|---|---|---|---|---|---|---|
| Sarin (GB) | CWA | 750 | 9.4 | — | — | — | 3.1 | — |
| Soman (GD) | CWA | 375 | 5.9 | — | — | — | 2.8 | — |
| 2-CEES | CWA | 4000 | 7.7 | 7.3 | 0.02 | 0.05 | 7.1 | 6.1 |
| Ammonia | TIC | 2000 | 1.9 | 1.6 | — | — | 0.31 | 0.88 |
| Hydrogen sulfide | TIC | 1000 | 0.54 | 8.5 | 0.11 | 0.82 | 0.03 | 0.08 |
| Sulfur dioxide | TIC | 1000 | 0.39 | 0.56 | 0.10 | 0.25 | 0.11 | 0.96 |
| Chlorine | TIC | 1000 | 2.9 | — | — | — | 1.2 | — |
| Octane | TIC | 4000 | 5.0 | 2.4 | — | — | 4.2 | 4.3 |
| Cyanogen chloride | TIC | 4000 | 1.99 | 0.19 | 0.05 | 0.04 | 0.96 | 0.32 |
| Methyl bromide | TIC | 2000 | 0.58 | 0.09 | — | — | 0.70 | 0.30 |

Figure 22:
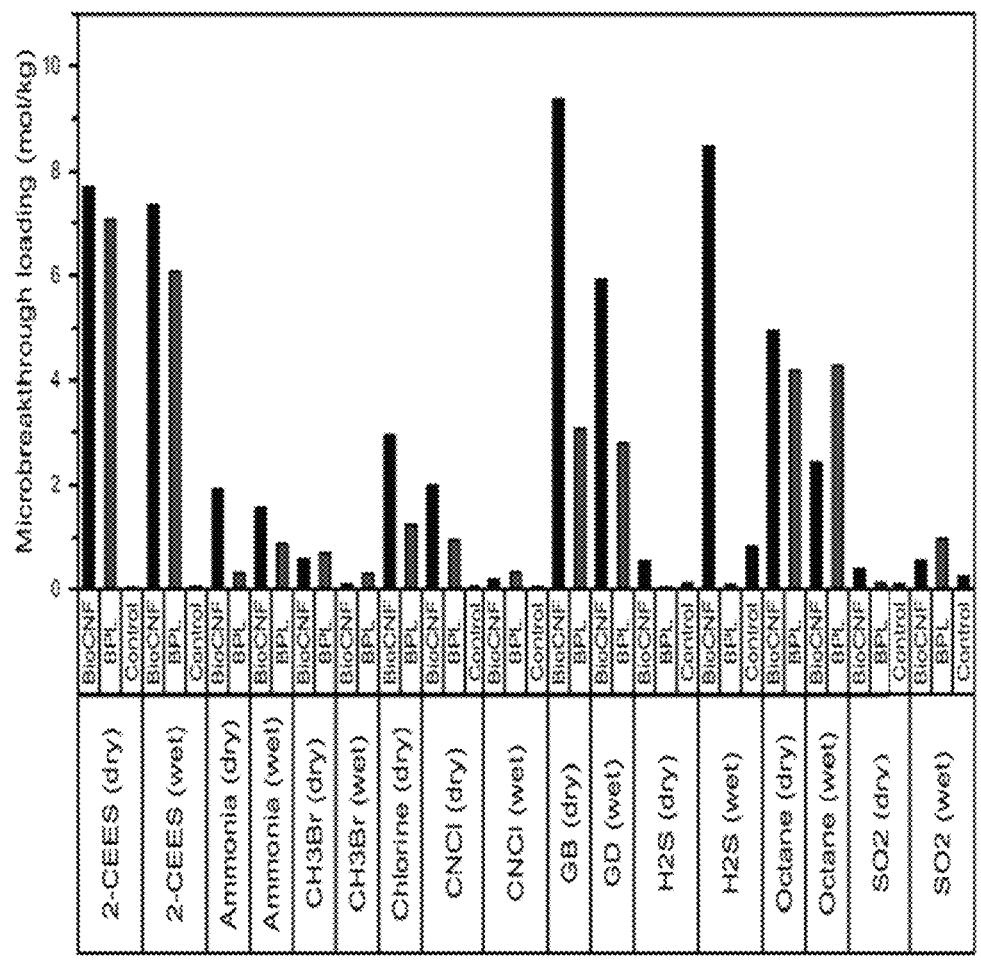
FIG. 22 shows a comparison of the micro-breakthrough capacities of BioCNF plotted against the non-templated control and commercial BPL carbon for various toxic industrial chemicals and chemical warfare agents.

Referring to FIG. 22, comparison of the micro-breakthrough capacities of BioCNF plotted against the non-templated control and commercial BPL carbon for various toxic industrial chemicals and chemical warfare agents was shown. Dry experiments were conducted at ~0% humidity. Wet experiments were conducted at ~80% humidity.

Figure 46:
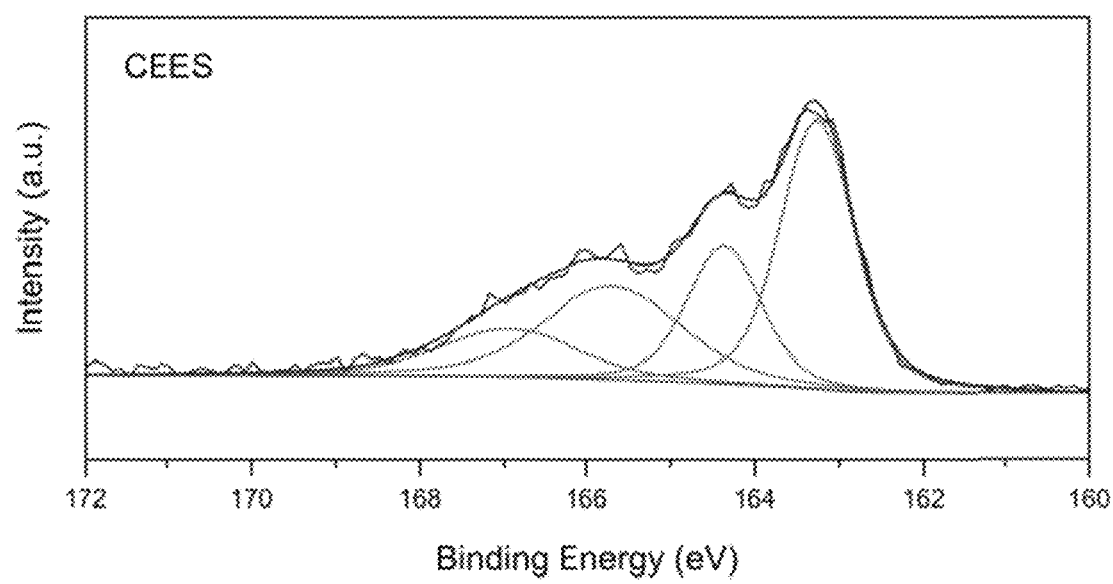
FIG. 46 shows a high definition XPS spectrum of the S2p peak taken for BioCNF after 2-CEES micro-breakthrough testing. The sulfide doublet is visible along with doublet peaks corresponding to an oxidized sulfur species, likely to be sulfone.
Figure 47:
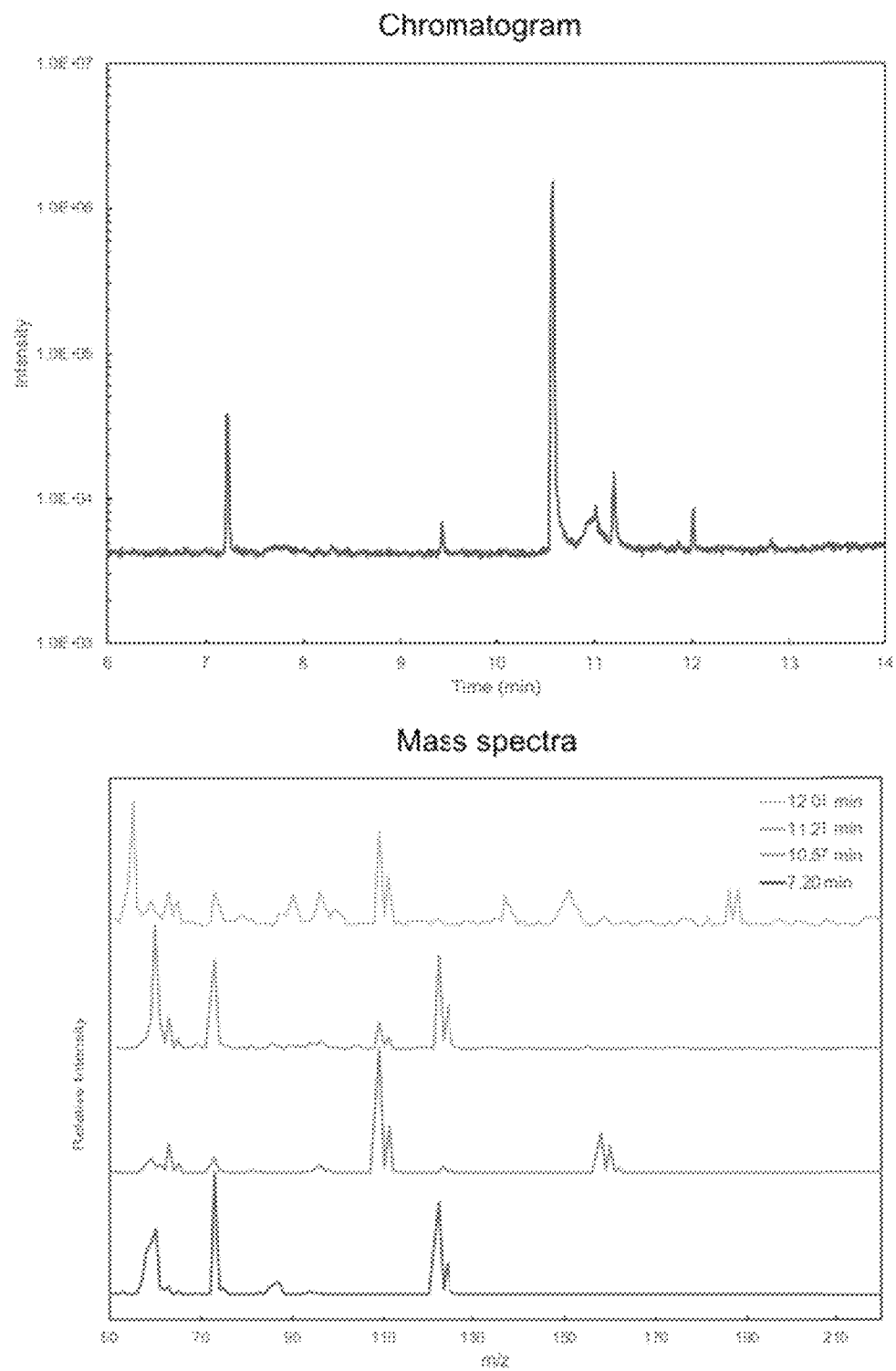
FIG. 47 shows GC-MS of HD byproducts from BioCNF. The chromatogram and corresponding mass spectra at times 7.20 min, 10.57 min, 11.21 min and 12.01 min are shown. The spectra at 7.20 min and 11.21 min correspond to 2-chloroethyl vinyl sulfide, while the spectra at 10.57 min and 12.01 min correspond to unreacted HD.

Applicants also tested the uptake of the blistering agent mustard gas (HD) using BioCNF. Initial micro-breakthrough experiments were conducted for the HD simulant, 2-chloroethyl ethyl sulfide (2-CEES), under both dry (~0%) and humid (80%) conditions, and compared against BPL (Error! Reference source not found. C). The breakthrough capacities are tabulated in Table 0-3. BioCNF had ~10% and ~20% higher capacity than BPL under dry and humid conditions, respectively. XPS of the BioCNF surface following adsorption revealed the presence of an oxidized sulfur species, likely corresponding to either sulfone or sulfoxide groups, pointing towards oxidation of the sulfide group (FIG. 46). See, e.g., Livingston, S. R. & Landry, C. C. Oxidation of a Mustard Gas Analogue Using an Aldehyde/O2 System Catalyzed by V-Doped Mesoporous Silica. *J. Am. Chem. Soc.* 130, 13214-13215 (2008), which is incorporated by reference herein. The ability to oxidize 2-CEES directly using carbon was particularly interesting. Previous work had shown that HD was susceptible to oxidation only when treated with a powerful oxidant such as hydrogen peroxide due to the nucleophilic action of the $OOH^-$ ion, or under high temperature hydrothermal conditions. See, e.g., Osovsky, R. et al. Decontamination of adsorbed chemical warfare agents on activated carbon using hydrogen peroxide solutions. *Environ. Sci. Technol.* 48, 10912-10918 (2014), which is incorporated by reference herein. A dose-extraction experiment using pure HD was conducted. All HD was extracted from BPL, indicating no chemical reaction had occurred. However, 52% of the HD was not recovered from BioCNF, indicating substantial reaction occurred over the same time. Using gas chromatography coupled with mass spectroscopy (GC-MS) and flame ionization detector (GC-FID), small amounts of thiodiglycol and 2-chloroethyl vinyl sulfide as reaction byproducts were identified (FIG. 47). The presence of thiodiglycol indicated hydrolysis of HD, while 2-chloroethyl vinyl sulfide indicated an elimination mechanism. See, e.g., Wagner, G. W., Koper, O. B., Lucas, E., Decker, S. & Klabunde, K. J. Reactions of VX, GD, and HD with Nanosize CaO: Autocatalytic Dehydrohalogenation of HD. *J. Phys. Chem. B* 104, 5118-5123 (2000), which is incorporated by reference herein. These byproducts, albeit in small amounts, pointed to the potential for multiple decomposition pathways. For further comparison, dose-extraction experiments were conducted against a range of metal oxides. Even though metal oxides are generally considered the best candidates for CWA detoxification, BioCNF outperformed all metal oxides tested. Even the most effective metal oxide, titanium dioxide, only removed 32% of the applied HD compared to 52% using BioCNF. Other metal oxides decomposed between 1~18% of the applied HD, while BPL carbon showed no reactivity at all (Supplementary Table 6).

Figure 48:
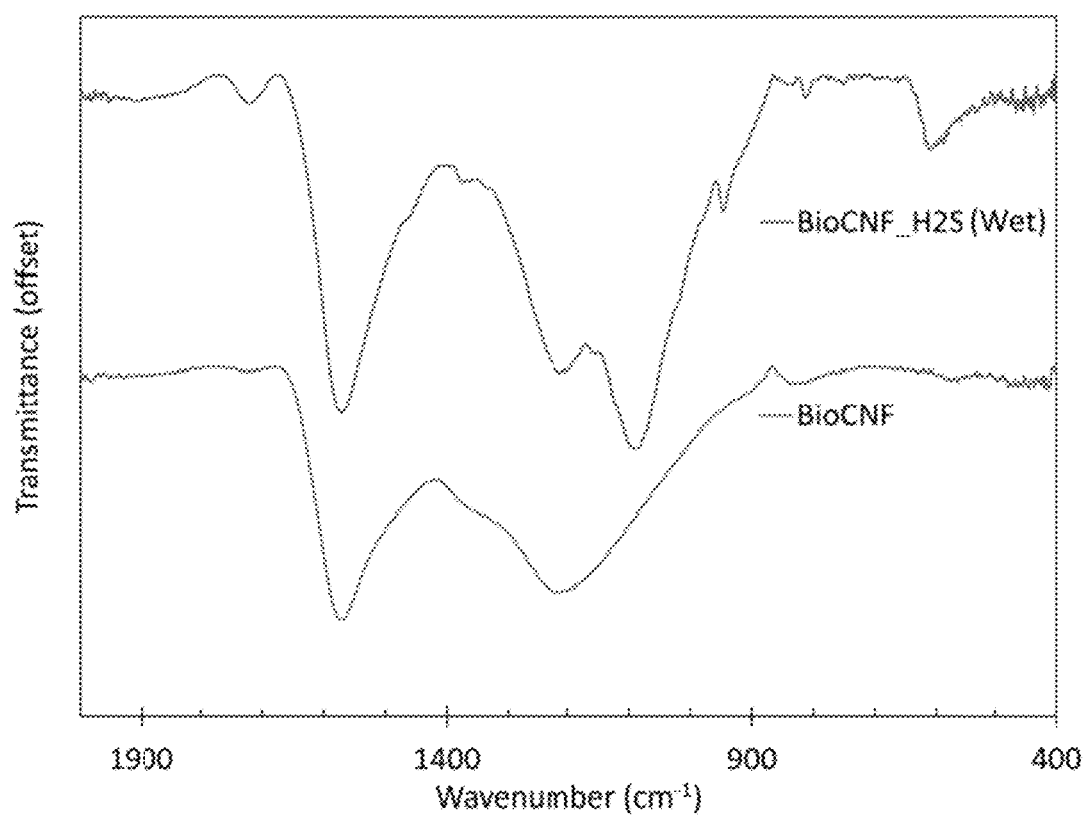
FIG. 48 shows ATR-FTIR spectra of BioCNF before and after micro-breakthrough testing against $H_2S$. The spectrum after breakthrough had features consistent with oxidized $H_2S$ species, such as a red-shifted stretch of a $S_4$ allotrope (608 cm$^{-1}$) and a sulfoxide stretch at 1090 cm$^{-1}$.
Figure 49:
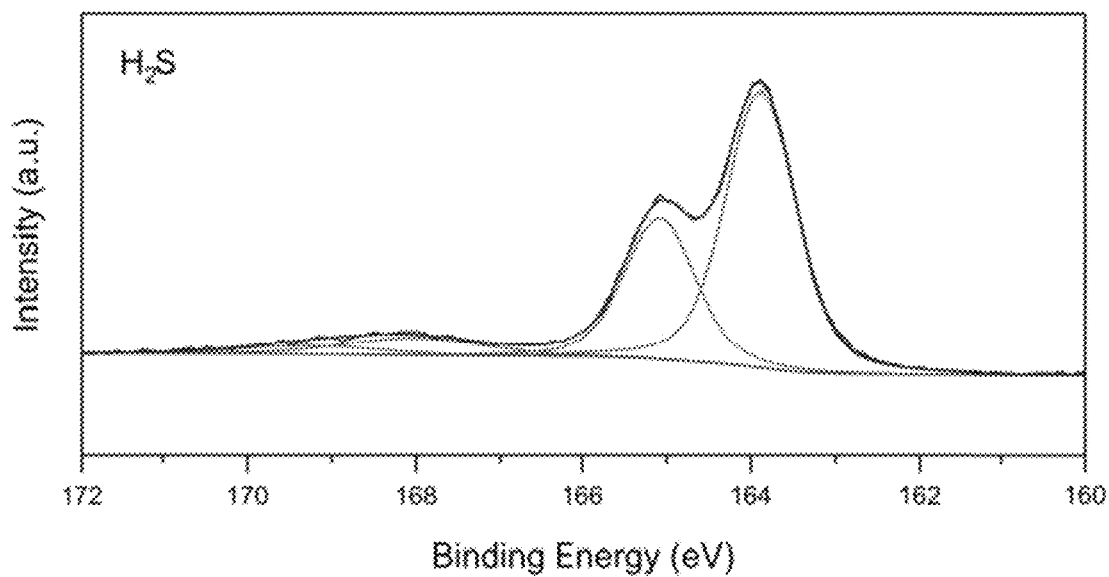
FIG. 49 shows a high definition XPS spectrum of the S2p peak taken for BioCNF after $H_2S$ micro-breakthrough testing.

The capacity of BioCNF was screened against a range of TICs, including ammonia, hydrogen sulfide, sulfur dioxide, chlorine and octane. Removal of TICs was measured using a micro-breakthrough experiment similar to that done for CWAs (Error! Reference source not found. C—H). The capacities are tabulated in Table 0-3. Under dry conditions, BioCNF outperformed BPL for all TICs tested. Of particular note was the uptake of hydrogen sulfide ($H_2S$). Due to the high volatility of this gas, BPL showed almost no adsorption. On the other hand, BioCNF demonstrated exceptional capacities of 0.54 mol/kg and 8.5 mol/kg under dry and humid conditions, respectively. The mechanism behind this significant uptake was due to the oxidation of hydrogen sulfide to elemental sulfur and sulfoxides, similar to the oxidation of 2-CEES to its corresponding sulfoxide that was previously observed. See, e.g., Zhang, Z. et al. Millimeter-sized mesoporous carbon spheres for highly efficient catalytic oxidation of hydrogen sulfide at room temperature. *Carbon N. Y.* 96, 608-615 (2016), which is incorporated by reference herein. FTIR analysis showed several peaks consistent with oxidized $H_2S$ species, such as a red-shifted stretch of a $S_4$ allotrope (608 $cm^{-1}$) and a sulfoxide stretch (1090 $cm^{-1}$) (FIG. 48). See, e.g, Meyer, B. Elemental Sulfur. *Chem. Rev.* 76, 367-388 (1976), which is incorporated by reference herein. XPS confirmed the presence of mostly elemental sulfur or polysulfide species and a small amount of oxidized sulfur species (FIG. 49). The relatively fast drop in effluent concentration after feed termination was consistent with the conversion of $H_2S$ to a less volatile product. In the absence of such a mechanism, one could expect significant outgassing after feed termination due to the high volatility of $H_2S$. Ammonia loading on BioCNF was also significantly higher than on BPL, measuring at 6× the capacity of BPL under dry conditions and 2× when humid. In this case, the oxygen species on the carbon most likely promoted hydrogen bonding rather than a reactive mechanism due to the continuous off-gassing of ammonia after feed termination. Chlorine loading for BioCNF was roughly 2~3× higher than BPL. For sulfur dioxide and octane, uptake using BioCNF was higher than BPL under dry conditions (3~4× higher in the case of sulfur dioxide), but lower under humid conditions. This likely suggested that these chemicals competed with water for binding sites, and that the more polar surface of BioCNF had a higher preference for water than the more hydrophobic surfaces of BPL.

Figure 50:
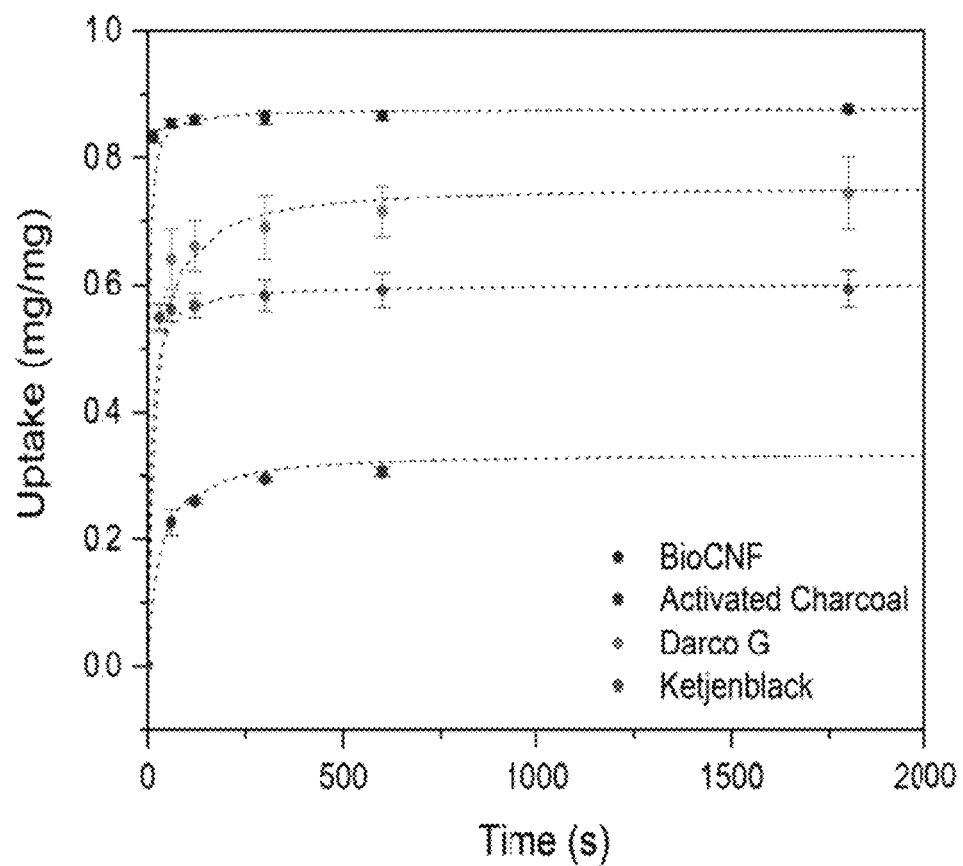
FIG. 50 shows the adsorption rate of methylene blue from solution using biotemplated carbon nanofibers compared to various commercial benchmarks. An initial methylene blue concentration of 1 mg/mL was used with a carbon loading of 1 mg/mL.
Figure 51:
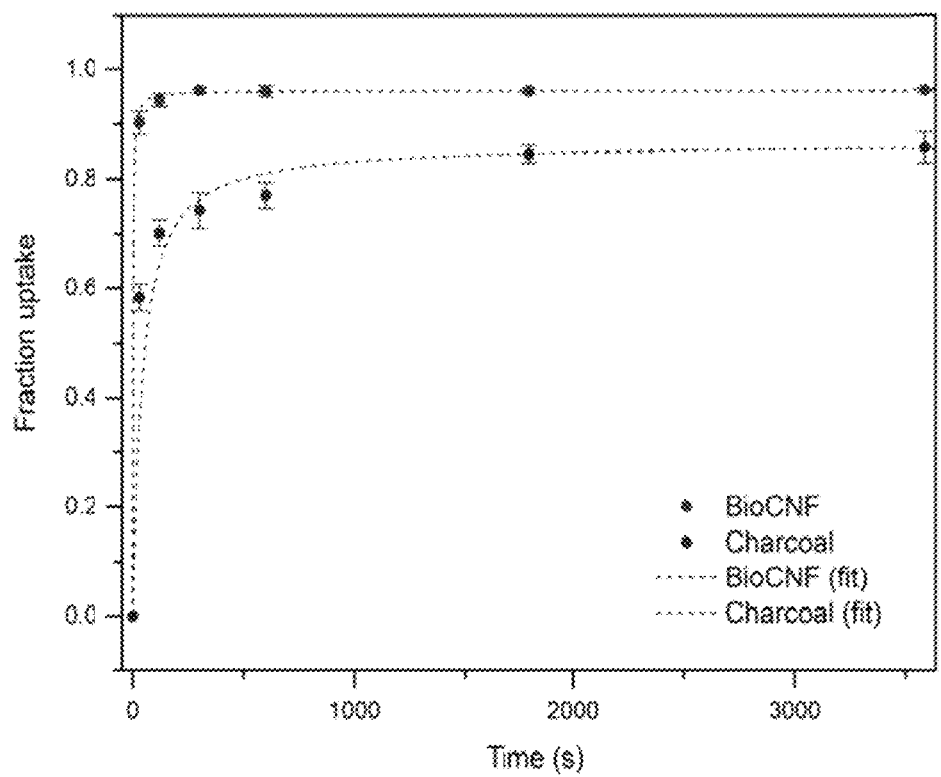
FIG. 51 shows adsorption of propranolol (0.25 mg/mL) using BioCNF and activated charcoal at 1 mg/mL loading. All data points were fitted to a pseudo-second order rate equation.

BioCNF was also tested as a sorbent material for a wide range of micropollutants, such as industrial dyes, pharmaceutics and heavy ions (Table 0-4). With the exception of m-cresol and the orange G dye, uptake for all molecules and ions tested exceeded 400 mg/g for an initial solution concentration of 1 mg/mL. Even for lead and strontium ions, which are difficult to remove using activated carbon without added complexing agents, it was possible to achieve exceptionally high capacities of 780 mg/g and 733 mg/g, respectively. See, e.g., Babel, S. & Kurniawan, T. A. Low-cost adsorbents for heavy metals uptake from contaminated water: A review. *J. Hazard. Mater.* 97, 219-243 (2003), which is incorporated by reference herein. For methylene blue, a maximum uptake of 902 mg/g was achieved, which exceeded most commercial carbons by 1~2 fold and is amongst the highest values recorded for comparable carbon-based sorbents. See, e.g., Rafatullah, M., Sulaiman, O., Hashim, R. & Ahmad, A. Adsorption of methylene blue on low-cost adsorbents: A review. *J. Hazard. Mater.* 177, 70-80 (2010), which is incorporated by reference herein. For many activated carbon and metal organic framework sorbents, poor diffusion through nanopores limits access to surface sites. See, e.g., Largitte, L. & Pasquier, R. A review of the kinetics adsorption models and their application to the adsorption of lead by an activated carbon. *Chem. Eng. Res. Des.* 109, 495-504 (2016), which is incorporated by reference herein. The effectiveness of BioCNF was likely due, in part, to its open network structure and small nanofiber diameter, which facilitated access to surface sites. If this was true, one could also expect much faster adsorption rates. To test this, adsorption rate was compared against various commercial activated carbons using methylene blue as the test molecule (FIG. 50). For an initial methylene blue concentration of 1 mg/mL and carbon loading of 1 mg/mL, achieved 79% removal (88% of the equilibrium uptake) within ~15 s and 84% (93% of equilibrium uptake) within 1 minute using BioCNF was achieved. The pseudo-second order rate constant for BioCNF was 0.46 $s^{-1}$, this was 2× higher than the next best carbon sorbent that was tested, Ketjenblack, which had a rate constant of 0.23 $s^{-1}$ (See Supplementary Table 8). See, e.g., Hameed, B. H., Din, A. T. M. & Ahmad, A. L. Adsorption of methylene blue onto bamboo-based activated carbon: Kinetics and equilibrium studies. *J. Hazard. Mater.* 141, 819-825 (2007), which is incorporated by reference herein. At an initial concentration of 0.25 mg/mL, methylene blue completely discolored immediately upon shaking. This combination of high capacity and rapid adsorption rate makes BioCNF a highly promising sorbent material for a large number of different applications. One example is gastric decontamination. Currently, the effectiveness of activated charcoal used for this application is severely limited if not administered immediately likely due in part to poor adsorption rate. See, e.g., Chyka, P. A., Seger, D., Krenzelok, E. P. & Vale, J. A. Position Paper: Single-Dose Activated Charcoal. *Clin. Toxicol.* 43, 61-87 (2005), which is incorporated by reference herein. The uptake of propranolol (a prototypical β-blocker with high overdose rate) was tested using BioCNF against the commercially available pharmaceutical grade activated charcoal. See, e.g., Mowry, J. B., Spyker, D. A., Brooks, D. E., Zimmerman, A. & Schauben, J. L. 2015 Annual Report of the American Association of Poison Control Centers' National Poison Data System (NPDS): 33rd Annual Report. *Clin. Toxicol.* 54, 924-1109 (2016), which is incorporated by reference herein. Using 1 mg/mL of BioCNF and an initial propranolol concentration of 0.25 mg/mL, a 90% reduction in propranolol concentration was observed within 30 s. By comparison, only a 58% reduction was observed using activated charcoal during the same time (FIG. 51).

TABLE 0-4

Summary of adsorptive capacity of biotemplated carbon nanofibers for various small molecules and heavy ions in liquid phase.

| Chemical | Type | Maximum uptake[1] (mg/g) | Maximum uptake[2] (mg/g) |
| --- | --- | --- | --- |
| Phenol | Phenolic | 740 ± 38 | |
| m-Cresol | Phenolic | 327 ± 15 | |
| Aspirin | Pharmaceutic | 846 ± 20 | 760 ± 25 |
| Amitriptyline | Pharmaceutic | 465 ± 47 | 459 ± 11 |
| Nortriptyline | Pharmaceutic | 459 ± 54 | 493 ± 15 |
| Propranolol | Pharmaceutic | Not soluble | 847 ± 44 |
| Pyrocatechol violet | Dye | 738 ± 34 | |
| Orange G | Dye | 319 ± 38 | |
| Ethylorange | Dye | 496 ± 10 | |
| Acid yellow 14 | Dye | 779 ± 25 | |
| Methylene blue | Dye | 902 ± 36 | |
| Sulforhodamine B | Dye | 490 ± 8 | |
| Brilliant green | Dye | 980 ± 8 | |
| Brilliant blue | Dye | 878 ± 18 | |
| Lead | Heavy ion | 780 ± 60 | |
| Strontium | Heavy ion | 733 ± 55 | |

Micro-Breakthrough.

Micro-breakthrough testing was conducted on both biotemplated carbon nanofiber (BioCNF) and BPL activated carbon (12×30 mesh size) for comparison. Materials were loaded into a fritted glass test tube (4 mm I.D.) to a depth of approximately 4 mm. The BioCNF mass used for tests was approximately 5~10 mg, while BPL carbon was approximately 20 mg, the difference in mass loading was due to differences in density.

For the G-series nerve agents, Sarin (GB) and Soman (GD), a saturator cell was used to deliver the agent to a dry diluent stream at rates to achieve challenge concentrations of approximately 130 ppm (750 $mg/m^3$) and 50 ppm (375 mg/m³) for GB and GD, respectively. A Nicolet 380 Fourier transform infrared with a DTGS detector and Axiom Inc. gas cell with a 0.5 m pathlength were used to monitor the concentration of CWA in the effluent stream. For the vesicant simulant 2-chloroethyl ethyl sulfide (2-CEES), the chemical was placed in a saturator cell and an air stream was passed over the liquid and subsequently mixed to a challenge concentration of 4000 mg/m³. A flame ionization detector was used to detect 2-CEES. For the toxic industrial chemicals, ammonia, chlorine, hydrogen sulfide, sulfur dioxide and octane testing, neat gas was loaded into a steel ballast and then pressurized to 20 psig. The gases were subsequently mixed with a dry or humid air stream using mass flow controllers at rates necessary to achieve the desired challenge concentrations (ammonia: 2000 mg/m³; chlorine, hydrogen sulfide and sulfur dioxide: 1000 mg/m³). A photoionization detector was used to detect ammonia, chlorine and octane, eluting through the packed bed. A flame photometric detector was used for hydrogen sulfide and sulfur dioxide.

After micro-breakthrough testing, some samples were analyzed using FTIR and XPS to identify surface-bound products. For FTIR, the Bruker Tensor 27 FTIR with a Bruker Platinum ATR accessory equipped with a single reflection diamond crystal was used. For XPS, the Thermo Scientific K-Alpha+system was used.

Dose-Extraction.

BioCNF and BPL activated carbons were equilibrated for several hours at 50% relative humidity. Next, approximately 5 μL of GD or HD was dosed to the sorbents, which was then vortex-mixed. After 24 h, 6 mL of acetonitrile was added to the sorbent to extract the agent and the vial was centrifuged. The supernatant was extracted from the vial and analyzed using a GC-MS (Agilent 6890/5973).

Nuclear Magnetic Resonance.

2 μL of GD was dosed to 20 mg of BioCNF in 1 mL of $H_2O$, the reaction progress was tracked using the Bruker Ultrashield 300/54 MM system.

Liquid-Phase Adsorption.

All small molecules and ions tested were dissolved in water to a concentration of either 0.25 mg/mL or 1 mg/mL. For pharmaceutical molecules, additional tests were conducted in simulated gastric fluid (0.2 w/v % sodium chloride in 0.7 v/v % hydrochloric acid, with a pH of 1). 1~10 mg of either BioCNF or commercial activated carbon (activated charcoal, USP grade from Sigma-Aldrich; Darco-G60 from Sigma-Alrich; Ketjenblack ECP300JD from AkzoNobel) was used per test. To minimize the effect of entrapped air in rate tests, the carbon was wetted first and slightly concentrated solutions of the substrate were added to the required final concentration. Molecular concentrations in solution were determined by optical absorption, where a small aliquot of solution was removed and passed through a 0.2 μm filter to remove residual carbon measured using UV-Vis spectrophotometry (NanoDrop ND-1000). Ionic concentrations were determined using ICP-AES (Agilent 5100). Adsorption kinetics were fitted using pseudo-second order kinetics:

$$\frac{t}{q_t} = \frac{1}{k_2 q_e^2} + \left(\frac{t}{q_e}\right)$$

Where t is time in s, $q_t$ is the amount of chemical taken up at time t in mg/mg$_{sorbent}$, $q_e$ is the equilibrium uptake in mg/mg$_{sorbent}$ and $k_2$ is the second-order rate constant in s⁻¹.

Other embodiments are within the scope of the following claims.

What is claimed is:

1. A composition comprising:
an ultrafine microporous biotemplated filamentous carbon nanofiber with micropores smaller than 20 nm and up to 2000 m2/g surface area without activation having an aspect ratio of about 135, wherein a precursor for the ultrafine microporous biotemplated filamentous carbon nanofiber includes an alcohol and an aldehyde cross-linked by a primary amine.

2. The composition of claim 1, wherein the precursor for the carbon nanofiber is associated with a template.

3. The composition of claim 2, wherein the template is a bacteriophage.

4. The composition of claim 3, wherein the bacteriophage is M13.

5. The composition of claim 4, wherein the M13 is modified by inserting an EEAE peptide moiety.

6. The composition of claim 2, wherein the template is a carbon nanotube.

7. The composition of claim 2, wherein the template is an iron oxide nanoparticle.

8. The composition of claim 1, wherein the alcohol is resorcinol.

9. The composition of claim 1, wherein the aldehyde is formaldehyde.

10. The composition of claim 1, wherein the primary amine is a bifunctional primary amine.

11. The composition of claim 10, wherein the bifunctional primary amine is ethylenediamine.

12. The composition of claim 1, wherein the primary amine includes a silicon moiety.

13. The composition of claim 12, wherein the primary amine is 3-aminopropyltrimethoxysilane (APTMS).

14. The composition of claim 1, wherein the composition includes pores.

15. The composition of claim 14, wherein the pores include micropores smaller than 2 nm in size.

16. The composition of claim 14, wherein the pores include macropores bigger than 100 nm in size.

17. The composition of claim 1, wherein a surface area of the composition is in a range of 200 m2/g and 2000 m2/g.

18. A method of making the composition of claim 1 including a carbon nanofiber comprising:
forming a precursor by crosslinking an alcohol and an aldehyde using a primary amine; and
carbonizing the precursor.

19. The method of claim 18, further comprising incorporating the precursor in a template.

20. The method of claim 19, wherein the template is a bacteriophage.

21. The method of claim 18, wherein the precursor includes a single phase of crosslinked polysiloxane, aliphatic and phenolic moieties.

22. The method of claim 18, wherein the forming the precursor is carried out in a pH range of 8.3-8.8.

23. The method of claim 22, wherein the forming the precursor is carried out with mechanical agitation.

24. The method of claim 18, further comprising tuning nanotexture of the carbon nanofiber by tuning a content of a silicon moiety.

25. A method of removing a contaminant comprising:
administering into a contaminated site the composition of claim 1; and removing the composition after adsorption to a contaminant.

* * * * *